(12) United States Patent
Hasegawa et al.

(10) Patent No.: US 10,571,470 B2
(45) Date of Patent: Feb. 25, 2020

(54) BIOLOGICAL INFORMATION MEASUREMENT SYSTEM

(71) Applicant: TOTO LTD., Kitakyushu-shi, Fukuoka (JP)

(72) Inventors: Aya Hasegawa, Kitakyushu (JP); Tetsuhiro Wasada, Kitakyushu (JP); Aya Takao, Kitakyushu (JP); Satoko Kizuka, Kitakyushu (JP); Hidenori Oka, Kitakyushu (JP); Akemi Takeshita, Kitakyushu (JP); Masayuki Nagaishi, Kitakyushu (JP); Koji Sonoda, Kitakyushu (JP); Shingo Yamaya, Kitakyushu (JP); Hiroshi Tsuboi, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 388 days.

(21) Appl. No.: 15/546,919

(22) PCT Filed: Dec. 14, 2015

(86) PCT No.: PCT/JP2015/084898
§ 371 (c)(1),
(2) Date: Jul. 27, 2017

(87) PCT Pub. No.: WO2016/121247
PCT Pub. Date: Aug. 4, 2016

(65) Prior Publication Data
US 2017/0370936 A1 Dec. 28, 2017

(30) Foreign Application Priority Data

Jan. 30, 2015 (JP) .................................. 2015-017454
Nov. 27, 2015 (JP) .................................. 2015-232232

(51) Int. Cl.
*A61B 5/00* (2006.01)
*G01N 33/574* (2006.01)
(Continued)

(52) U.S. Cl.
CPC ..... *G01N 33/57419* (2013.01); *A61B 5/0004* (2013.01); *A61B 5/082* (2013.01);
(Continued)

(58) Field of Classification Search
CPC ............................................. G01N 33/57419
See application file for complete search history.

(56) References Cited

FOREIGN PATENT DOCUMENTS

| JP | 2000-271097 A | 10/2000 |
|---|---|---|
| JP | 2005-292049 A | 10/2005 |

(Continued)

OTHER PUBLICATIONS

Yamagishi, K. et al., "Generation of Gaseous Sulfur-Containing Compounds in Tumour Tissue and Suppression of Gas Diffusion As an Antitumour Treatment", *Gut*, vol. 61, No. 4, 2011, pp. 554-561.
(Continued)

*Primary Examiner* — Carl H Layno
*Assistant Examiner* — Dacheng Xie
(74) *Attorney, Agent, or Firm* — Brinks Gilson & Lione

(57) ABSTRACT

The biological information measurement system of the present invention includes a test subject-side device provided in a toilet installation room, and a server communicable with the test subject-side device, the test subject-side device includes a sulfur-containing gas sensor sensitive to sulfur-containing gas and outputting detection data, a transmitter-receiver transmitting measurement data including detection data of the sulfur-containing gas detected by the sulfur-containing gas sensor to the server, and the server includes a database in which measurement data including detection data of sulfur-containing gas detected by the (Continued)

sulfur-containing gas sensor is accumulated and recorded with dates and times of defecation acts by being associated with test subject identification information, and server-side data analyzer that analyzes physical condition of a test subject on the basis of a time-dependent variation tendency of the measurement data accumulated and recorded in the database.

14 Claims, 32 Drawing Sheets

(51) Int. Cl.
  *G06Q 50/22*   (2018.01)
  *G01N 33/00*   (2006.01)
  *G06Q 10/10*   (2012.01)
  *G06Q 30/02*   (2012.01)
  *A61B 5/08*   (2006.01)
  *G01N 33/497*   (2006.01)

(52) U.S. Cl.
  CPC .......... *A61B 5/4255* (2013.01); *A61B 5/4283* (2013.01); *A61B 5/6891* (2013.01); *G01N 33/005* (2013.01); *G01N 33/0044* (2013.01); *G01N 33/0059* (2013.01); *G01N 33/0062* (2013.01); *G01N 33/0073* (2013.01); *G06Q 10/101* (2013.01); *G06Q 30/0201* (2013.01); *G06Q 50/22* (2013.01); *A61B 2505/07* (2013.01); *A61M 2230/432* (2013.01); *G01N 2033/4975* (2013.01)

(56) References Cited

FOREIGN PATENT DOCUMENTS

| JP | 2009-052943 A | | 3/2009 |
|---|---|---|---|
| JP | 2009-204606 A | | 9/2009 |
| JP | 2009-205456 A | | 9/2009 |
| JP | 2009-250922 A | | 10/2009 |
| JP | 2009250922 A | * | 10/2009 |
| JP | 2010-175432 A | | 8/2010 |
| JP | 2010-230359 A | | 10/2010 |
| JP | 2014160049 A | * | 9/2014 |

OTHER PUBLICATIONS

Yamagishi, K. et al., "Casual Relationship Between Sulfur-Containing Gas Generated in Cancer Lesion and Cancer Growth", *Dental Diamond*, vol. 36, No. 15, 2011, pp. 60-67. (English translation included).

Office Action in Japan Application No. 2015-232233, dated Jul. 18, 2019, pages.

* cited by examiner

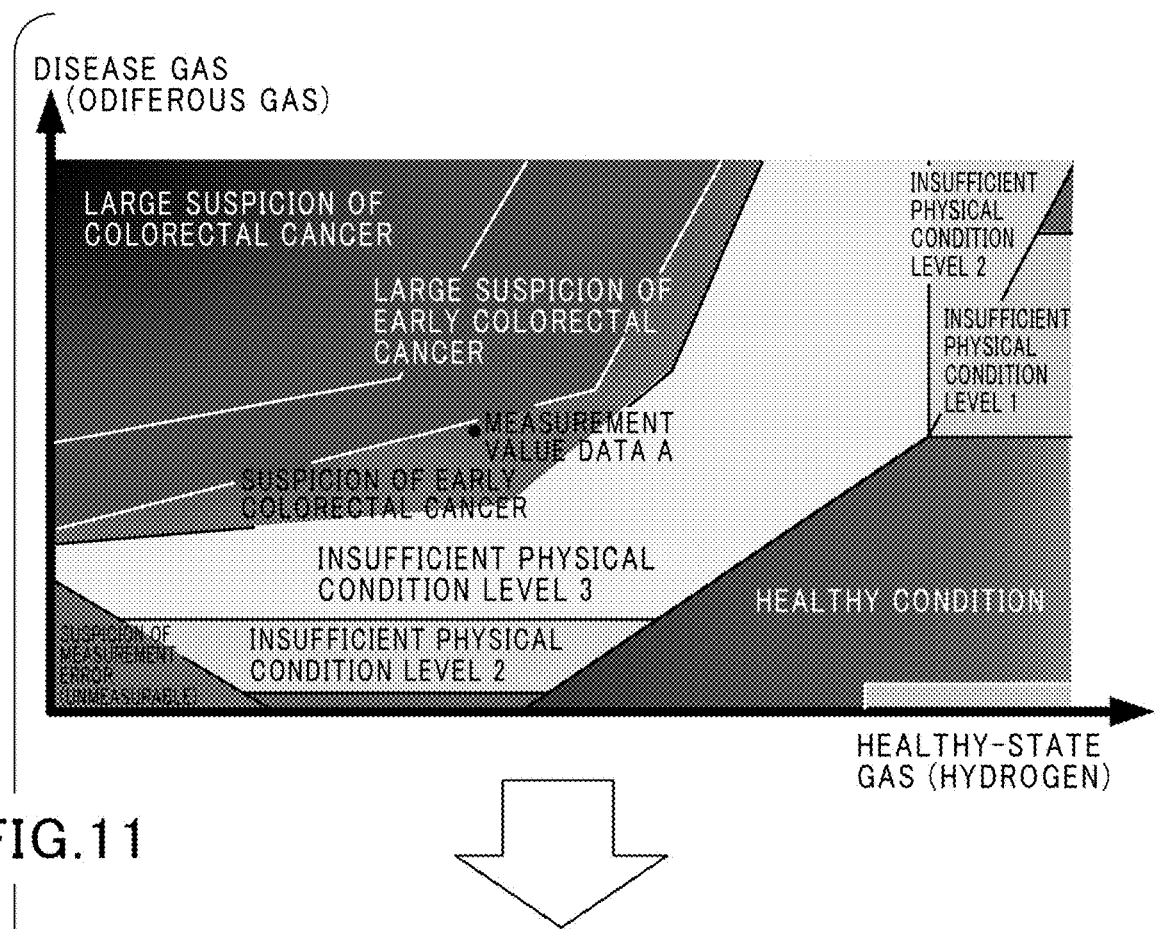
FIG.11
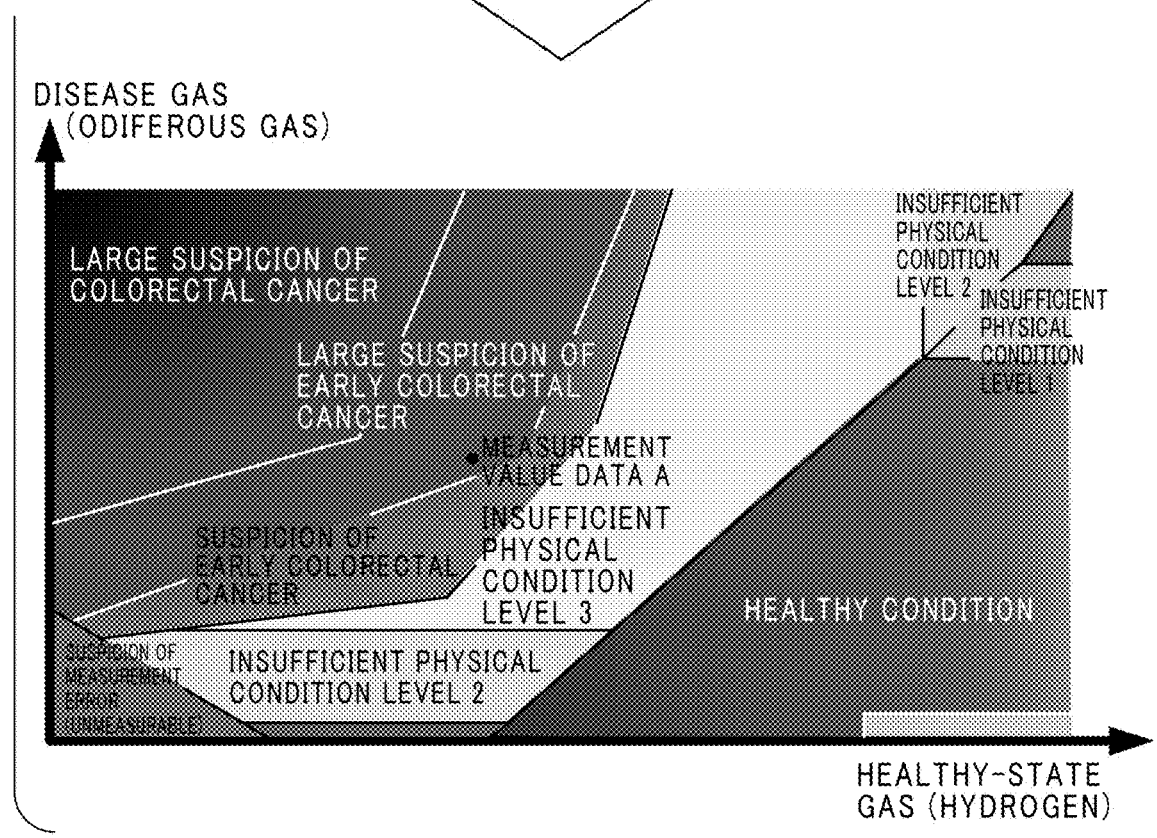

CORRECTION FOR NOISE OF STINK GAS ATTACHED TO TEST SUBJECT

CORRECTION FOR HUMIDITY

CORRECTION FOR TEMPERATURE

CORRECTION FOR FREQUENCY OF EXCRETORY ACTS

CORRECTION FOR ENVIRONMENTAL NOISE

CORRECTION FOR STABILITY OF REFERENCE VALUE

CORRECTION FOR CLEANING OF DISINFECTING TOILET SEAT

CORRECTION FOR TOTAL AMOUNT OF DEFECATION GAS

CORRECTION FOR FART

CORRECTION FOR AMOUNT OF STOOL

CORRECTION FOR KIND OF STOOL

CORRECTION FOR INTERVAL
/FREQUENCY OF DEFECATION

CORRECTION FOR AMOUNT OF ACCUMULATED DATA
(NUMBER OF TIMES OF MEASUREMENT RECORDED VALUE)

CORRECTION FOR FLOW RATE OF AIR

CORRECTION FOR $CO_2$

CORRECTION FOR METHANE

CORRECTION FOR HYDROGEN SULFIDE (CONCENTRATION (CALCULATED FROM SLOPE) × REACHING TIME TO PEAK)

HYDROGEN SULFIDE DATA

AVERAGE VALUE OF HYDROGEN SULFIDE

METHYL MERCAPTAN DATA

AVERAGE VALUE OF METHYL MERCAPTAN

CARBON DIOXIDE DATA

AVERAGE VALUE OF CARBON DIOXIDE

PROPIONIC ACID DATA

AVERAGE VALUE OF PROPIONIC ACID

ACETIC ACID DATA

AVERAGE VALUE OF ACETIC ACID

BUTYRIC ACID DATA

AVERAGE VALUE OF BUTYRIC ACID

BIOLOGICAL INFORMATION MEASUREMENT SYSTEM

This application is a 371 application of PCT/JP2015/084898 having an international filing date of Dec. 14, 2015, which claims priority to JP2015-017454 filed Jan. 30, 2015 and JP2015-232232 filed Nov. 27, 2015, the entire contents of which are incorporated herein by reference.

TECHNICAL FIELD

The present invention relates to a biological information measurement system, and more particularly to a biological information measurement system that measures physical condition of a test subject on the basis of defecation gas discharged in a bowl of a toilet installed in a toilet installation room.

BACKGROUND ART

In recent years, a mortality rate caused by cancer extremely decreases due to evolution of a diagnosis technique for serious illness, such as cancer, and of a technique of cancer treatment, with evolution of medical technology. However, presenting to a hospital at regular intervals for diagnosis to prevent cancer burdens a patient. In contrast, many patients actually present to a hospital after realizing wrong physical condition, and thus unfortunately still many people have cancer. In addition, no practical device for preventing cancer has been developed yet, so that it cannot be said that cancer prevention is sufficiently achieved.

In light of the circumstances, the present inventors have studied for a long time with a strong desire for manufacturing a device that is really required in the market, such as a device capable of more simply and easily diagnosing serious illness, such as cancer, at home without presenting to a hospital, to achieve prevention or early treatment of serious illness.

The present applicants have developed devices, such as: a device that is mounted in a seat of a Western-style toilet to collect defecation gas discharged into a bowl when a test subject defecates to acquire the amount of stool discharged on the basis of a concentration of carbon dioxide contained in the defecation gas as a biological information index (refer to Patent Literature 1); and a device in which a deodorizing device assembled in a seat of a flush toilet sucks defecation gas that is discharged together when a test subject defecates so that a carbon dioxide gas sensor measures a concentration of carbon dioxide of the gas sucked to allow intestinal conditions of a test subject to be estimated on the basis of the measured concentration of carbon dioxide (refer to Patent Literature 2). Unfortunately, these devices estimate only current intestinal conditions, so that it is impossible to achieve a purpose of the present inventors to enable serious illness, such as cancer, to be simply and easily diagnosed, as well as to enable a risk state of the serious illness to be simply and easily acquired. In addition, there is also known a fart detector in which gas sensor is arranged so as to be brought into contact with air near an excretory organ of a human to detect a fart on the basis of a peak value of output of the gas sensor (Patent Literature 3). In the fart detector, a tube inserted into an excretory organ of a patient staying in bed in a diaper or underwear worn by the patient is drawn, and air is sucked through the tube by a suction pump to collect a fart of the patient. In addition, the fart detector only distinguishes a fart and urination on the basis of a half-value width of a peak value of output of the gas sensor so that a doctor checks whether a fart is discharged after an appendix operation, or time to replace a diaper is detected, whereby it is impossible to achieve the purpose of the present inventors. Meanwhile, Japanese Patent Laid-Open No. 2014-160049 (Patent Literature 4) discloses a portable type apparatus for measuring a risk of colorectal cancer that includes a sensor for measuring methyl mercaptan gas from components of a fart discharged by a test subject, a calculation unit for calculating a concentration of the methyl mercaptan gas measured by the sensor, and a display, to estimate a risk of acquiring colorectal cancer.

Japanese Patent Laid-Open No. 9-43182 (Patent Literature 5) describes a biological monitoring device. In the biological monitoring device, a fabric T-bandage to which gas sensor is attached is provided so that the gas sensor is arranged near an anus to detect a fart discharged from the anus. A signal from the gas sensor is transmitted to a processor to be stored in a memory. It is also known that data stored in a memory is compared with previous data, and that a warning is displayed in a display device if there is abnormality, such as a large difference.

Japanese Patent No. 3525157 (Patent Literature 6) describes a method of measuring components of flatus. In the method of measuring components of flatus, a sampling tube is arranged at a portion in a seat of a toilet. When a person to be measured turns on a main switch of a device, a suction pump is operated to suck gas near an anus. An index gas detector always measures a concentration of carbonic acid gas in the gas sucked, and a control/arithmetic processing unit recognizes that a flatus has been diffused if the concentration measured steeply increases. If a flatus is diffused, another suction pump starts operating to allow a part of gas sucked to be inserted into a sample measuring tube. An inserted sample is fed into a column so that gas components are separated to be ionized. It is also known that the amount of ionization is converted into an electric signal so that a concentration of gas components of a detection object in the flatus is measured.

Japanese Patent Laid-Open No. 2014-206945 (Patent Literature 7) describes a health information utilization system. In the health information utilization system, personal health information on health management, inputted from a terminal device, is individually stored in a database of each of a plurality of data centers, and an analysis server device reads out the personal health information to analyze it. A big data creation server device searches the personal health information under a specific condition to create big data and store it. The health information utilization system allows health content based on knowledge in a special field to be browsed at a terminal device, and stores the personal health information in the plurality of data centers to manage it, as well as allows a health determination result acquired by applying automatic determination processing to the personal health information, and a health determination result acquired by determination processing applied by an expert, to be browsed at a terminal. The system described above is also known.

In order to develop a device capable of diagnosing serious illness, such as cancer, in recent years, it has been known that there is a correlation between disease of colorectal cancer and components of flatus contained in a fart and a stool, as also described in Patent Literature 4 described above, for example. Specifically, colorectal cancer patients have more methyl mercaptan gas containing a sulfur component, in components of flatus, as compared with healthy people.

CITATION LIST

Patent Literature

[Patent Literature 1]
   Japanese Patent No. 5131646
[Patent Literature 2]
   Japanese Patent No. 5019267
[Patent Literature 3]
   Japanese Patent Laid-Open No. 2003-90812
[Patent Literature 4]
   Japanese Patent Laid-Open No. 2014-160049
[Patent Literature 5]
   Japanese Patent Laid-Open No. 9-43182
[Patent Literature 6]
   Japanese Patent No. 3525157
[Patent Literature 7]
   Japanese Patent Laid-Open No. 2014-206945

SUMMARY OF INVENTION

Technical Problem

Components of flatus are discharged along with a stool, as a fart and defecation gas, during defecation. Thus, the present inventors, as published in Nihon Keizai Shimbun issued Jan. 5, 2015, have studied on the assumption that measuring a specific gas, such as methyl mercaptan gas, in a fart and defecation gas, discharged during defecation, enables colorectal cancer in the intestine to be found out, as with Patent Literature 4 above, and the like. However, a measuring device capable of accurately measuring only this specific gas, such as methyl mercaptan gas, is very expensive and large in size. In addition, methyl mercaptan gas is contained in minute amount in defecation gas, and is contained in less amount than the minute amount in a stage before getting cancer. As a result, it is very difficult to measure the methyl mercaptan gas, and thus the present inventors have been faced with a problem in which it is not realistic in cost and size that at least this kind of gas analyzer capable of accurate measurement is assembled in a household toilet device to be widely used as a consumer product.

However, the present inventors desire to reduce the number of people who have a serious illness, such as cancer, as far as possible. To achieve this object, the present inventors continue to study by having strong feeling for necessity of providing a device that is capable of allowing general consumers to readily purchase it, and capable of simply and easily performing diagnosis at home, and then finally find out a technical solution for realizing the device.

It is an object of the present invention to provide a diagnosis system that is capable of allowing general consumers to readily purchase it, as well as capable of measuring defecation gas at home to prevent people from having a serious disease, such as a cancer, or urging people to present to a hospital to receive treatment under a moderate condition, the diagnosis system being really required in the market, having high practicality.

Solution to Problem

The present invention is a biological information measurement system that measures physical condition of a test subject on the basis of defecation gas discharged into a bowl of a flush toilet, the biological information measurement system including: a test subject-side device provided in a space where the flush toilet is installed; and a server communicable with the test subject-side device, wherein the test subject-side device includes a suction device that sucks gas in the bowl into which the defecation gas is discharged during a defecation act of the test subject, a gas detector that is sensitive to methyl mercaptan gas that is odiferous gas containing a sulfur component and odiferous gas other than methyl mercaptan gas, which are contained in the gas sucked by the suction device, and outputs first detection data, a test subject identification device that accepts input of test subject identification information, a control device that controls the suction device and the gas detector, and a communication device that transmits measurement data including the first detection data of the odiferous gas detected by the gas detector to the server, and the server includes a database in which the measurement data including the first detection data of the odiferous gas detected by the gas detector is accumulated and recorded with dates and times of defecation acts by being associated with the test subject identification information accepted by the test subject identification device, a server-side data analyzer that analyzes physical condition of a test subject on the basis of a time-dependent variation tendency of the measurement data accumulated and recorded in the database, and an server-side output device that outputs an analysis result by the server-side data analyzer.

Heretofore, there has been actually no effective device other than diagnosis at hospital for checking whether people have serious illness, such as cancer, or for checking people for prevention of serious illness. In contrast, according to the present invention, general consumers can simply and easily purchase the test subject side devices, and perform measurement at home. In addition, it is possible to allow a test subject to be prevented from having a serious disease, such as cancer, or to present to a hospital to receive treatment under a moderate condition, by only performing an excretory act that is daily performed, as usual to measure defecation gas discharged during defecation without making an effort to perform additional measurement action. In this way, the present invention achieves an excellent effect of enabling a device that is really required in the market to be realized and a diagnosis system having high practicality to be provided.

Before advantageous effects of the present invention is specifically described, a technical idea of allowing a system to be widely used at standard home as a consumer product will be described. Key point of the idea are reverse thinking and effective simplified knowledge acquired by understanding characteristics of serious illness, such as cancer, and using the characteristics.

Specifically, one of key points of a system of the present invention is acquired by reverse thinking of a test subject-side device installed at each home by which people are not diagnosed as having serious illness, such as cancer. That is, a test subject of general consumers who purchase the test subject side device really wants to know whether the test subject is in a stage before having cancer (hereinafter this stage is referred to as ahead-disease), instead of whether the test subject has cancer, to recognize an increasing risk of cancer to improve a future life to preventing having cancer. Thus, it is thought that a device capable of allowing health people to accurately recognize a risk of cancer to improve physical condition for preventing having cancer is worth to a device required at standard home.

Another key point of the system of the present invention is acquired by a simplified idea that a device capable of diagnosing a specific kind of cancer, such as a rectal cancer, or diagnosing an increasing risk of a specific kind of cancer, is unnecessary. The idea is acquired from characteristics of a test subject who is anxious about any kind of cancer instead of about a specific kind of cancer, such as a rectal cancer. Thus, the inventors have simply thought that accuracy of measurement capable of identifying a kind of cancer is unnecessary, on the basis of an assumption that it is quite unnecessary to identify a kind of cancer instead of an assumption that device has a commercial value if diagnosing a specific kind of cancer.

Another key point of the system of the present invention is a simplified idea that it does not matter if diagnosis precision to a defecation act of each time is extremely low. This is the idea based on the characteristics of disease of cancer developing for a long time, or a few years, and is realization that diagnosis opportunities extend over a long period of years. Thus, the inventors have found that as long as the system is in the position of a device for healthy people to reduce the risk of becoming cancer voluntarily, even if diagnostic precision of each time is low, influence thereof has practically no problem, and an effective simplified idea based on the realization is one of the key points.

Specific effects of a system in accordance with the present invention configured on the basis of the knowledge and the effective simplified idea described above will be described below.

In the present invention, since defecation gas discharged into a bowl of a toilet is measured to analyze physical condition of a test subject, it is possible to perform diagnosis by allowing a test subject to only perform defecation performed every day, as usual without requiring an effort to perform measurement action. Requiring no effort allows the test subject to have no burden, so that it is possible to continue measurement for a long time to reliably acquire information on a change in health condition, and on a state where a risk of cancer is increasing.

In addition, in the present invention, no sensor for measuring methyl mercaptan gas at a pinpoint is used, and a sensor that is widely sensitive also to odiferous gas other than the methyl mercaptan gas, in defecation gas, is used. If the sensor for measuring methyl mercaptan gas at a pinpoint is used, it is possible to reliably detect a colorectal cancer because there is a correlation between the amount of methyl mercaptan gas and a colorectal cancer, and also to reliably find that a risk of cancer is increasing from the amount thereof. However, it is found that it is impossible to determine that a risk of cancer is increasing unless a risk of cancer increases to some extent to increase the amount of methyl mercaptan gas, whereby the sensor is unsuitable for the present invention having an object to prevent people from having cancer.

In contrast, the sensor that is widely sensitive to odiferous gas is capable of detecting not only a state where a risk of cancer is increasing, but also a risk of cancer from wrong physical condition. Specifically, first if a risk of cancer increases, a very strong odiferous gas containing a sulfur component, such as methyl mercaptan gas or hydrogen sulfide, increases in amount. Then, the sensor that is widely sensitive to odiferous gas is capable of detecting increase of this kind of gas. Further, as described later, although an amount of odiferous gas may temporarily increase depending on a daily change in physical condition, a state of having an increased very strong odiferous gas containing a sulfur component, such as methyl mercaptan gas or hydrogen sulfide, continues for a long time, if people have cancer. Thus, even if a sensor that is widely sensitive to odiferous gas other than methyl mercaptan gas in defecation gas is used, it is possible to determine that there is a high possibility of disease of cancer to cause a risk of cancer to increase if the amount of gas is high for a long time. Accordingly, the sensor that is widely sensitive also to odiferous gas serves also as a sensor for measuring methyl mercaptan gas at a pinpoint in this point.

The present invention uses a gas detector that is sensitive not only to methyl mercaptan gas but also to odiferous gas other than methyl mercaptan gas, in defecation gas, so that only the amount of odiferous gas in the defecation gas can be detected, but the amount of methyl mercaptan gas cannot be measured, whereby it is impossible to accurately identify a state of cancer. However, the present inventors find out that using gas detector that is sensitive not only to methyl mercaptan gas, but also to odiferous gas other than methyl mercaptan gas, in defecation gas, allows a device to effectively serve as a device for preventing a state where a risk of cancer increases in healthy people, and a risk, such as having cancer. Specifically, healthy people have a small total amount of methyl mercaptan gas and odiferous gas other than the methyl mercaptan gas. In contrast, a total amount of methyl mercaptan gas and odiferous gas other than the methyl mercaptan gas temporarily increases due to deterioration of intestinal environment other than having cancer. The deterioration of intestinal environment is specifically caused by the following, such as excessive obstipation, a kind of meal, lack of sleep, crapulence, excessive drinking, and excessive stress. It can be said that each of these causes is a bad living habit. The bad living habit will result in cancer, however, there is no means of recognizing a risk of cancer state even if the risk of cancer increases, and thus many people continue the bad living habit on the basis of a convenient assumption that the many people themselves survive.

In this way, performing the bad living habit as described above increases all or any one of odiferous gases in defecation gas, such as methyl mercaptan, hydrogen sulfide, acetic acid, trimethylamine, or ammonia. In contrast, the present invention analyzes physical condition on the basis of detection data acquired by gas detector that detects not only methyl mercaptan gas, but also odiferous gases other than methyl mercaptan gas, such as hydrogen sulfide, acetic acid, trimethylamine, or ammonia, in defecation gas. Thus, an analysis result based on a total amount of the odiferous gas in the defecation gas reflects a result caused by a wrong physical condition and a bad living habit, of a test subject, so that the analysis result is usable as an index based on objective data for improving a physical condition and a living habit in which this kind of risk of cancer may increase, or is usable as an effective index for maintaining a health condition to reduce a risk of having cancer, whereby it is found that the analysis result acts on the object of improving a living habit and reducing a risk of cancer in an extremely effective manner to achieve an excellent effect.

In this way, the present invention measures methyl mercaptan gas and odiferous gas other than the methyl mercaptan gas to enable measurement capable of notifying a state where a risk of cancer may increase, and a suitable warning of having cancer if this kind of state continues for a long time, to a test subject. The so-called reverse thinking allows knowledge suitable for the object of reducing people having cancer to be found out.

In addition, since the present invention uses a sensor that is widely sensitive not only to methyl mercaptan gas but also to odiferous gas other than the methyl mercaptan gas, a device can be manufactured at low cost, thereby enabling the device to be provided as a consumer product. Accordingly, it is possible to sufficiently satisfy a request of test subjects that diagnosis can be simply and easily performed at home to prevent having a serious disease, such as cancer, or they can be urged to present to a hospital to receive treatment under a moderate condition.

Further, according to the present invention, defecation gas is measured in an everyday ordinary act of defecation, so that even if measurement precision of each time is low, use of measurement data of a huge number of times accumulated and stored in the database makes it possible to ensure precision of analysis to find a risk of cancer increasing, or that cancer is under development to a necessary and sufficient extent.

Further, the present invention is not a device that performs analysis of physical condition on the basis of only measurement data of a defecation act of one time, and therefore needs to accumulate long-term measurement data, and further needs to perform analysis based on long-term measurement data. Assembling accumulated measurement data like this and an analysis system into the device for a test subject, which is installed in each household causes cost increase, and prevents the device for a test subject from being widely used as a consumer product. In contrast, the present invention transmits measurement data to the server to manage the measurement data in the database, and performs analysis of physical condition on the server side, and thereby can provide the device for a test subject which is purchased by a consumer, at a low price. Further, the server performs analysis of physical condition, so that precision of the analysis can be dramatically enhanced.

Further, in the present invention, it is preferable that the test subject-side device further includes a test subject-side data analyzer that analyzes physical condition of a test subject on the basis of the time-dependent variation tendency of the measurement data, and a test subject-side output device that outputs an analysis result by the test subject-side data analyzer.

According to the present invention of the configuration like this, analysis of physical condition of the test subject is also performed in the test subject-side device, and can be outputted to the test subject, so that frequencies of analysis and notification in the server are decreased to enable a burden to be reduced, and the test subject can improve daily life quickly, reliably and easily on the basis of display to the test subject-side output device.

Further, in the present invention, it is preferable that the gas detector is further sensitive to healthy-state gas composed of at least one of hydrogen gas, carbon dioxide, or methane gas contained in gas sucked by the suction device, and outputs second detection data, the measurement data includes the second detection data of the healthy-state gas, and analysis by the test subject-side data analyzer is simpler than analysis by the server-side data analyzer.

Although it does not matter if the frequency of diagnosis is low because cancer is a disease developing after spending a long time, very high precision is required for the precision of the detailed analysis of a disease of cancer, or the like. Meanwhile, in order to improve a living habit when people are still in a state before having a disease at a stage before having cancer, it is desirable to enable a test subject to obtain an analysis result of physical condition quickly at a time of defecation act or the like, every day. However, considering a burden of analysis on the server and a burden of doctors, it is not realistic that detailed analysis is performed on the server side, and a doctor and the like perform diagnosis on the basis of the analysis result, every day. Further, in the system that performs analysis with a high frequency and high precision on the server side, a usage fee of the system is also high, so that it is not realistic from this point of view. In contrast, according to the present invention of the above described configuration, detailed analysis can be performed on the server side while increase in price of the test subject-side device is suppressed, by causing the server side analyzer and the test subject-side device to participate in roles well, by using the characteristics of cancer being a disease developing after spending a long time.

That is, according to the present invention of the above described configuration, the practical system that can satisfy both of the above described demands and is excellent to a serious disease such as cancer can be provided. Specifically, the functions are separated between the server side analyzer and the test subject-side data analyzer, and the server side analyzer is given a medical diagnosis function with high precision and a low frequency, whereas the test subject-side data analyzer is given a simple health management function to such an extent as to reveal that a risk of a serious disease such as cancer is increasing, so as to enable notification of simple analysis with a high frequency to be performed. Thereby, a test subject acquires information timely with a high frequency, and can manage physical condition. Although the frequency of the detailed analysis on the server side is low, no influence is exerted, because cancer is a disease developing after spending a long time. On the contrary, the situation of the risk of cancer can be accurately analyzed while an analysis burden is decreased by reducing the frequency of analysis on the server side, and an analysis result is enabled to be notified accurately. By dividing the roles in this way, the detailed situation of a disease of cancer and increase in the risk of cancer can be accurately grasped on the server side, and the test subject-side data analyzer is enabled to determine a change in physical condition accompanying a bad living habit accurately every day to encourage a test subject to make an effort to improve the living habit.

Further, in the present invention of the above described configuration, physical condition is analyzed on the basis of the first detection data of odiferous gas containing a sulfur component, and the second detection data of healthy-state gas. This is based on the excellent technical knowledge by the inventors, that precision of analysis is dramatically enhanced by performing analysis on the basis of odiferous gas containing a sulfur component and healthy-state gas, and precision of analysis to such an extent that an intestinal change occurs or a risk of cancer increases can be ensured by performing simple measurement. Specifically, although the amount of odiferous gas temporarily increases and decreases depending on a change in physical condition, the amount of odiferous gas continuously increases certainly in a state in which a risk of cancer is increasing due to a change in an intestinal environment. Further, an amount of healthy-state gas certainly decreases continuously in such a manner as to be inversely proportional to the increase in the amount of odiferous gas. Accordingly, if the relationship between the amount of odiferous gas and the amount of healthy-state gas is used, accurate analysis of physical condition is enabled even with simple analysis, by performing analysis on the basis of odiferous gas containing a sulfur component and healthy-state gas, even if all of defecation gases of the test subject are collected, and an entire amount of odiferous gas in them is not accurately grasped. Thereby, a change in physical condition can be detected by simple analysis based on the relationship between odiferous gas and healthy-state gas in the defecation gases collected in a short time, and accurate analysis can be performed to find that a risk of cancer increases. According to the present invention based on the knowledge, it becomes possible to perform useful analysis by using the test subject-side device that is installed on a test subject side and performs simple analysis, so that simple analysis can be performed with a high frequency, and a state of physical condition can be notified at a high frequency.

Meanwhile, odiferous gas is in a very small of amount, so that in order to perform analysis with only the odiferous gas, there is a problem in the measurement system and measurement precision when a measurement error is taken into consideration. In order to ensure reliability of measurement data sufficiently, a sensor for odiferous gas which have high sensitivity and is very expensive is needed, and it has been difficult to suppress increase in price of the system on a consumer side. According to the present invention of the above described configuration, it becomes possible to ensure sufficient reliability of analysis and enhance precision of analysis of physical condition dramatically, by only adding a low-priced sensor for healthy-state gas to a simple sensor for odiferous gas without using an expensive sensor, by using the analysis method based on the above described technical knowledge found by the inventors.

Further, in order to analyze both of odiferous gas and healthy-state gas, an analysis load is considered to be large, however, in the present invention of the above described configuration, simple analysis using the relationship of the two gases is adopted in the test subject-side device, so that it becomes possible to suppress an analysis load in the test subject-side device. Further, for analysis on the server side, sufficiently accurate analysis is enabled even by using the data collected by the low-priced odiferous gas sensor. Further, according to the present invention of the above described configuration, precision of analysis on the server side is enhanced by performing analysis on the basis of the odiferous gas containing a sulfur component and healthy-state gas, and an erroneous diagnosis and a useless instruction to go to hospital can be reduced in diagnosis by a doctor, so that a useless mental burden can be prevented from being applied to a test subject, and a large merit is provided to the test subject.

Further, in the present invention, it is preferable that the analysis result outputted by the server-side output device includes a determination result concerning a specific disease, and the analysis result outputted by the test subject-side output device includes a history of the measurement data, and does not include a determination result concerning the specific disease.

Since notification of the analysis result concerning a disease applies a mental burden to a test subject, it is preferable that notification is performed based on more accurate analysis. However, as described above, analysis in the test subject-side data analyzer is simple. According to the present invention of the above described configuration, the analysis result by the test subject-side output device does not include the determination result concerning a specific disease, so that a mental burden is not applied to the test subject, and the history of the measurement data is further outputted to the test subject-side output device. Thus, the test subject can grasp a change in physical condition by checking a change in data, and if a change in data arises on the day after the test subject performs a bad living habit such as crapulence, the test subject can directly grasp a change amount as a bad result based on the bad living habit. Thus, the test subject can be encouraged to improve the bad living habit, and make an effort to improve physical condition reliably. Further, according to the present invention of the above described configuration, analysis with higher precision is performed on the server side, so that an erroneous diagnosis and the like can be prevented. In this way, according to the present invention of the above described configuration, the excellent system in practical use can be constructed, which can ensure precision of diagnosis of cancer and the like at a high level while realizing a price as a consumer product by a device to perform analysis requiring high precision such as a cancer diagnosis is performed in detail on the server side, and give the role of reducing a risk of healthy people having cancer to the test subject-side device.

Further, in the present invention, it is preferable that the test subject-side data analyzer analyzes physical condition of a test subject on the basis of data in a partial period in a defecation act, of the measurement data, and the server-side data analyzer analyzes physical condition of a test subject on the basis of data in a longer period than the partial period in the defecation act, of the measurement data.

For analysis of a specific disease such as cancer in the server side analyzer, it is desirable to measure an amount of odiferous gas accurately for a long period during a defecation act, in an aspect of ensuring precision of the measurement, because there is a relationship between cancer and the amount of methyl mercaptan gas. In contrast, the analysis in the test subject-side device is for management of physical condition that does not include determination of a disease, so that it is unnecessary to grasp an entire amount of odiferous gas generated in a body accurately, because the method for performing analysis based on a correlation between odiferous gas and healthy-state gas is found as described above. Accordingly, the test subject-side device can perform analysis on the basis of the correlation between the amount of odiferous gas and healthy-state gas in gases collected in a short period, so that analysis can be performed accurately and quickly without an analysis burden. The effective simplified idea is realized by the useful finding, and analysis precision in the test subject-side device can be ensured.

Further, in the analysis in the test subject-side device, it is desirable to receive a result immediately after defecation. That is, when analysis using all data in the period of a defecation act is performed, analysis is started after a test subject finishes the defecation act and starts preparation for exit, so that the device is very bad in usability because the test subject needs to wait wastefully until the test subject receives a result in the toilet space even after the defecation act. However, according to the present invention of the above described configuration, analysis in the test subject-side device is performed with only the data in a short specific partial period in a defecation act period, so that it becomes possible to start analysis during a defecation act. This enables the test subject to receive the result during a defecation act or immediately after the defecation act, and enables the test subject to avoid state of waiting to obtain the result in the toilet space when there is no time before going to work in the morning. The effect in the system performing management of physical condition in a toilet space is a very useful peculiar effect.

Further, in the present invention, it is preferable that measurement data in an entire period of the defecation act is recorded in the database, and the server-side data analyzer analyzes physical condition of a test subject on the basis of the measurement data in the entire period of the defecation act.

There is the knowledge that an amount of methyl mercaptan gas generated in a body is increased by cancer cells when having cancer. The server that determines a disease makes analysis on the basis of an entire amount of odiferous gas in the period of a defecation act, so that diagnosis of cancer that is correlated with the generation amount of methyl mercaptan gas can be made with higher precision, and accurate analysis of a disease is enabled.

In the present invention, it is preferable that the test subject-side data analyzer further includes a reliability determination circuit that determines reliability of the first detection data outputted by the gas detector, and the test subject-side data analyzer analyzes physical condition of a test subject on the basis of measurement data in a period in which reliability determined by the reliability determination circuit is high, of the measurement data.

In the present invention using the sensor that is widely sensitive to odiferous components, the first detection data is influenced by odiferous gas components such as sweat and urine attached to a test subject, a perfume, a stool attached to a toilet, odiferous gas or an aromatic remaining in a toilet space, an alcohol disinfectant and the like. Especially when a perfume and an aromatic are strong, and as the body and the toilet space are more insanitary, measurement precision may be reduced. Further, when a toilet is used immediately after defecation of another person, there is a high possibility of stink gas components of defecation gas and an attached odor of the person previously using the toilet remaining in the toilet and the toilet space, and influence is considered to be exerted on measurement even when the space is not insanitary. In contrast, according to the present invention of the above described configuration, reliability of the first detection data is determined by the reliability determination circuit, and physical condition is analyzed on the basis of the measurement data in the period in which reliability is high, so that analysis of the physical condition in the test subject-side data analyzer can be made accurate and stable. Further, for analysis on the server side, an erroneous diagnosis by an influence due to noise can be reduced, and a useless mental burden can be prevented from being given to a test subject.

In the present invention, it is preferable that the test subject-side data analyzer specifies an initial defecation gas detecting period in a period of a defecation act in the measurement data, and performs analysis on the basis of data in the specified initial defecation gas detection period, of the measurement data.

So far, it has been considered that since methyl mercaptan gas is generated by cancer cells, much gas is discharged with timing corresponding to the position of the cancer cells during a defecation period, but the inventors have found a tendency that much gas is discharged at an initial stage of the defecation act period. This is considered to be due to a characteristic of gas being discharged more easily than a stool at a time of defecation, and a characteristic of generated gas gathering near an anus with a lapse of time. In the present invention based on the knowledge, analysis is performed on the basis of defecation gas discharged at an initial defecation act in the test subject-side device, so that even with simple measurement, precision of analysis of physical condition necessary for health management can be dramatically enhanced. Further, analysis can be reliably started during a defecation act period by performing simple analysis with defecation gas of the initial time, so that the analysis result can be reliably provided during the defecation act or immediately after the defecation act. When the test subject can think of having a bad living habit, the test subject may be less willing to brows the analysis result. However, according to the present invention, the analysis result is provided during a defecation act or immediately after the defecation act, so that the test subject certainly brows the analysis result. Consequently, even the test subject who is less willing to brows the analysis result can be encouraged to improve physical condition.

In the present invention, it is preferable that the test subject-side data analyzer further includes reliability determination circuit that determines reliability of the first detection data outputted by the gas detector, the reliability as well as the measurement data is recorded in the database, and the reliability as well as an analysis result is outputted to the server-side output device.

According to the present invention of the above described configuration, reliability as well as an analysis result is outputted to the server-side output device, so that it can be accurately determined whether a state of a bad analysis result is caused by bad physical condition, or caused by noise due to an unsanitary environment or the like, and a useless mental burden can be reliably prevented from being applied. Further, the test subject can be encouraged to take action of cleaning a toilet, and removing a perfume, for example, so as to remove noise voluntarily, and it becomes possible to perform more accurate diagnosis.

In the present invention, it is preferable that the test subject-side device further includes an input device, the input device accepts input of defecation history information concerning a defecation history situation of the test subject, the defecation history information is recorded in the database, with the measurement data, and the defecation history information as well as an analysis result is outputted to the server-side output device.

For example, in an obstipation state, precision of diagnosis is reduced because generation of odiferous component gas takes a long time. When the dates and times of the measurement data recorded in the database are apart from one another, it can be determined that obstipation occurs, and a possibility of performing erroneous diagnosis of a risk of cancer increasing or the like can be prevented. Further, a test subject does not necessarily defecate in the toilet where the test subject-side device is provided. According to the present invention of the above described configuration, even when the dates and times of the measurement data recorded in the database are apart from one another, it can be determined whether or not obstipation occurs, and more accurate diagnosis can be performed. Conversely, when a test subject defecates in a different place, the amount of odiferous gas included in defecation gas may decrease. In contrast, according to the present invention of the above described configuration, even in the case where the amount of odiferous gas of this time is small, the case can be prevented from being erroneously diagnosed as healthy. In the present invention that manages physical condition, and determines a risk of cancer on the basis of defecation gas, the amount of odiferous gas is related with a time in which a stool is kept inside a body, so that acquisition of the defecation history information according to the present invention can be said as very useful means in enhancing diagnosis precision.

In the present invention, it is preferable that the test subject-side device further includes a stool state determination sensor that determines at least one of an amount of stool defecated by a test subject and a state of the stool, stool state information including at least one of the amount of stool and the state of the stool is recorded in the database, with the measurement data, and the stool state information as well as an analysis result is outputted to the server-side output device.

As the amount of stool is larger, the amount of defecation gas generally becomes larger, so that accurate analysis of physical condition can be performed. Further, it has been found in many inspections that when a stool is diarrhea, the frequency of defecation is high, and a generation amount of odiferous gas is reduced because an amount of water in the stools increases. According to the present invention of the above described configuration, diagnosis can be performed after at least one of the amount of stool and the state of the stool is taken into consideration, so that accurate diagnosis can be performed.

In the present invention, it is preferable that the test subject-side data analyzer further includes a reliability determination circuit that determines reliability of the first detection data outputted by the gas detector, and the test subject-side device does not transmit the measurement data to the server, when reliability determined by the reliability determination circuit is low.

According to the present invention of the above described configuration, transmission of the data with low reliability to the server can be omitted, so that useless transmission and reception of data and a load on the server can be reduced.

In the present invention, it is preferable that the test subject-side data analyzer analyzes physical condition of a test subject on the basis of the measurement data recorded in the database of the server.

According to the present invention of the above described configuration, it becomes unnecessary to provide a storage device for storing the measurement data in the test subject-side device, and the test subject-side device can be provided at a lower price.

In the present invention, it is preferable that the server configures new reference data to be a reference of analysis by the test subject-side data analyzer, on the basis of the measurement data accumulated and recorded in the database, and reference data of the test subject-side data analyzer is updated to the new reference data configured by the server.

It has been found in many inspections that there are individual differences in the amounts of odiferous gas containing a sulfur component and healthy-state gas, contained in defecation gas, and further, there are also individual differences according to a kind of meal and an amount of meal, an amount of exercise, age, sex and the like. If the reference data is fixed, it is difficult to reduce the influence of individual differences, and depending on the case, a test subject may be given useless anxiety, or given erroneous relief conversely. Meanwhile, on the server side, a lot of information gather, detailed analysis is performed, and a diagnosis result by a doctor, and the like can be obtained. According to the present invention of the above described configuration, the reference data in the test subject-side data analyzer is updated to the one which is optimally suited to the test subject from the result in the server, so that analysis in the test subject-side data analyzer can be easily updated to the reference data in which the influence of the individual differences is reduced, and thus, it becomes possible for a test subject to perform health management with confidence.

Advantageous Effect of Invention

According to the biological information measurement system of the present invention, the highly practical diagnosis system can be provided, which general consumers can readily purchase, prevents a user from being affected by a serious disease such as cancer by measurement of defecation gas at home, or can encourage a user in a less serious state to present to a hospital to undergo medical treatment, and is truly required by the market.

BRIEF DESCRIPTION OF THE DRAWINGS

FIG. 11 is a diagram showing an example of update of the diagnosis table.

DETAILED DESCRIPTION OF THE PREFERRED EMBODIMENTS

One embodiment of a biological information measurement system of the present invention will be described in detail below with reference to drawings.

Figure 1:
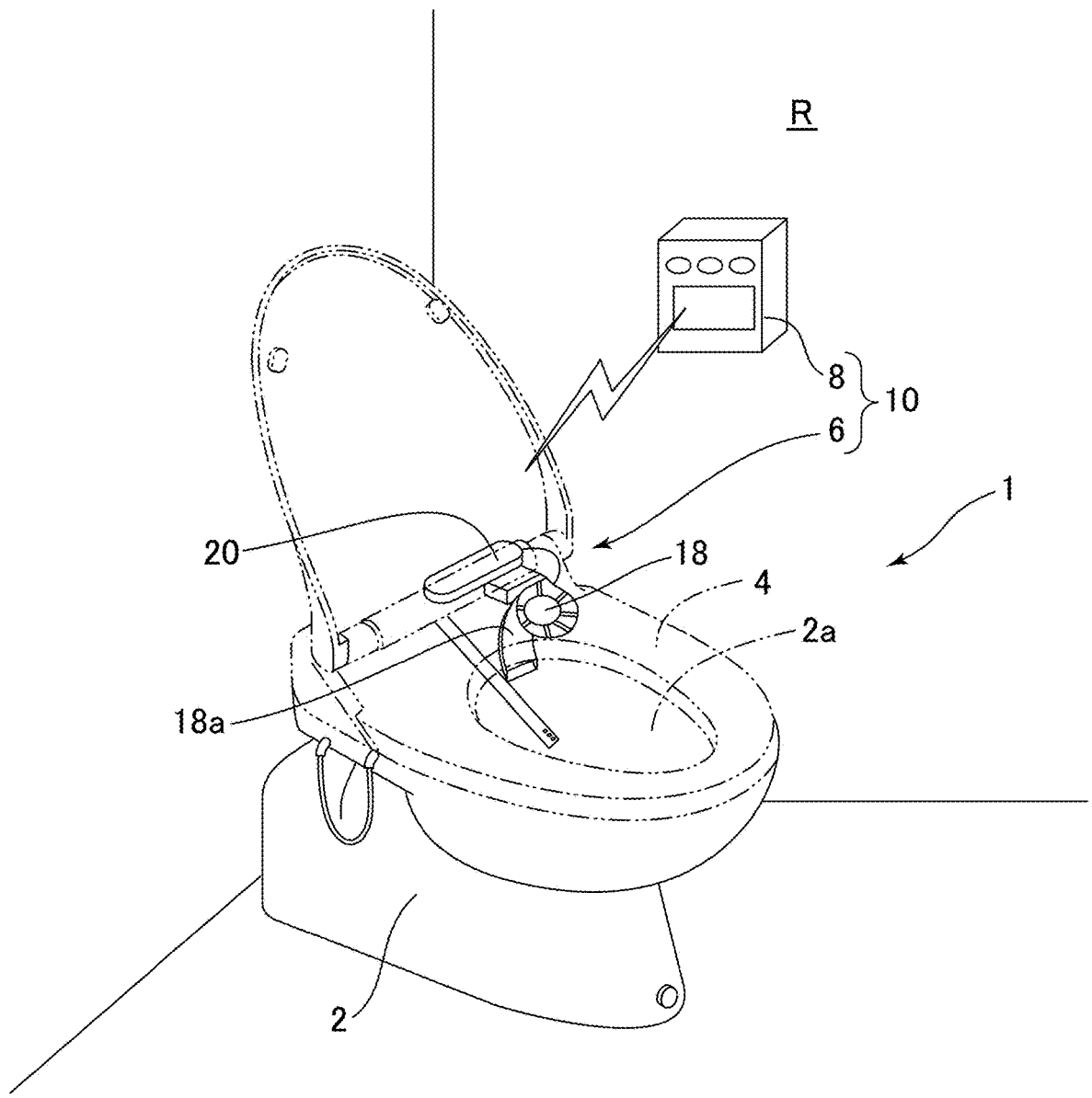
FIG. 1 shows a state in which a biological information measurement system in accordance with a first embodiment of the present invention is attached to a flush toilet installed in a toilet installation room.
Figure 2:
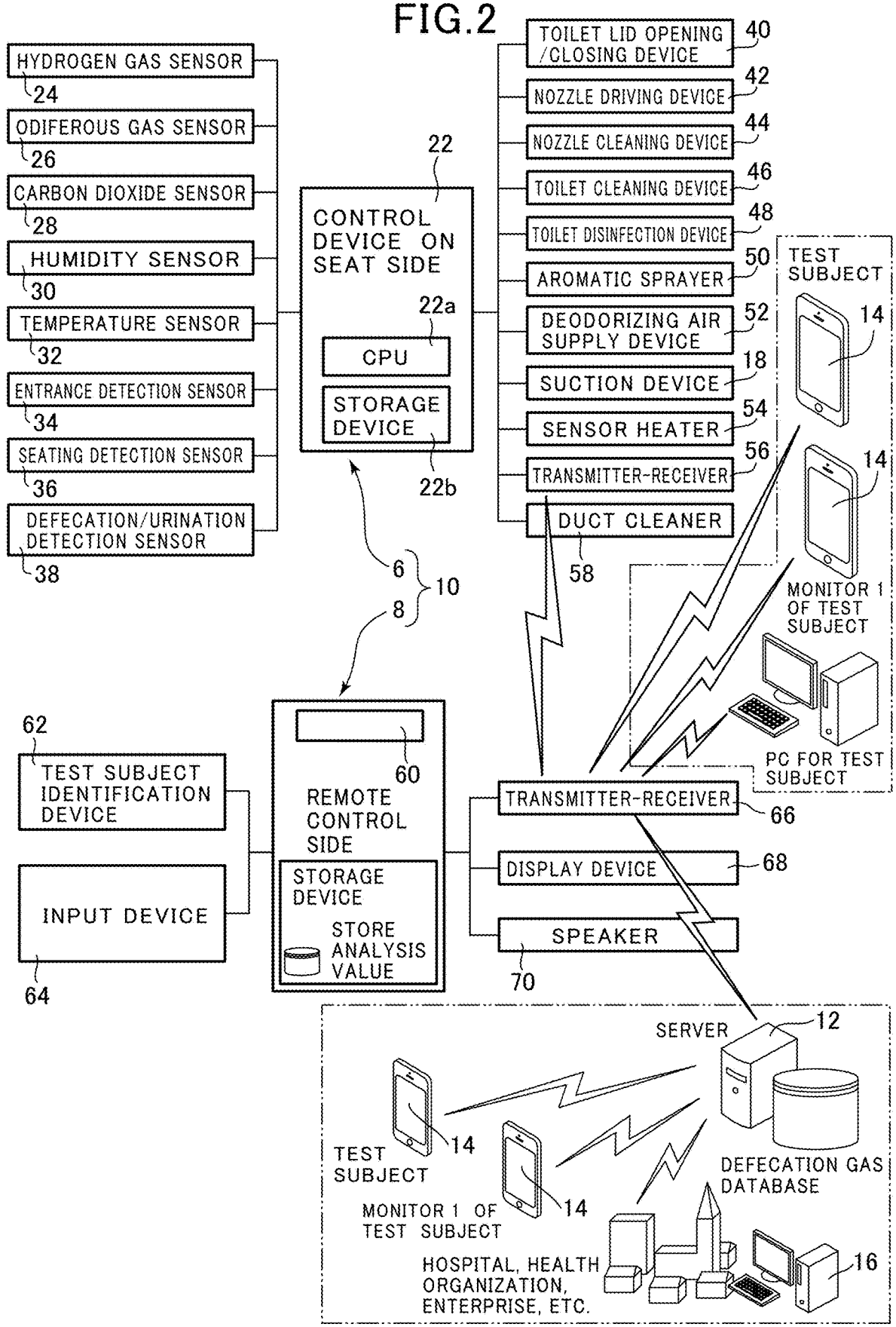
FIG. 2 is a block diagram showing a configuration of the biological information measurement system of the first embodiment of the present invention.
Figure 3:
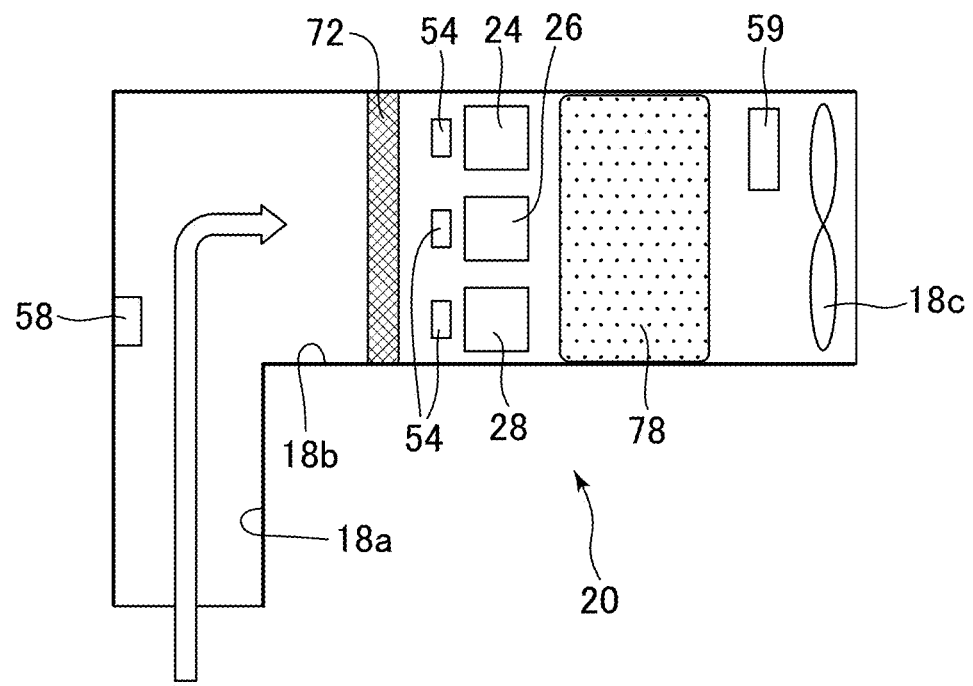
FIG. 3 shows a configuration of a gas detector provided in the biological information measurement system of the first embodiment of the present invention.

FIG. 1 shows a state in which a biological information measurement system in accordance with a first embodiment of the present invention is attached to a flush toilet installed in a toilet installation room. FIG. 2 is a block diagram showing a configuration of the biological information measurement system of the present embodiment. FIG. 3 shows a configuration of gas detector provided in the biological information measurement system of the present embodiment.

As shown in FIG. 1, the biological information measurement system 1 includes a measuring device 6 assembled inside a seat 4 mounted on a flush toilet 2 installed in a toilet installation room R, and a test subject-side device 10 composed of a remote control 8 attached to a wall surface of the toilet installation room R. In addition, as shown in FIG. 2, the biological information measurement system 1 includes a server 12, a terminal 14 for a test subject, formed by installing dedicated software in a smartphone, and the like, and a medical facility terminal 16 installed in medical facilities, such as a hospital, to exchange data with the test subject-side device 10 to serve as a part of the biological information measurement system 1. Further, measurement data transmitted from a large number of test subject side devices 10 is accumulated in the server 12 and the medical facility terminal 16, and then data analysis is performed.

The biological information measurement system 1 of the present embodiment analyzes physical condition including determination of cancer on the basis of odiferous gas containing a sulfur component, particularly a methyl mercaptan ($CH_3SH$) gas, in defecation gas discharged from a test subject during defecation. In addition, the biological information measurement system 1 of the present embodiment measures also healthy-state gas along with odiferous gas to improve analysis accuracy of physical condition on the basis of a correlation between the gases. The healthy-state gas originates from intestinal fermentation, and increases as an intestinal health degree increases. The healthy-state gas is specifically carbon dioxide, hydrogen, methane, short-chain fatty acid, and the like. In the present embodiment, a carbon dioxide gas and hydrogen gas, which are easy to be measured and are large in amount to enable reliability of measurement of a health index to be maintained at a high level, are measured as healthy-state gas. Each of the test subject-side devices 10 is configured to display an analysis result during defecation of a test subject or immediately after the defecation. In contrast, the server 12 collects measurement results of a large number of test subjects to enable more detailed analysis by comparison with another test subject, and the like. In this way, in the biological information measurement system 1 of the present embodiment, the test subject-side device 10 installed in the toilet installation room R performs a simple analysis, and the server 12 preforms a more detailed analysis.

Here, a measurement principle of physical condition in the biological information measurement system 1 of the present embodiment will be described.

Documents and the like report that if people have cancer of digestive system, particularly colorectal cancer, odiferous gas containing a sulfur component, such as methyl mercaptan or hydrogen sulfide, are discharged from an affected portion simultaneously with defecation. The digestive system includes the esophagus, stomach, duodenum, small intestine, large intestine, liver, the pancreas, and gallbladder. Although the large intestine also can be classified into the appendix, caecum, rectal, and colon, hereinafter the four portions are collectively called the large intestine. Cancer changes little on a daily basis, and gradually develops. If the cancer develops, the amount of odiferous gas containing a sulfur component, particularly methyl mercaptan, increases. That is, if the amount of odiferous gas containing a sulfur component increases, it can be determined that the cancer develops. In recent years, a concept of "ahead-disease" has spread, so that there is spread a concept of preventing a disease by improving physical condition at the time when the physical condition is deteriorated before falling sick.

Thus, it is required to detect cancer, particularly progressive cancer, such as colorectal cancer, before having cancer, to improve physical condition.

Here, defecation gas discharged during defecation includes nitrogen, oxygen, argon, water vapor, carbon dioxide, hydrogen, methane, acetic acid, trimethylamine, ammonia, propionic acid, methyl disulfide, methyl trisulfide, and the like, along with hydrogen sulfide and methyl mercaptan. Among them, it is required to measure odiferous gas containing a sulfur-based component, particularly methyl mercaptan to determine disease of cancer. Each of the propionic acid, methyl disulfide, and methyl trisulfide, contained in defecation gas, is a very trace amount as compared with the methyl mercaptan, so that each of them does not matter to analysis of physical condition, such as determination of cancer, whereby it is possible to ignore them. However, it cannot be said that each of other gas components is a negligible trace amount. In order to accurately determine cancer, it is generally thought to use a sensor capable of detecting only odiferous gas containing a sulfur component. Unfortunately, the sensor for detecting only odiferous gas containing a sulfur component is large in size and very expensive, so that it is difficult to be configured as an apparatus for household use.

In contrast, the present inventors have diligently studied to reach an idea that a gas sensor that detects not only methyl mercaptan in defecation gas, but also odiferous gas including another odiferous gas, is used to enable an apparatus for household use to be configured at low cost. Specifically, the present inventors determine to use a general semiconductor gas sensor or a solid electrolyte sensor, sensitive not only to a sulfur-containing gas containing a sulfur component, but also to another odiferous gas, as a sensor for detecting gas.

If a risk of cancer increases, a very strong odiferous gas containing a sulfur component, such as methyl mercaptan gas, increases in amount. Then, a sensor, such as a semiconductor gas sensor, and a solid electrolyte sensor, widely sensitive to odiferous gas, is capable of always detecting increase of this kind of gas. Unfortunately, as described later, a sensor, such as a semiconductor gas sensor, and a solid electrolyte sensor, widely sensitive to an odiferous gas, detects also another odiferous gas, such as hydrogen sulfide, methyl mercaptan, acetic acid, trimethylamine, or ammonia, which increases when people have poor physical condition caused by a bad living habit. However, cancer is a disease developing for a long time, or a few years, so that a state of having an increased very strong odiferous gas containing a sulfur component, such as methyl mercaptan gas or hydrogen sulfide, continues for a long time if people have cancer. Thus, even if a general semiconductor gas sensor, or a solid electrolyte sensor, widely sensitive not only to sulfur-containing gas containing a sulfur component, but also to another odiferous gas, is used, it is possible to determine that there is a high possibility of disease of cancer to cause a risk of cancer to increase if the amount of gas is high for a long time.

In addition, a semiconductor sensor and a solid electrolyte sensor, using an oxidation-reduction reaction, detect not only methyl mercaptan gas, but also odiferous gas, such as acetic acid, trimethylamine, or ammonia, in defecation gas. However, the present inventors have discovered from experimental results that a mixed amount of odiferous gas, such as hydrogen sulfide, methyl mercaptan, acetic acid, trimethylamine, or ammonia, tends to increase if a bad living habit causes physical condition to be deteriorated, and tends to decrease if physical condition is good. Specifically, healthy people have a small total amount of methyl mercaptan gas and odiferous gas other than the methyl mercaptan gas. In contrast, a total amount of methyl mercaptan gas and odiferous gas other than the methyl mercaptan gas temporarily increases due to deterioration of intestinal environment caused by excessive obstipation, a kind of meal, lack of sleep, crapulence, excessive drinking, excessive stress, and the like.

Acetic acid in defecation gas tends to increase not only when physical condition is deteriorated due to diarrhea, and the like, but also when physical condition is good. That is, this tendency does not always agree with tendency of the amount of methyl mercaptan and another odiferous gas with change in physical condition described above. However, the amount of acetic acid contained in defecation gas is very small as compared with methyl mercaptan. Thus, even if the amount of acetic acid increases when physical condition is good, the amount of the increase is very small as compared with decrease in the amount of another odiferous gas. In addition, the amount of increase of acetic acid when physical condition is deteriorated due to diarrhea, and the like, is very large as compared with the amount of increase thereof when physical condition is good. Accordingly, the amount of odiferous gas contained in defecation gas tends to increase as a whole if physical condition is deteriorated due to a bad living habit, and tends to decrease if physical condition is good. Then, deterioration of intestinal environment due to this kind of bad living habit results in having cancer, so that the amount of odiferous gas contained in defecation gas is a suitable index to improve physical condition when people are still in a state before having cancer.

In the present embodiment, physical condition is analyzed on the basis of detection data acquired by a semiconductor sensor, or solid electrolyte sensor, sensitive not only to methyl mercaptan gas, but also to odiferous gas other than the methyl mercaptan gas, such as hydrogen sulfide, acetic acid, trimethylamine, ammonia, in defecation gas. Accordingly, it is possible to acquire an analysis result to which a result of a wrong physical condition and a bad living habit is reflected, and the analysis result is available as an index based on objective data for improving physical condition and a living habit that may increase a risk of cancer.

In addition, defecation gas contains not only odiferous gas, but also $H_2$ and methane, so that if a semiconductor gas sensor, or a solid electrolyte sensor, is used for a gas sensor, the gas sensor also reacts to $H_2$ and methane. Further, if a measuring device using a semiconductor gas sensor, or a solid electrolyte sensor, is set at each home, the sensor may react to an aromatic and a perfume.

In contrast, the present inventors, as described later in detail, achieve a method of removing influence of hydrogen and methane from detection data of a semiconductor gas sensor, or a solid electrolyte sensor, by using a hydrogen sensor, a methane sensor, and a column, and a method of removing influence of an aromatic and a perfume as noise by detecting defecation act. Accordingly, influence of hydrogen and methane, as well as influence of an aromatic and a perfume, is removed from data detected by the semiconductor gas sensor, or the solid electrolyte sensor, to enable the amount of only odiferous gas in defecation gas to be estimated.

The amount of methyl mercaptan and another odiferous gas contained in defecation gas is very small as compared with $H_2$ and methane. Accordingly, even if a semiconductor gas sensor, or a solid electrolyte sensor, is used, the amount of the mixed odiferous gas may not be accurately measured.

In contrast, the present inventors have paid attention to that healthy people have acidic intestinal environment, and that cancer patients have intestinal environment in which odiferous gas containing a sulfur component occurs to increase in amount, so that the intestinal environment becomes alkaline to reduce bifidobacteria, and the like, in amount, whereby the amount of healthy-state gas of ferment-base components, such as $CO_2$, $H_2$, or fatty acid, reliably and continuously decreases inversely with increase of the amount of odiferous gas.

Accordingly, the inventors have thought that even if measurement accuracy at each measurement is not always high, monitoring a correlation between the amount of odiferous gas, such as methyl mercaptan and the amount of healthy-state gas components, such as $CO_2$, or $H_2$ during defecation every day may enable occurrence of advanced cancer to be detected.

Figure 41:
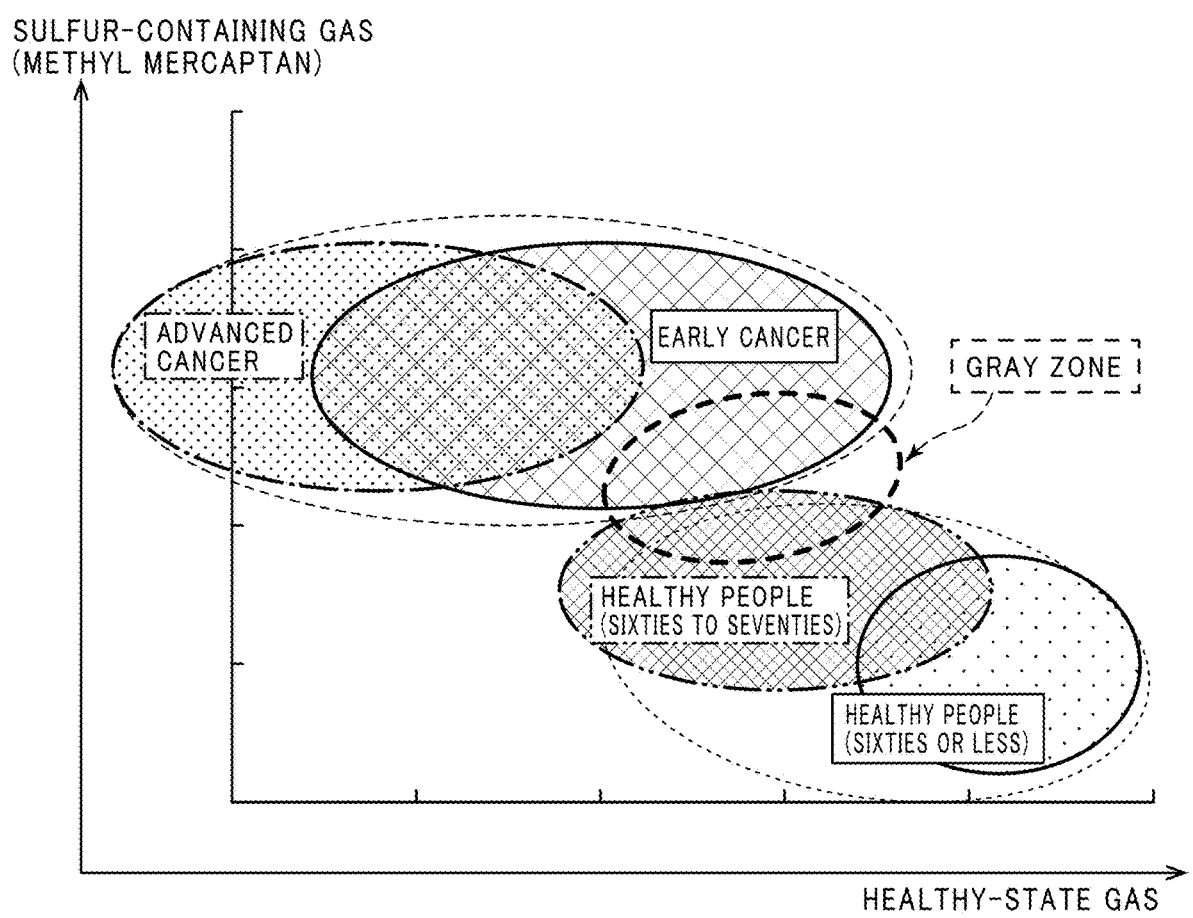
FIG. 41 is a diagram showing a result of measurement of the amounts of healthy-state gas and odiferous gas contained in defecation gas of each of healthy people less than sixties, healthy people in sixties to seventies, patients having early cancer, and patients having advanced cancer.

Then, the present inventors have measured the amount of healthy-state gas and odiferous gas contained in defecation gas acquired from each of healthy people less than sixties, healthy people in sixties to seventies, patients having early cancer, and patients having advanced cancer, and then a result shown in FIG. 41 has been acquired. That is, healthy people have defecation gas in which the amount of healthy-state gas is large, and the amount of odiferous gas is small. In contrast, cancer patients have defecation gas in which the amount of healthy-state gas is small, and the amount of odiferous gas is large. The amount of healthy-state gas contained in defecation gas in advanced cancer is less than that in early cancer. In addition, if the amount of healthy-state gas and the amount of odiferous gas is an intermediate amount between that of cancer patients and that of healthy people, the amount is within a gray zone, that is, it is thought that the gray zone is a state before having disease. Accordingly, the present inventors have thought on the basis of knowledge described above that if the amount of healthy-state gas of a test subject and the amount of odiferous gas, are measured, it is possible to improve determination accuracy of health condition on the basis of a correlation between the amounts.

In addition, FIGS. 42A to 48B show measurement data on the amount of various kinds of gas contained in defecation gas, in which healthy people and colorectal cancer patients (including advanced cancer, and early cancer) are compared.

Figure 42A:
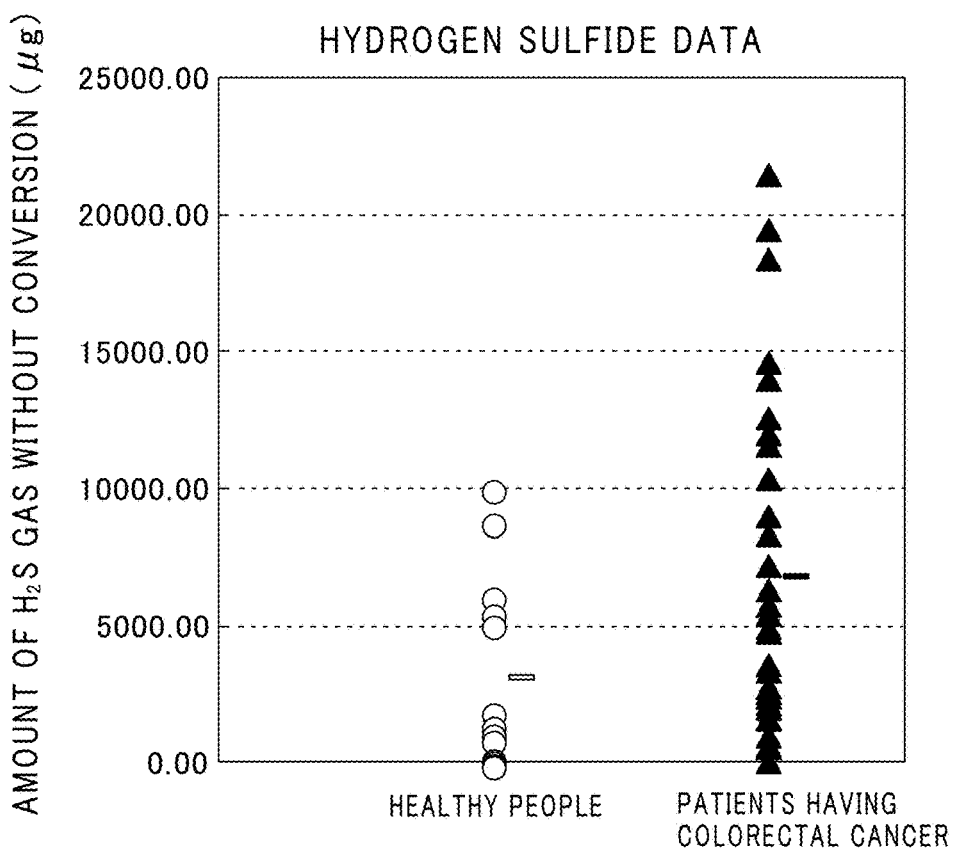
FIG. 42A is a diagram showing amounts of hydrogen sulfide gas contained in defecation gas before conversion, compared between healthy people and patients having colorectal cancer.
Figure 42B:
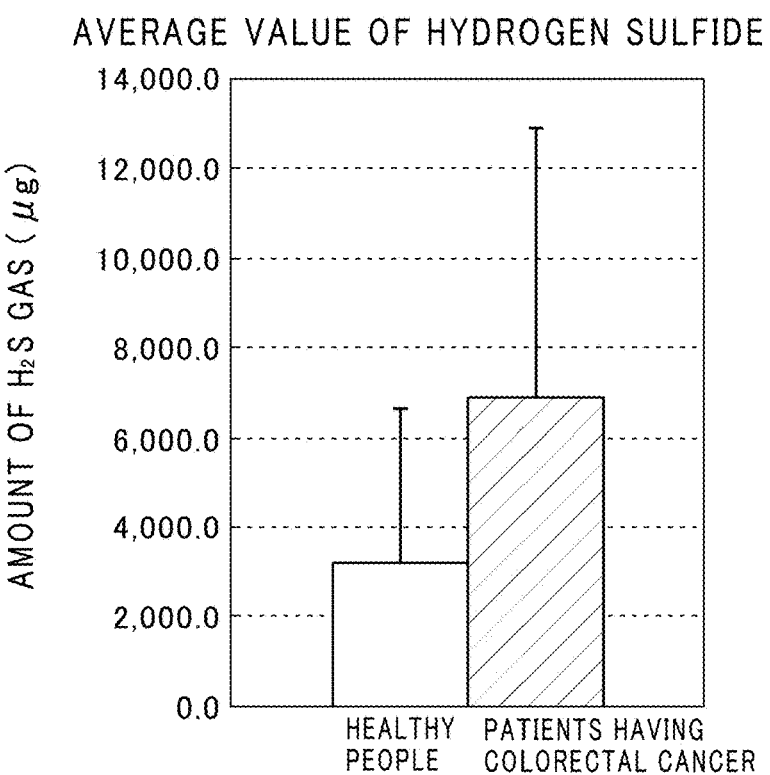
FIG. 42B is a diagram showing total amounts of hydrogen sulfide gas contained in defecation gas, compared between health people and patients having colorectal cancer.
Figure 43A:
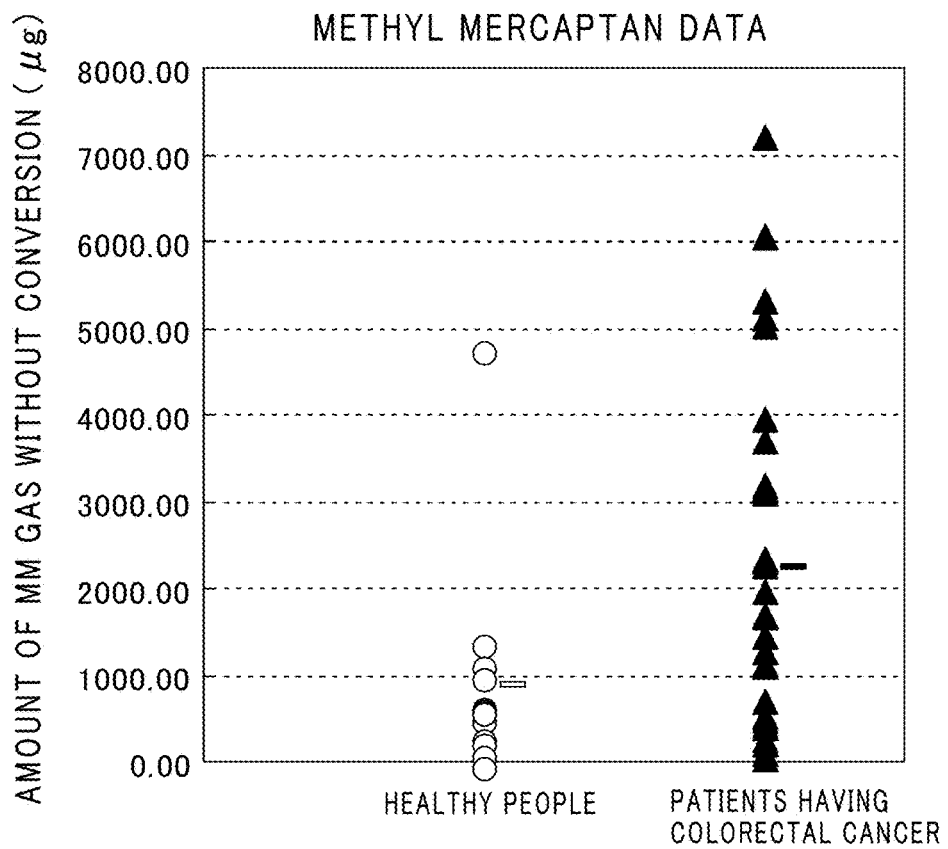
FIG. 43A is a diagram showing amounts of methyl mercaptan gas contained in defecation gas before conversion, compared between healthy people and patients having colorectal cancer.
Figure 43B:
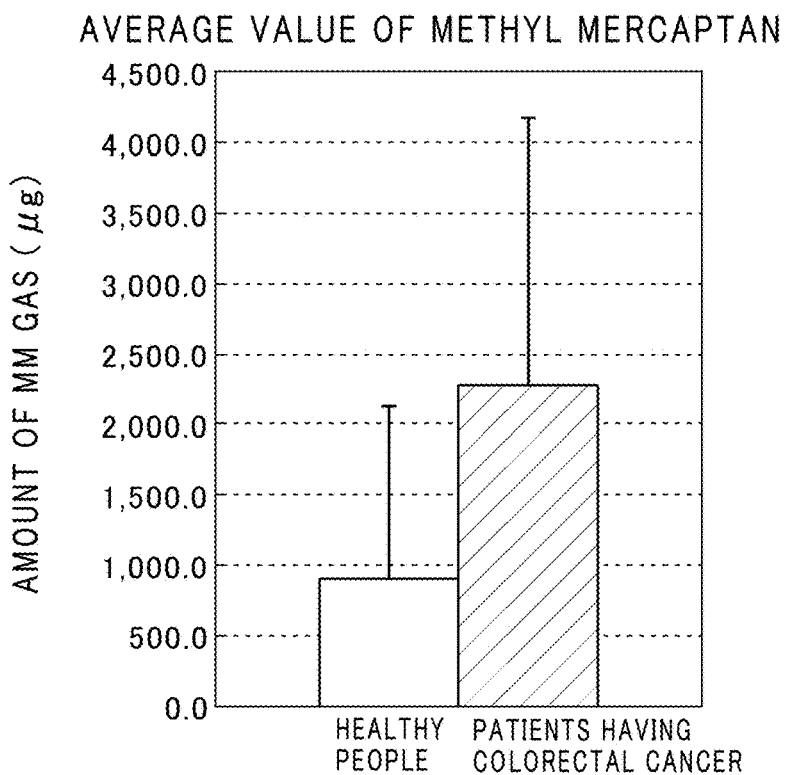
FIG. 43B is a diagram showing total amounts of methyl mercaptan gas contained in defecation gas, compared between healthy people and patients having colorectal cancer.
Figure 44A:
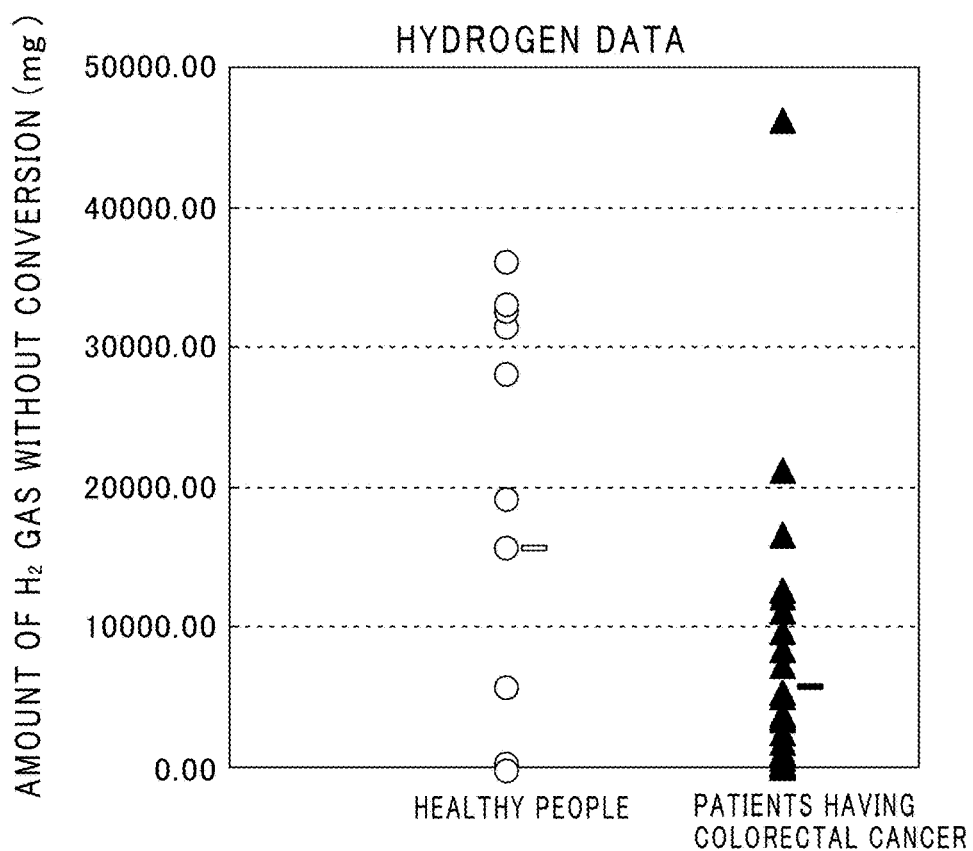
FIG. 44A is a diagram showing amounts of hydrogen gas contained in defecation gas before conversion, compared between healthy people and patients having colorectal cancer.
Figure 44B:
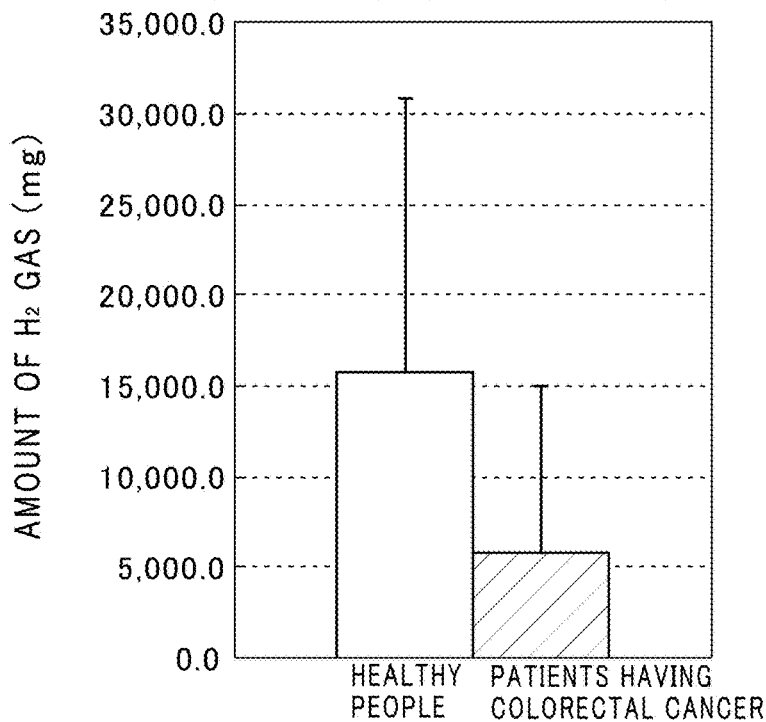
FIG. 44B is a diagram showing total amounts of hydrogen gas contained in defecation gas, compared between healthy people and patients having colorectal cancer.
Figure 45A:
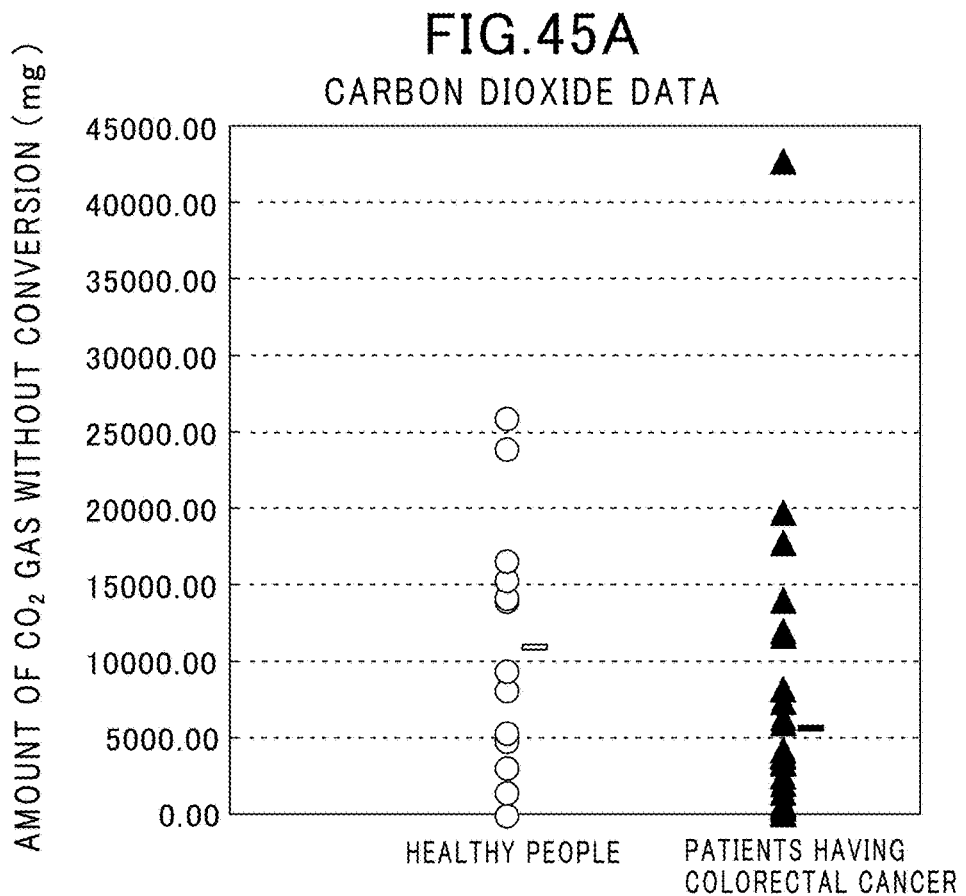
FIG. 45A is a diagram showing amounts of carbon dioxide gas contained in defecation gas before conversion, compared between healthy people and patients having colorectal cancer.
Figure 45B:
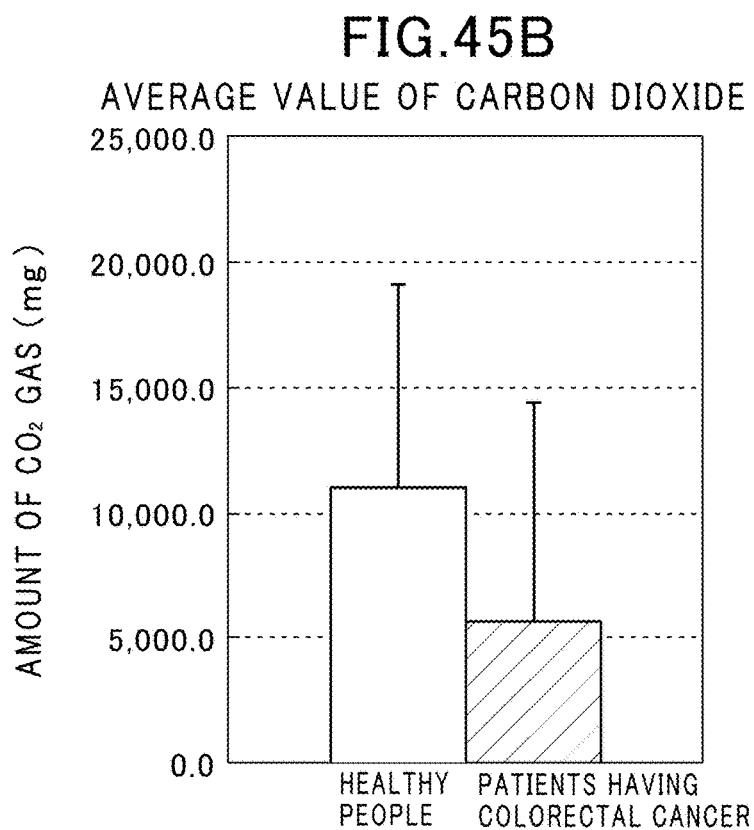
FIG. 45B is a diagram showing total amounts of carbon dioxide gas contained in defecation gas, compared between healthy people and patients having colorectal cancer.
Figure 46A:
FIG. 46A is a diagram showing amounts of propionic acid gas contained in defecation gas before conversion, compared between healthy people and patients having colorectal cancer.
Figure 46B:
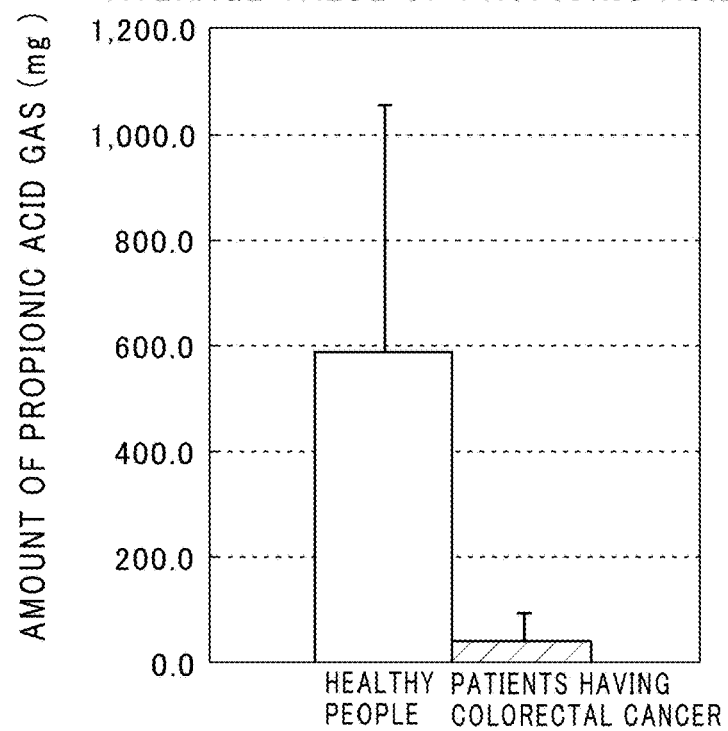
FIG. 46B is a diagram showing total amounts of propionic acid gas contained in defecation gas, compared between healthy people and patients having colorectal cancer.
Figure 47A:
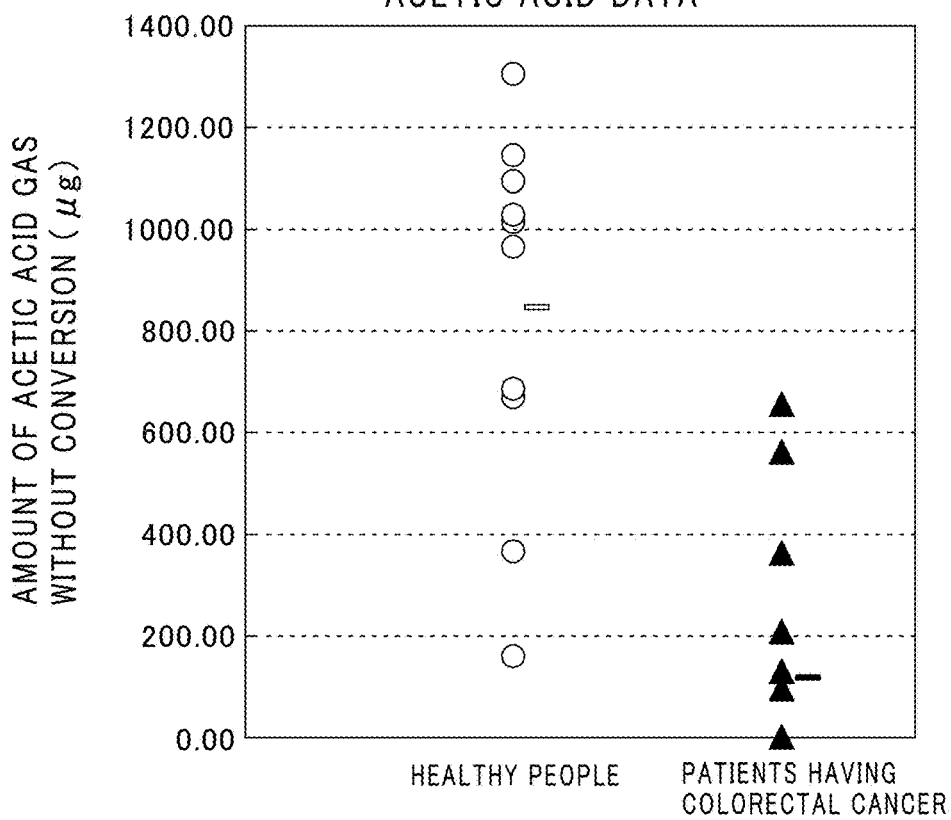
FIG. 47A is a diagram showing amounts of acetic acid gas contained in defecation gas before conversion, compared between healthy people and patients having colorectal cancer.
Figure 47B:
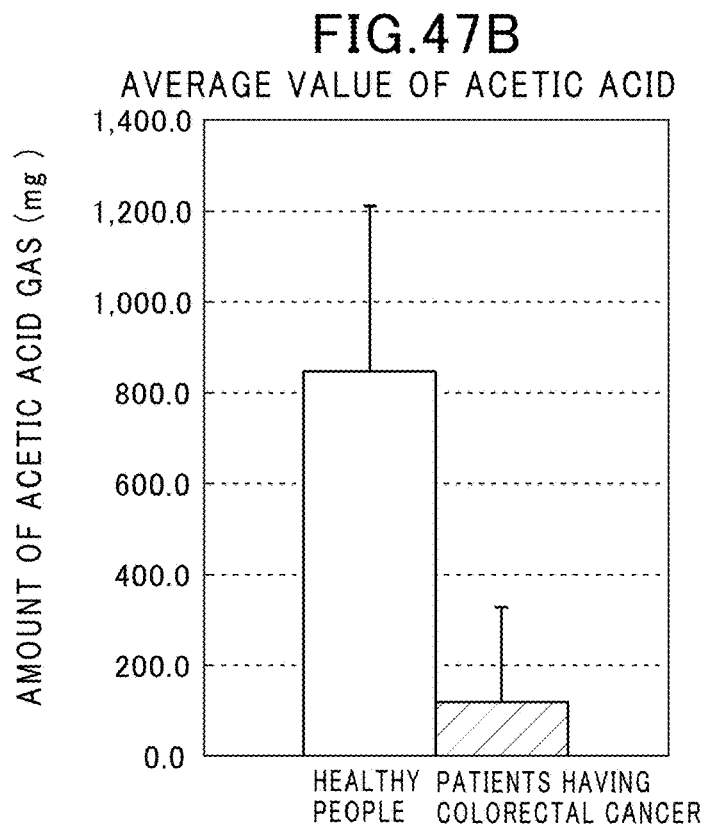
FIG. 47B is a diagram showing total amounts of acetic acid gas contained in defecation gas, compared between healthy people and patients having colorectal cancer.
Figure 48A:
FIG. 48A is a diagram showing amounts of butyric acid gas contained in defecation gas before conversion, compared between healthy people and patients having colorectal cancer.
Figure 48B:
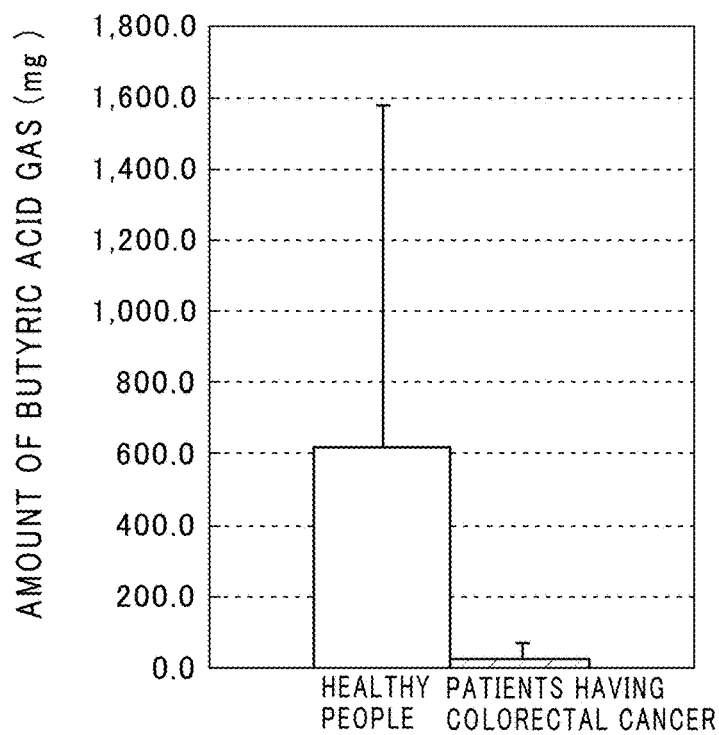
FIG. 48B is a diagram showing total amounts of butyric acid gas contained in defecation gas, compared between healthy people and patients having colorectal cancer.

FIG. 42 shows the amount of hydrogen sulfide contained in defecation gas, in which healthy people and colorectal cancer patients are compared, and FIGS. 43 to 48 show the amount of methyl mercaptan gas, hydrogen gas, carbon dioxide gas, propionic acid gas, acetic acid gas, and butyric acid gas, respectively, in each of which healthy people and colorectal cancer patients are compared. In each of FIGS. 43 to 48, a portion (A) shows measurement data on the amount of each gas by plotting healthy people with a circular mark, and colorectal cancer patients with a triangular mark. In addition, each of portions (B) shows an average value of each measurement data with a bar graph, and standard deviation of each of the measurement data with a line segment.

As is evident from the measurement data shown in FIGS. 42A to 48B, although the amount of various kinds of gas contained in defecation gas greatly varies in both healthy people and colorectal cancer patients, with respect to hydrogen sulfide gas and methyl mercaptan gas of odiferous gas, data indicating a large amount of gas is shown many times in the colorectal cancer patients, but there is little data indicating a large amount of gas in the healthy people. Meanwhile, with respect to hydrogen gas, and carbon dioxide gas, there is data indicating a large amount of gas in the healthy people, and there is little data indicating a large amount of gas in the colorectal cancer patients. In this way, while the amount of odiferous gas contained in defecation gas, indicating a risk of colorectal cancer, is large in the colorectal cancer patients, and small in the healthy people, the amount of hydrogen gas and carbon dioxide gas of healthy-state gas is large in the healthy people, and small in the colorectal cancer patient. Accordingly, magnitude relation between the amount of odiferous gas and the amount of healthy-state gas is reversed between the healthy people and the colorectal cancer patient. Although it is difficult to sufficiently measure physical condition of a test subject by using the measurement data acquired by one measurement of the amount of odiferous gas and healthy-state gas, the measurement data shows that if relation between odiferous gas and healthy-state gas is continuously measured multiple times for a predetermined period, it is possible to reliably measure physical condition of a test subject.

When measured defecation gas, the present inventors found that the amount of defecation gas discharged with the first excretory act was large, and a large amount of odiferous gas was also contained in a case where an excretory act was performed multiple times during one defecation (action of discharging a fart once or a stool once). Thus, in the present embodiment, health condition of a test subject is analyzed on the basis of defecation gas acquired first to accurately measure odiferous gas in trace amount. Accordingly, although measurement may be affected by a stool and a fart discharged by the first excretory act when the amount of gas discharged during the second excretory act or later is measured, this influence can be reduced.

The biological information measurement system 1 of the present embodiment is formed on the basis of the measurement principle described above. In the description below, odiferous gas includes methyl mercaptan gas of odiferous gas containing a sulfur component, and odiferous gas, such as hydrogen sulfide other than the methyl mercaptan, methyl mercaptan, acetic acid, trimethylamine, and ammonia.

Next, a specific configuration of the biological information measurement system 1 of the present embodiment will be described in detail.

As shown in FIG. 1, the test subject-side device 10 in the biological information measurement system 1 is attached to the flush toilet 2 in the toilet installation room R, and a part thereof is assembled into a seat 4 with a function of cleaning anus. The seat 4 with a function of cleaning anus is provided with a suction device 18 that sucks gas in a bowl 2a of the flush toilet 2, as the measuring device 6, and a gas detector 20 that detects a specific component of the gas sucked. The suction device 18 shares a part of a function with a deodorizing device that is usually assembled in the seat 4 with a function of cleaning anus. Gas sucked by the suction device 18 is deodorized by the deodorizing device, and then is returned into the bowl 2a. Each of devices assembled in the seat 4, such as the suction device 18, and the gas detector 20, is controlled by a built-in control device 22 provided on a seat side (refer to FIG. 2).

As shown in FIG. 2, the test subject-side device 10 is composed of the measuring device 6 assembled in the seat 4, and a data analyzer 60 built in the remote control 8.

The measuring device 6 includes a CPU 22a, and the control device 22 provided with a storage device 22b. The control device 22 is connected to a hydrogen gas sensor 24, an odiferous gas sensor 26, a carbon dioxide sensor 28, a humidity sensor 30, a temperature sensor 32, an entrance detection sensor 34, a seating detection sensor 36, a defecation/urination detection sensor 38, a toilet lid opening/closing device 40, a nozzle driving device 42, a nozzle cleaning device 44, a toilet cleaning device 46, a toilet disinfection device 48, an aromatic sprayer 50 of an aromatic injection device, a deodorizing air supply device 52, the suction device 18, a sensor heater 54, a transmitter-receiver 56, and a duct cleaner 58. As described later, the hydrogen gas sensor and the odiferous gas sensor may be formed into an integrated sensor.

The temperature sensor 32 measures temperature of a catalyst of the odiferous gas sensor 26, and the like. The humidity sensor 30 measures humidity of gas sucked from the inside of the bowl 2a. Sensitivity of these sensors slightly varies depending on temperature of the catalyst. Likewise, humidity change due to urination, and the like, affects sensitivity of the sensors. In the present embodiment, the amount of odiferous gas is very small in amount, so that the CPU 22a on a toilet side controls the sensor heater 54 described later, and a humidity adjuster 59 (refer to FIG. 3) to allow sensor temperature and suction humidity of the sensors 30 and 32 to be accurately maintained within a predetermined range, depending on temperature and humidity measured by the sensors 30 and 32, respectively. As a result, the sensor temperature and the suction humidity are adjusted to a predetermined temperature and humidity environment to enable gas in trace amount to be accurately and steady measured. These sensors and devices are not always required, and it is desirable to provide them to improve accuracy.

The entrance detection sensor 34 is an infrared ray sensor, for example, and detects entrance and leaving of a test subject into and from the toilet installation room R.

The seating detection sensor 36 is an infrared ray sensor, a pressure sensor, or the like, for example, and detects whether a test subject sits on the seat 4 or not.

In the present embodiment, the defecation/urination detection sensor 38 is composed of a microwave sensor, and is configured to detect a state of defecation, such as whether a test subject has discharged urine or a stool, whether a stool floats or sinks in seal water, and whether a stool is a diarrhea state or not. Alternatively, the defecation/urination detection sensor 38 may be composed of a CCD, and a water level sensor that measures transition of seal water.

The toilet lid opening/closing device 40 is provided to open and close a toilet lid on the basis of a detection signal of the entrance detection sensor 34, and the like, and according to a situation.

The nozzle driving device 42 is used to clean anus, and cleans anus of a test subject after defecation. The nozzle driving device 42 is configured to drive a nozzle to clean the flush toilet 2.

The nozzle cleaning device 44 cleans a nozzle of the nozzle driving device 42, and in the present embodiment, is configured to create hypochlorous acid from tap water to clean the nozzle with the hypochlorous acid created.

The toilet cleaning device 46 discharges water or tap water stored in a cleaning water tank (not shown) into a toilet to clean the inside of the bowl 2a of the flush toilet 2. Although the toilet cleaning device 46 is usually operated by a test subject while operating the remote control 8 to clean the inside of the bowl 2a, as described later, it is automatically operated by the control device 22 according to a situation.

The toilet disinfection device 48, for example, creates disinfecting water, such as hypochlorous acid water, from tap water, and sprays the disinfecting water created onto the bowl 2a of the flush toilet 2 to disinfect the bowl 2a.

The aromatic sprayer 50 sprays a predetermined aromatic into the toilet installation room R to prevent a test subject from spraying an arbitrary aromatic into the toilet installation room R to prevent an odor component that may be a disturbance with respect to measurement from being sprayed. Providing the aromatic sprayer 50 enables the predetermined aromatic in predetermined amount that does not affect measurement to be sprayed in a predetermined period according to a situation, and then the biological information measurement system 1 is able to recognize that the aromatic is sprayed. Accordingly, a disturbance with respect to measurement of physical condition is reduced to stabilize analysis results, so that the aromatic sprayer 50 serves as output result stabilizing means.

The suction device 18 is provided with a fan for sucking gas in the bowl 2a of the flush toilet 2, and the sucked gas is deodorized by a deodorant filter after flowing through a detecting portion of the odiferous gas sensor 26, and the like. Details of a configuration of the suction device 18 will be described later.

The deodorizing air supply device 52 discharges air that is deodorized after being sucked by suction device 18 into the bowl 2a.

The sensor heater 54 is provided to apply thermal activation to a catalyst of the odiferous gas sensor 26, and the like. Maintaining a catalyst at a predetermined temperature enables each sensor to accurately detect a predetermined gas component.

The duct cleaner 58 is provided to clean the inside of a duct 18a attached to the suction device 18 with hypochlorous acid acquired by electrolysis of tap water, or the like, for example.

In the present embodiment shown in FIG. 1, the suction device 18, the deodorizing air supply device 52, and the duct cleaner 58, are integrally formed into the deodorizing device. That is, the suction device 18 sucks gas in the bowl 2a into the duct 18a so that a deodorant filter 78 (refer to FIG. 3) applies deodorizing processing to the sucked gas, and then the gas to which the deodorizing processing is applied is discharged into the bowl 2a again. As a result, it is prevented that gas, to which the odiferous gas sensor 26 is sensitive, flows into the bowl 2a from the outside to change gas components in the bowl 2a during defecation of a test subject by a factor other than defecation gas discharged by the test subject. Thus, the deodorizing device provided with the deodorant filter 78, and the deodorizing air supply device 52, serve as output result stabilizing means. Alternatively, as a variation, the present invention may be configured to provide a gas supply device for measurement (not shown) that allows gas that is insensitive to each gas sensor to flow into the bowl 2a so as to allow gas for measurement with the same amount of gas sucked by the suction device 18 to flow into the bowl 2a. In this case, the gas supply device for measurement (not shown) serves as output result stabilizing means for stabilizing analysis results.

Next, as shown in FIG. 2, the remote control 8 is provided with the built-in data analyzer 60 to which a test subject identification device 62, an input device 64, a transmitter-receiver 66 which is a communication device, a display device 68, and a speaker 70, are connected. In the present embodiment, the transmitter-receiver 66, the display device 68, and the speaker 70, serve as an output device that outputs analysis results by the data analyzer 60. The data analyzer 60 is composed of a CPU, a storage device, a program for operating the CPU and the storage device, and the like, and the storage device is provided with a database.

In the present embodiment, the input device 64 and the display device 68 are configured as a touch panel to accept various kinds of input, such as identification information on a test subject, including a name of the test subject, and the like, as well as to display a variety of information items, such as measurement results of physical condition.

The speaker 70 is configured to output various kinds of alarm, message, and the like, issued by the biological information measurement system 1.

In the test subject identification device 62, identification information on a test subject, including a name of the test subject, and the like, is previously registered. When a test subject uses the biological information measurement system 1, names of registered test subjects are displayed in the touch panel, and then the test subject selects his or her own name.

The transmitter-receiver 66 on a remote control 8 side is communicatively connected to the server 12 through a network. The terminal 14 for a test subject is composed of a device capable of displaying data received by a smartphone, a tablet PC, a PC, or the like, for example.

The server 12 includes a defecation gas database. The defecation gas database records measurement data including the amount of odiferous gas and healthy-state gas in each excretory act, and reliability data, along with a measurement date and time, by being associated with identification information on each test subject using the biological information measurement system 1. The server 12 also stores a diagnosis table, and has data analysis means. The data analysis means on the server side is configured by an electric circuit built in the server 12.

In addition, the server 12 is connected to the medical facility terminal 16 installed in a hospital, a health organization, and the like, through a network. The medical facility terminal 16 is composed of a PC, for example, to enable data recorded in the database of the server 12 to be browsed. Input and output of information to and from the server 12 will be described later.

Subsequently, with reference to FIG. 3, a configuration of the gas detector 20 built in the seat 4 will be described.

First, in the biological information measurement system 1 of the present embodiment, a semiconductor gas sensor is used in the gas detector 20 as a gas sensor to detect odiferous gas and hydrogen gas. In addition, a solid electrolyte type sensor is used in the gas detector 20 to detect carbon dioxide.

The semiconductor gas sensor includes a catalyst composed of a metal oxide film containing tin oxide, and the like. If the catalyst is exposed to reducing gas while being heated at a few hundred degrees, oxidation-reduction reaction occurs between oxygen adsorbed on a surface of the catalyst and the reducing gas. The semiconductor gas sensor electrically detects change in resistance value of the catalyst by the oxidation-reduction reaction to enable reducing gas to be detected. Reducing gas that semiconductor gas sensor can detect includes hydrogen gas, and odiferous gas. In the present embodiment, although semiconductor gas sensors are used in both a sensor for detecting odiferous gas, and a sensor for detecting hydrogen gas, material components of each of catalysts of the respective sensors are adjusted so that a catalyst used in the odiferous gas sensor reacts strongly to odiferous gas, and a catalyst used in the hydrogen gas sensor reacts strongly to hydrogen gas.

In this way, although the present embodiment uses a "semiconductor gas sensor" as an "odiferous gas sensor", as described above, the "semiconductor gas sensor" is a general type that is sensitive not only to methyl mercaptan gas of a detection object, but also widely to odiferous gas other than that. In addition, as described later, although a solid electrolyte sensor is available for an "odiferous gas sensor", as with a semiconductor gas sensor, a general type of a solid electrolyte sensor, sensitive to methyl mercaptan gas as well as widely to another odiferous gas other than the methyl mercaptan, may be used. That is, it is very difficult to manufacture a gas sensor that is sensitive only to methyl mercaptan gas, and even if the gas sensor can be manufactured, the gas sensor becomes very large in size and expensive. If this kind of large and expensive gas sensor is used, the gas sensor is feasible for a medical device used in advanced clinical examination, but it is impossible to manufacture a biological information measurement system at a cost enabling the system to be sold as a consumer product. The biological information measurement system of the present embodiment uses a simple and general gas sensor that is sensitive also to another odiferous gas other than methyl mercaptan gas of a detection object, as the "odiferous gas sensor", to be feasible as a consumer product. As described above, although the gas sensor used in the present embodiment is sensitive to methyl mercaptan gas, as well as to odiferous gas other than the methyl mercaptan gas, the gas sensor is referred to as an "odiferous gas sensor" in the present specification, for convenience. The "odiferous gas sensor" used in the present embodiment is sensitive to odiferous gas that representatively includes methyl mercaptan gas, hydrogen sulfide gas, ammonia gas, and alcoholic gas.

Although the "odiferous gas sensor" used in the biological information measurement system 1 of the present embodiment is sensitive to methyl mercaptan gas of an object, as well as to odiferous gas other than that, a variety of devices described later enable even this kind of gas sensor to be used for measurement with necessary and sufficient accuracy as a consumer product. Specifically, the devices include a device to improve a measurement environment in a space of a toilet installation room where a variety of odiferous gases exist, a device for data processing of extracting data on defecation gas by assuming defecation act of a test subject from a detection signal provided by a gas sensor, a device to prevent an excessive mental burden from being applied to a test subject even if detection data with a large error is acquired, and the like. Each of the devices will be described later in detail.

Although the present embodiment describes a case where a semiconductor gas sensor is used for a sensor for detecting odiferous gas and hydrogen gas, a solid electrolyte sensor is also available instead of the semiconductor gas sensor. The solid electrolyte sensor, for example, detects gas on the basis of the amount of ions that penetrates its solid electrolyte, such as stabilized zirconia, while the solid electrolyte is heated. Gas which can be detected by the solid electrolyte sensor includes hydrogen gas, and odiferous gas. In the present embodiment, a solid electrolyte sensor is used as a sensor for detecting carbon dioxide. A carbon dioxide sensor is not limited to the above sensors, and an infrared sensor or the like may be available. The sensor for detecting carbon dioxide may be eliminated.

As shown in FIG. 3, in the present embodiment, the gas detector 20 is arranged inside the suction device 18.

The suction device 18 includes the duct 18*a* directed downward, an air intake passage 18*b* directed substantially in a horizontal direction, and a suction fan 18*c* arranged downstream of the air intake passage 18*b*. In the duct 18*a*, the duct cleaner 58, and the humidity adjuster 59, are provided.

The gas detector 20 includes a filter 72 arranged inside the air intake passage 18*b*, the odiferous gas sensor 26, the hydrogen gas sensor 24, and the carbon dioxide sensor 28. As shown in FIG. 3, the filter 72 is arranged so as to traverse the air intake passage 18*b*, and the odiferous gas sensor 26, the hydrogen gas sensor 24, and the carbon dioxide sensor 28, are juxtaposed downstream of the filter 72.

In addition, the deodorant filter 78 is provided downstream of the odiferous gas sensor 26, so that the suction device 18 also serves as a deodorizing device by allowing the deodorant filter 78 to deodorize sucked gas.

Further, the humidity adjuster 59 is provided downstream of the deodorant filter 78. The humidity adjuster 59 is filled with a desiccant, and if it is required to reduce humidity in the bowl 2*a*, moisture is removed from air circulating in the bowl 2*a* by switching a flow channel so that the air passing through the deodorant filter 78 passes through the filled desiccant. Accordingly, the humidity in the bowl 2*a* is maintained at a proper value to maintain detection sensitivity of each gas sensor at an almost constant level. Accordingly, the humidity adjuster 59 serves as output result stabilizing means that reduces a humidity variation in the bowl 2*a*.

The suction fan 18*c* sucks stink gas containing odiferous gas, and the like, in the bowl 2*a* of the flush toilet 2, at a constant speed to deodorize the stink gas, and then returns the gas into the bowl 2*a*. The duct 18*a* for deodorization opens in the bowl 2*a* while its suction port is directed downward to prevent a splash of urine or the like from entering the inside of the duct 18*a*. Molecular weight of odiferous gas, such as methyl mercaptan, and of hydrogen gas, is small enough to allow the gases to rise immediately after defecation. In contrast, in the present embodiment, odiferous gas and hydrogen gas discharged is sucked by suction fan 18*c* through an inlet of the duct 18*a*, opening in the bowl 2*a*, so that it is possible to reliably guide the gases into the gas detector 20. In this way, the suction device 18 is operated before a test subject starts defecation, and brings gas at a constant flow velocity into contact with each gas sensor during defecation of the test subject. Accordingly, it is possible to acquire a steady measurement value. Accordingly, the suction device 18 and the control device 22 that operates the suction device 18 serve as output result stabilizing means.

The filter 72 does not have a deodorizing function, and is configured so as to allow odiferous gas, hydrogen, and carbon dioxide to pass therethrough, as well as to prevent foreign material, such as urine, and a cleaner from passing therethrough. For this kind of filter 72, a member for mechanically collecting the foreign material without using chemical reaction, such as a fine net-like member, is available. Accordingly, it is possible to prevent the odiferous gas sensor 26, the hydrogen gas sensor 24, and the carbon dioxide sensor 28, from being contaminated by a urinary calculus, or the like.

The sensor heater 54 is provided upstream of each gas sensor, and downstream of the filter 72. As described above, the odiferous gas sensor 26 and the hydrogen gas sensor 24, each of which is a semiconductor gas sensor, are capable of detecting hydrogen and odiferous gases while each of their catalysts is heated to a predetermined temperature. The sensor heater 54 is provided to heat the catalysts of the odiferous gas sensor 26 and the hydrogen gas sensor 24. The carbon dioxide sensor 28 is also required to heat its solid electrolyte to a predetermined temperature, so that the sensor heater 54 is provided. The sensor heater 54 also serves as a stink removing device for thermally removing stink gas components attached to each of the sensors. Even if a solid electrolyte sensor is used as the odiferous gas sensor, and the hydrogen gas sensor, it is required to provide a sensor heater for heating a catalyst.

The sensor heater 54 also serves as means for removing a deposit attached to each sensor. Although foreign material is removed from gas passing through the filter 72, the sucked gas contains various stink gas components. Such stink gas components are attached to each gas sensor, and may cause noise when odiferous gas in trace amount is measured. In contrast, the sensor heater 54 heats a catalyst of a sensor to enable stink gas attached to the sensor to be thermally removed without providing an additional device. The control device 22 controls the sensor heater 54 before a test subject starts defecation act so as to allow temperature of each gas sensor to be constant. That is, the control device 22 controls the sensor heater 54 so as to prevent temperature of each gas sensor from decreasing due to contact of an air flow. Accordingly, it is possible to maintain sensitivity of each gas sensor at a predetermined value during defecation of a test subject to enable a measurement error of each gas sensor to be reduced. Accordingly, the control device 22 and the sensor heater 54 serve as output result stabilizing means that stabilizes an analysis result which is outputted.

The deodorant filter 78 is a catalytic filter that adsorbs stink gas, such as odiferous gas. The deodorant filter 78 removes gas, such as odiferous gas, from air, and the air is returned to the bowl 2a. Then, if odiferous gas or the like is contained in the gas returned into the bowl 2a, the odiferous gas or the like flows into the bowl 2a may be sucked through the duct 18a again to be detected by the odiferous gas sensor 26 again. Thus, in the present embodiment, the deodorant filter 78 is arranged downstream of the odiferous gas sensor 26 to reliably remove odor components, such as odiferous gas, from gas returned into the bowl 2a.

If a test subject sits on the seat 4, a portion above the bowl 2a is closed by his or her underwear, or the like. If the inside of the bowl 2a is placed under negative pressure, stink gas components attached to a body, clothes, and the like, of the test subject, may be sucked into the bowl 2a. In the biological information measurement system 1 of the present embodiment, sensitivity of the odiferous gas sensor 26 is set very high to detect only a trace amount of odiferous gas contained in defecation gas, so that even stink gas components attached to a body, clothes, and the like, of a test subject, may be a disturbance with respect to measurement. In contrast, in the present embodiment, gas after deodorized is returned into the bowl 2a, so that the inside of the bowl 2a is not placed under negative pressure to enable gas components attached to a body, clothes, and the like, of a test subject, to be prevented from being sucked into the bowl 2a.

Here, the semiconductor gas sensor used as the odiferous gas sensor 26 detects not only odiferous gas but also hydrogen. Thus, it is required to separate influence of hydrogen gas from detection data acquired by the semiconductor gas sensor. In the present embodiment, as a hydrogen separation mechanism for separating this kind of influence of hydrogen gas, in the gas detector 20, a detection value of hydrogen gas detected by the hydrogen gas sensor 24 is subtracted from a detection value of odiferous gas detected by the semiconductor gas sensor to separate influence of hydrogen gas so that the calculated value is outputted as a detection value of the odiferous gas sensor 26. A configuration that is composed of this kind of hydrogen separation mechanism, the semiconductor gas sensor, and the hydrogen gas sensor 24, to output a detection value corresponding to the amount of odiferous gas and hydrogen gas, is referred to as a detection value output mechanism. Calculation processing of subtracting a detection value of hydrogen gas detected by the hydrogen gas sensor 24 from a detection value of odiferous gas detected by the semiconductor gas sensor described above may be performed in the data analyzer 60, or the like. Although the present embodiment describes the hydrogen separation mechanism for separating influence of hydrogen gas from detection data acquired by the semiconductor gas sensor, it is also possible to separate influence of methane from detection data acquired by the semiconductor gas sensor by providing a methane sensor for detecting methane. A semiconductor gas sensor with a catalyst composed of material components adjusted so as to strongly react to methane may be used as the methane gas sensor.

Many people have no methane producer that produces methane in their intestine, or have very low amount thereof if existing, so that many people have a very low amount of methane contained in defecation gas. Thus, in the present embodiment, the hydrogen sensor 24 and the carbon dioxide sensor 26 are provided as a healthy-state gas sensor. However, a few people have a very large amount of methane producer in their intestines. Defecation gas of people having a very large amount of intestinal methane producer as described above contains a large amount of produced methane, but contains a low amount of produced hydrogen. Thus, if only the hydrogen sensor 24 and the carbon dioxide sensor 26 are provided, defecation gas of people having a very large amount of intestinal methane producer is unfavorably determined that there is a small amount of discharged healthy-state gas. In the present embodiment, although the hydrogen sensor 24 and the carbon dioxide sensor 26 are provided as a healthy-state gas sensor to fit with many people, a methane gas sensor instead of the hydrogen sensor 24 may be provided to fit with people having a large amount of methane gas. In addition, it is more preferable to provide the methane gas sensor in addition to the hydrogen sensor 24 and the carbon dioxide sensor 26 in advance to be able to correspond to any test subject.

As described above, defecation gas contains a large amount of hydrogen, and the semiconductor gas sensor detects not only odiferous gas but also hydrogen. For that, influence of hydrogen can be separated by subtracting the amount of hydrogen gas detected by the hydrogen gas sensor 24 from the amount of gas detected by the odiferous gas sensor 26 of a semiconductor gas sensor, so that it is possible to accurately measure the amount of odiferous gas.

In addition, hydrogen gas contained in defecation gas has very small molecular weight as compared with air to be easily released from the bowl 2a. For that, in the present embodiment, defecation gas is sucked by the fan 18c of the suction device 18 to enable defecation gas containing hydrogen gas to be reliably collected.

If sucked defecation gas is returned into the bowl 2a as it is, measurement accuracy by the odiferous gas sensor 26 decreases. In contrast, in the present embodiment, sucked defecation gas is deodorized by the deodorant filter 78 to be returned into the bowl to enable the amount of odiferous gas and hydrogen to be accurately measured. In addition, although the deodorant filter 78 as above is required to be arranged downstream of each sensor, if the deodorant filter 78 as above is provided downstream of each sensor, the sensor may be directly contaminated by foreign material. In contrast, in the present embodiment, the filter 72 without a deodorizing function is provided upstream of a sensor to enable contamination of the sensor by foreign material to be reduced without affecting measurement of odor components.

If gas is sucked into the bowl 2a, pressure in the bowl 2a decreases, and thus stink gas components attached to a body and clothes of a test subject may flow into the bowl 2a. In contrast, in the present embodiment, air after odor components have been deodorized is returned into the bowl 2a, so that stink gas components attached to a body and clothes of a test subject are prevented from flowing into the bowl 2a to enable accurate measurement.

A configuration in which air after being deodorized to remove odor components is returned into the bowl 2a is not essential. If the configuration in which air after being deodorized to remove odor components is returned into the bowl 2a is not adopted, stink gas components attached to the body and clothes of a test subject may flow into the bowl 2a. However, as described later with reference to FIG. 9, at the time of setting a reference value of residual gas, the reference value of the residual gas is set after the influence of the stink gas components attached to the body and clothes of the test subject is included. Consequently, it is possible to estimate the amount of gas without returning air after being deodorized to remove odor components into the bowl 2a.

Next, with reference to FIGS. 4 and 5, a flow of measurement of physical condition by the biological information measurement system 1 in accordance with the first embodiment of the present invention will be described.

Figure 4:
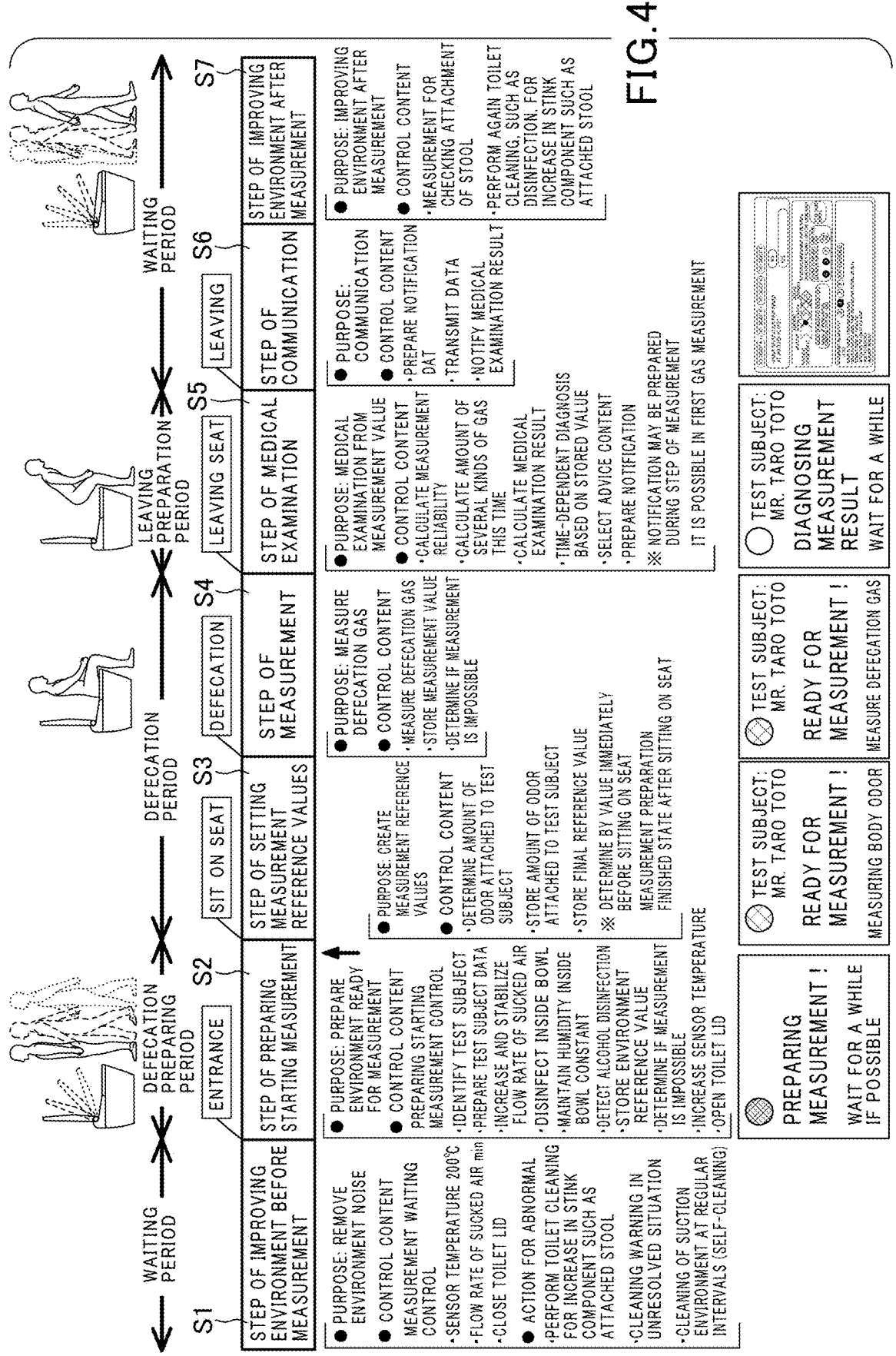
FIG. 4 is a diagram explaining a flow of measurement of physical condition by the biological information measurement system of the first embodiment of the present invention.

FIG. 4 describes a flow of measurement of physical condition, and an upper section shows each step of the measurement of physical condition, as well as a lower section shows an example of screens to be displayed in a display device of a remote control in each step. FIG. 5 shows an example of the screens to be displayed in the display device of the remote control.

The biological information measurement system 1 of the present embodiment analyzes physical condition including determination of cancer on the basis of a correlation between odiferous gas and healthy-state gas, in defecation gas discharged by a test subject during defecation. In each test subject-side device, it is preferable that an analysis result is displayed during defecation, or in a short time until leaving a toilet installation room after one defecation period has been finished. However, if analysis is performed in a short time, analysis accuracy may decrease. It is difficult that the suction device 18 sucks the whole of defecation gas discharged by a test subject, and a condition where the inside of a toilet or a toilet installation room is very unsanitary, or a measurement environment with a strong aromatic, becomes a disturbance that affects measurement accuracy so that it may decrease. Thus, when physical condition including whether there is a disease or not is notified to a test subject in each test subject-side device, in consideration of a mental burden of the test subject, it is devised that not only an absolute amount of odiferous gas having a strong relationship with cancer, but also change in physical condition of a test subject, or change in intestinal conditions, is strongly notified to the test subject, on the basis of time-dependent results acquired by measurement performed during defecation act performed many times for a long time. In addition, also in consideration of a measurement error during each defecation act, in the present embodiment, it is devised that physical condition is notified to a test subject on the basis of measurement results during one defecation act so that the physical condition to be notified to the test subject does not largely changes. The device is based on using characteristics of disease of cancer that develops for a long time, because if the amount of odiferous gas having a strong relationship with cancer is largely changed for a short time, it is not caused by a strong relationship with cancer, but largely caused by a result of a bad living habit or influence of noise, whereby a large change in physical condition may apply unnecessary mental anxiety to the test subject.

In the light of the above matter, in the present embodiment, the test subject-side device 10 simply analyzes health condition on the basis of measurement results of defecation gas discharged first in one defecation act, or defecation gas discharged during the first excretory act to display an analysis result of the health condition. In contrast, the server 12 is capable of a detailed analysis on the basis of a total amount of gas discharged during one defecation act by comparing it with that of other test subjects, and the like. Then, in the biological information measurement system 1 of the present embodiment, the test subject-side device 10 installed in the toilet installation room R performs a simple analysis, and the server 12 performs a more detailed analysis.

As shown in FIG. 4, in measurement during one defecation act by the biological information measurement system 1 of the present embodiment, the following steps is performed: step S1 of improving environment before measurement; step S2 of preparing starting measurement; step S3 of setting measurement reference values; step S4 of measurement; step S5 of medical examination; step S6 of communication; and step S7 of improving environment after measurement.

Step S1 of improving environment before measurement is performed before a test subject enters the toilet installation room R. The entrance detection sensor 34 (refer to FIG. 2) detects whether a test subject enters the toilet installation room R, or not.

In step S1 of improving environment before measurement, the control device 22 on a seat side allows the sensor heater 54, the suction device 18, and the toilet lid opening/closing device 40, to switch to a measurement waiting mode to control them. The sensor heater 54 is controlled in the measurement waiting mode on the basis of temperature measured by the temperature sensor 32 so that temperature of the catalyst of the odiferous gas sensor 26 becomes temperature (370° C., for example) lower than temperature when measurement is performed. The suction device 18 is controlled in the measurement waiting mode so that a flow rate of sucked air becomes minimum. The toilet lid opening/closing device 40 is controlled in the measurement waiting mode so that a toilet lid is closed.

In step S1 of improving environment before measurement, although the catalyst of the odiferous gas sensor 26 is at a temperature lower than an optimum temperature because the sensor heater 54 is in the measurement waiting mode, it is possible to measure concentration of odiferous gas. If there is an occurrence source of stink gas in the bowl 2a, such as a case where there is a stool attached to the flush toilet 2, or the like, concentration of gas measured by the odiferous gas sensor 26 becomes a predetermined value or more. The control device 22 allows toilet cleaning to be performed if the concentration of gas measured by the odiferous gas sensor 26 exceeds a predetermined value in step S1 of improving environment before measurement. Specifically, the control device 22 performs as follows: allows the nozzle driving device 42 to discharge cleaning water through a nozzle to clean the bowl 2a; allows the toilet cleaning device 46 to discharge water stored in a cleaning water tank into the bowl 2a to clean the inside of the bowl 2a; or allows the toilet disinfection device 48 to create disinfecting water, such as hypochlorous acid water, from tap water, or the like to spray disinfecting water created onto the bowl 2a to disinfect the bowl 2a.

If the concentration of gas measured by the odiferous gas sensor 26 is a predetermined value or more, the control device 22 also enables the suction device 18 to discharge gas in the bowl 2a to reduce concentration of gas. Gas sucked by the suction device 18 is deodorized by the deodorant filter 78, so that the suction device 18 and the deodorant filter 78 serve as a deodorizing device. The suction device 18 sucks gas while the toilet lid is opened to enable not only the inside of the bowl 2a but also the inside of the toilet installation room R to be deodorized, so that the suction device 18 and the deodorant filter 78 can also serve as a toilet installation room deodorizing device. Preferably, if the suction device 18 and the deodorant filter 78 serve as a deodorizing device, the amount of gas to be sucked by the suction device 18 is increased as compared with when measurement of physical condition is performed during defecation of a test subject.

Alternatively, the control device 22 may be configured so as to be able to control a ventilator (not shown) provided in the toilet installation room R to allow the ventilator to operate to reduce concentration of gas. In this way, concentration of odiferous gas remaining in the bowl 2a is reduced to reduce influence of residual gas noise caused by the gas remaining. Accordingly, cleaning or disinfection of the bowl 2a by the nozzle driving device 42, the toilet cleaning device 46 or the toilet disinfection device 48, and exhaust/deodorization in the bowl 2a or in the toilet installation room R that are performed in step S1 of improving environment before measurement serve as noise responding means that reduces influence of residual gas noise, and residual gas removing means that reduces concentration of remaining odiferous gas. Further, noise responding means that is carried out at a time except for a defecation period of a test subject when the test subject is not in the toilet installation room R serves as first noise responding means and serves as residual gas removing means.

In step S1 of improving environment before measurement, if the amount of gas measured by the odiferous gas sensor 26 is not less than a predetermined value even if the toilet cleaning described above is performed, the control device 22 allows the transmitter-receiver 56 to transmit a cleaning warning command signal. When the transmitter-receiver 66 on the remote control 8 side receives the cleaning warning command signal, the display device 68 or the speaker 70 notifies a test subject that toilet cleaning should be performed.

In addition, in step S1 of improving environment before measurement, the control device 22 allows cleaning of suction environment to be performed at regular intervals. Specifically, the control device 22 allows the duct cleaner 58 to operate to spray cleaning water into the duct 18a of the suction device 18 to clean the duct 18a, and the like. Further, the sensor heater 54 heats each of the hydrogen gas sensor 24, the odiferous gas sensor 26, and the carbon dioxide sensor 28, to a high temperature to burn stink gas components attached to a surface of each of the gas sensors 24, 26, and 28.

Next, when the entrance detection sensor 34 detects entrance of a test subject, the control device 22 transmits a signal of starting step S2 of preparing starting measurement to the transmitter-receiver 66 on the remote control 8 side through the transmitter-receiver 56, and then step S2 of preparing starting measurement is performed in synchronization with the remote control side.

In step S2 of preparing starting measurement, first, the test subject identification device 62 built in the remote control 8 identifies a test subject. Specifically, in the biological information measurement system 1, a resident of a house in which the system is installed is registered, and a registered resident is displayed as a candidate of the test subject. That is, as shown in FIG. 5, buttons of respective candidates, such as a "test subject A", a "test subject B", and a "test subject C", are displayed in an upper portion of the display device 68 of the remote control 8, and then a test subject entering the toilet installation room R presses a button corresponding to oneself to identify the test subject. In addition, the data analyzer 60 built in the remote control 8, with reference to data in a storage device, acquires previous measurement data on personal identification information received by the test subject identification device 62, and a physical condition display table as reference data to be a basis of analysis.

Figure 5:
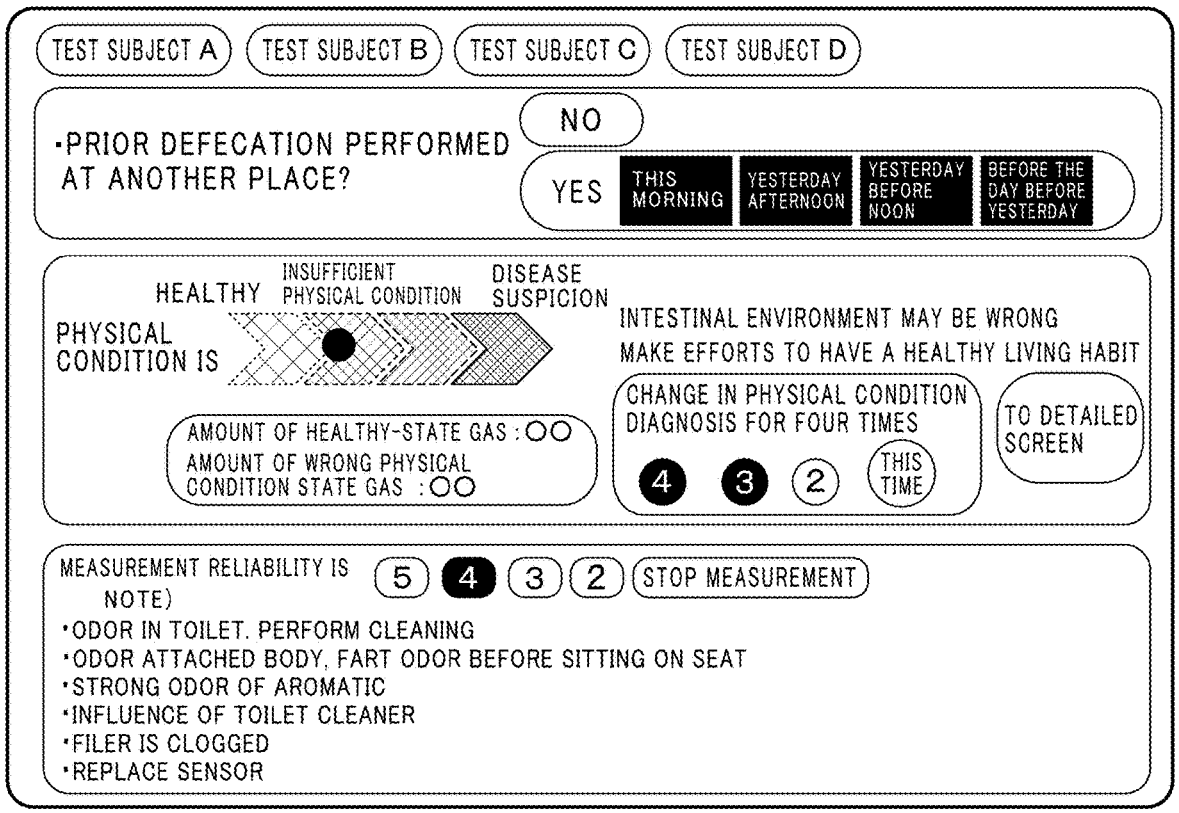
FIG. 5 is a diagram showing an example of a screen displayed in a display device of a remote control provided in the biological information measurement system of the first embodiment of the present invention.

In addition, in step S2 of preparing starting measurement, the data analyzer 60, as shown in FIG. 5, allows a display device to display a message in a second section of its screen, such as: a question about whether previous defecation was performed in the toilet installation room in which this device is installed, such as "Was previous defecation performed in another place?"; and options of answers to the question, such as "Yes (This morning)", "Yes (Yesterday afternoon)", "Yes (Yesterday before noon)", "Before the day before yesterday", and "No". Once a test subject answers these questions, the input device 64 of the data analyzer 60 receives defecation history information on the test subject. This kind of defecation history information on elapsed time from previous defecation act of a test subject is stored in a storage device (test subject information storage device) built in the remote control 8, and the test subject information storage device also stores information on a test subject previously registered, such as weight, age, and sex. The defecation history information is transmitted to the server 12 to be recorded in a database of the server 12.

In step S2 of preparing starting measurement, the control device 22 on a toilet side allows the sensor heater 54, the suction device 18, and the toilet lid opening/closing device 40 to switch to a measurement mode. The sensor heater 54 is controlled in the measurement mode on the basis of temperature measured by the temperature sensor 32 so that temperature of the catalyst of the odiferous gas sensor 26 becomes a temperature (400° C.) suitable for measurement. The suction device 18 is controlled in the measurement mode so that a flow rate of sucked air is increased to the extent that defecation gas does not leak to the outside of the bowl 2a to be constantly maintained at the extent so as not to vary. The toilet lid opening/closing device 40 is controlled in the measurement mode so that a toilet lid is opened.

If concentration of odiferous gas detected by the odiferous gas sensor 26 is high in step S2 of preparing starting measurement, the control device 22 allows the toilet disinfection device 48 to disinfect the inside of the bowl 2a.

In step S2 of preparing starting measurement, if humidity measured by the humidity sensor 30 is unsuitable for measurement of defecation gas by the odiferous gas sensor 26, the control device 22 transmits a signal to the humidity adjuster 59 to control it so that humidity in the bowl becomes a proper value.

In the step of preparing starting measurement, when the seat 4 is cleaned with a sheet or spraying, by using alcoholic disinfectant, the odiferous gas sensor 26 reacts to alcohol to suddenly increase concentration of gas. In this way, if concentration of gas measured by the odiferous gas sensor 26 suddenly increases, the data analyzer 60 allows the display device 68 to display a warning.

The data analyzer 60 stores a measurement value measured by the odiferous gas sensor 26, as an environment reference value of a noise level to be a basis of measurement of defecation gas. The data analyzer 60 then determines whether the measurement of defecation gas is possible or not on the basis of the environment reference value. If the data analyzer 60 determines that measurement of a noise level being performed, or the measurement of defecation gas is impossible, the display device 68 is allowed to display a message, such as "During measurement preparation. Wait for a while if possible", as shown in a lower section of FIG. 4, to urge a test subject to wait for defecation.

Next, when the seating detection sensor 36 detects that a test subject sits on a seat, the control device 22 transmits a signal of starting step S3 of setting measurement reference values to the data analyzer 60 through the transmitter-receiver 56, and then step S3 of setting measurement reference values is performed in synchronization with the data analyzer 60. If the seating detection sensor 36 repeats detection and non-detection predetermined times, this state is caused by influence of cleaning of the seat by the test subject, whereby it is desirable to return to S1 in this kind of state.

In step S3 of setting measurement reference values, the data analyzer 60 determines noise of stink gas attached to a test subject, which is determination of a level of noise caused by a test subject, on the basis of a measurement value measured by the odiferous gas sensor 26. That is, if a measurement value measured by the odiferous gas sensor 26 is insufficiently reduced and is unstable, it is determined that there is a possibility that disinfection is performed by using alcoholic disinfectant or the like to continue the display, "During measurement preparation. Wait for a while if possible", shown in the lower section of FIG. 4. Alternatively, if a level of noise caused by a test subject is a predetermined value or more, the data analyzer 60 transmits a signal to the nozzle driving device 42 of a local cleaning device to allow the nozzle driving device 42 to operate to clean the anus of a test subject, or the data analyzer 60 allows the display device 68 to notify a test subject that anus cleaning should be performed. In this way, anus cleaning and notification urging anus cleaning, and notification to the test subject of large noise by the data analyzer 60 function as second noise responding means that reduces test subject noise by response different from the first noise responding means. Further, the aforementioned first noise responding means is carried out when a test subject is not in the toilet installation room R, whereas the second noise responding means carried out when the test subject is in the toilet installation room R. On the other hand, if a measurement value measured by the odiferous gas sensor 26 is sufficiently reduced, this display is erased. In addition, if a measurement value measured by the odiferous gas sensor 26 is insufficiently reduced even if a predetermined time has elapsed, the data analyzer 60 stops measurement of physical condition and allows the display device 68 to display the stop to notify a test subject. In this way, the data analyzer 60 stops measurement of physical condition of a test subject when determining that gas components in the bowl 2*a* before a defecation period of the test subject are not suitable for measurement, and therefore serves as output result stabilizing means.

In addition, in step S3 of setting measurement reference values, the data analyzer 60, as described later, sets a reference value for estimating the amount of gas, on the basis of concentration of gas measured by the odiferous gas sensor 26.

Next, the data analyzer 60, as described in detail later, determines that a test subject performs an excretory act if a measurement value by the odiferous gas sensor 26 rises sharply from the reference value. The data analyzer 60 performs step S4 of measurement from when determining that the test subject performs an excretory act until when the seating detection sensor 36 detects that the test subject leaves the seat.

In step S4 of measurement, the control device 22 allows a storage device to store detection data for each test subject identified by test subject identification device 62, the detection data being measured by the hydrogen gas sensor 24, the odiferous gas sensor 26, the carbon dioxide sensor 28, the humidity sensor 30, the temperature sensor 32, the entrance detection sensor 34, the seating detection sensor 36, and the defecation/urination detection sensor 38. The control device 22 transmits these measurement values stored in the storage device to the data analyzer 60 through the transmitter-receiver 56, after step S4 of measurement is finished. In the present embodiment, although the measurement values are transmitted to the data analyzer 60 from the control device 22 after step S4 of measurement is finished, besides this, the measurement values may be transmitted in real time in parallel with measurement.

The control device 22 starts measurement of defecation gas even if a test subject inputs no information identifying the test subject into the test subject identification device 62. After then, if the test subject inputs information on the test subject during one defecation, detection data detected before the information is inputted is stored in the storage device in association with the inputted information on the test subject. This is a practical device corresponding to characteristics of defecation, in which a test subject is first allowed to perform no various kinds of input in an urgent situation of defecation, and to perform the input after calming down. In addition, if the test subject inputs no information on the test subject even if a predetermined time has elapsed after measurement has been started, the display device 68 and the speaker 70 output a message for urging the test subject to perform the input to notify the test subject. Accordingly, it is possible to prevent a test subject from omitting input.

At the same time, as with step S3 of setting measurement reference values, the data analyzer 60 determines whether measurement is possible or not. If the data analyzer 60 determines that the measurement is possible, the data analyzer 60 allows the display device 68 to display a message that the measurement being performed to the test subject, such as "Subject: Mr. Taro Toto (identification information on a test subject)", and "Measurement is ready. Measurement being performed", as shown in the lower section of FIG. 4.

Next, when the seating detection sensor 36 detects that a test subject leaves the seat, the control device 22 transmits a signal of starting step S5 of medical examination to the data analyzer 60 through the transmitter-receiver 56. When receiving the signal, the data analyzer 60 starts step S5 of medical examination.

The data analyzer 60 first calculates reliability of measurement that is described in detail later, on the basis of a measurement value measured by each sensor.

On the other hand, if no information identifying a test subject is inputted after the test subject has left the seat, the control device 22 prohibits cleaning of the flush toilet 2. That is, if no information for identifying a test subject is inputted, the control device 22 does not allow the flush toilet 2 to discharge cleaning water and allows a message urging the test subject to perform input to be displayed even if the test subject operates a cleaning button (not shown) of the remote control 8. Accordingly, it is possible to strongly urge a test subject to input information for identifying a test subject.

The data analyzer 60 also estimates the amounts of odiferous gas and hydrogen gas (healthy-state gas), as is described in detail later.

In step S5 of medical examination, the data analyzer 60 performs calculation of results of a medical examination to analyze physical condition of a test subject on the basis of time-dependent change in a plurality of detection data items that is detected in defecation performed multiple times in a predetermined period and that is stored in a storage device, as well as performs time-dependent diagnosis based on stored values, and then selects advice contents based on the time-dependent diagnosis. The data analyzer 60, as shown in a third section from the top of FIG. 5, allows the display device 68 to display advice contents selected as a message related to health management. In an example shown in FIG. 5, present physical condition of a test subject that corresponds to "insufficient physical condition" is displayed as a result of a medical examination is displayed, as well as "Intestinal environment may be wrong. Make efforts to have a healthy living habit" is displayed as an advice.

In a portion below that of the result of a medical examination, there is displayed the amount of healthy-state gas, such as hydrogen gas, and carbon dioxide gas, as well as the amount of wrong physical condition state gas, such as odiferous gas, in the measurement in this time. In a portion below that of the advice, measurement results of previous four times measurements are displayed together. If a test subject presses a button of "detailed screen" in a display screen, there is displayed a table showing change in physical condition of a test subject for the last one month. This display will be described later. In this way, analysis results displayed in the display device 68 of the remote control 8 include only a state of physical condition, an advice, and change in physical condition (history of measurement data), and include no notification related to a determination result of disease of cancer, such as displayed in the medical facility terminal 16. These analysis results may be notified in the terminal 14 for a test subject.

As shown in a lowermost section of FIG. 5, reliability of measurement data in this time is displayed in a lower portion of a screen of the display device 68. In the example shown in FIG. 5, the reliability is displayed as "4" that is relatively high. If the reliability is low, a cause of decrease in reliability as well as an advice for improving the decrease is displayed in a portion below that of display of the reliability. For example, if residual gas noise caused by gas remaining in a bowl, or test subject noise caused by a test subject, is large, a test subject is notified that the noise reduces the reliability to affect measurement results. Accordingly, display of reliability by the display device 68 serves as noise responding means. Calculation of reliability is described later.

Next, when the entrance detection sensor 34 detects that a test subject leaves the toilet installation room R, the control device 22 transmits a signal of transmitting data to the data analyzer 60 through the transmitter-receiver 56. When receiving the signal, the data analyzer 60 performs step S6 of communication.

In step S6 of communication, the data analyzer 60 transmits the following to the server 12 through a network: information for distinguishing a test subject identified by the test subject identification device 62; data measured by various sensors; calculated reliability; information on a measurement date and time; stool condition information on at least one of the amount of stool and a state of the stool acquired by the defecation/urination detection sensor 38; and notifying data including defecation history information. The server 12 records the information received in a database.

The control device 22 also performs step S7 of improving environment after measurement after the entrance detection sensor 34 has detected that a test subject has left the toilet installation room R.

The control device 22 allows the odiferous gas sensor 26 to measure concentration of gas in step S7 of improving environment after measurement. If concentration of gas measured by the odiferous gas sensor 26 is larger than a predetermined value even if a predetermined time has elapsed after a defecation period has been finished, the control device 22 determines that there is a stool attached to the bowl 2*a* of the flush toilet 2 to allow the toilet cleaning device 46 to discharge cleaning water stored in a cleaning water tank into the bowl 2*a* to clean the inside of the bowl 2*a*, or to allow the toilet disinfection device 48 to create disinfecting water, such as hypochlorous acid water, from tap water, or the like to spray disinfecting water created onto the bowl 2*a* to disinfect the bowl 2*a*.

The additional toilet cleaning by the toilet cleaning device 46, and disinfection of the bowl 2*a* by the toilet disinfection device 48 function as residual gas removing means that reduces concentration of remaining odiferous gas. Toilet cleaning which is performed automatically by the residual gas removing means is preferably set so that its cleaning capability is higher than that of usual toilet cleaning performed by allowing a test subject to operate a cleaning switch (not shown) of the remote control 8. Specifically, it is preferable that the toilet cleaning performed by the residual gas removing means is set to have a high frequency of discharge of cleaning water into the bowl 2*a*, or flow velocity of the cleaning water is set high. Further, the disinfection of the bowl 2*a* performed by the residual gas removing means is set so that its disinfection capability is higher than that of usual disinfection of the bowl performed by allowing a test subject to operate a disinfection switch (not shown) of the remote control 8. Specifically, the disinfection of the bowl performed by the residual gas removing means is set so that water for disinfection of higher concentration as compared with usual disinfection is sprayed, or a large amount of water for disinfection is sprayed.

If concentration of gas measured by the odiferous gas sensor 26 is more than a predetermined value even if a predetermined time has elapsed after a defecation period has been finished, the residual gas removing means determines that there is a contamination in the duct 18*a* to allow the duct cleaner 58 to operate. The duct cleaner 58 cleans the inside of a duct 18*a* attached to the suction device 18 with hypochlorous acid acquired by electrolysis of tap water, or the like.

If concentration of gas measured by the odiferous gas sensor 26 does not decrease sufficiently and is still more than the predetermined value even if the cleaning and the disinfection processing, described above, are performed, the residual gas removing means allows the display device 68 to display a message of encouraging cleaning of the flush toilet 2.

Then, in step S7 of improving environment after measurement, the control device 22 allows the sensor heater 54, the suction device 18, and the toilet lid opening/closing device 40 to switch to the measurement waiting mode to finish one measurement.

Next, with reference to FIG. 6, the physical condition display table will be described. The physical condition display table is to be displayed by pressing the button of "detailed screen" in the display screen shown in FIG. 5.

A storage device on the remote control 8 side stores the physical condition display table, defecation dates and times of a test subject in association with identification information on the test subject, and previous measurement data, for each test subject. Although the previous measurement data stored in the storage device on the remote control 8 side may be data throughout a defecation period, measurement data on defecation gas discharged by the first excretory act in the defecation period (the first measurement data during the excretory act) is preferable due to capacity of the storage device.

Figure 6:
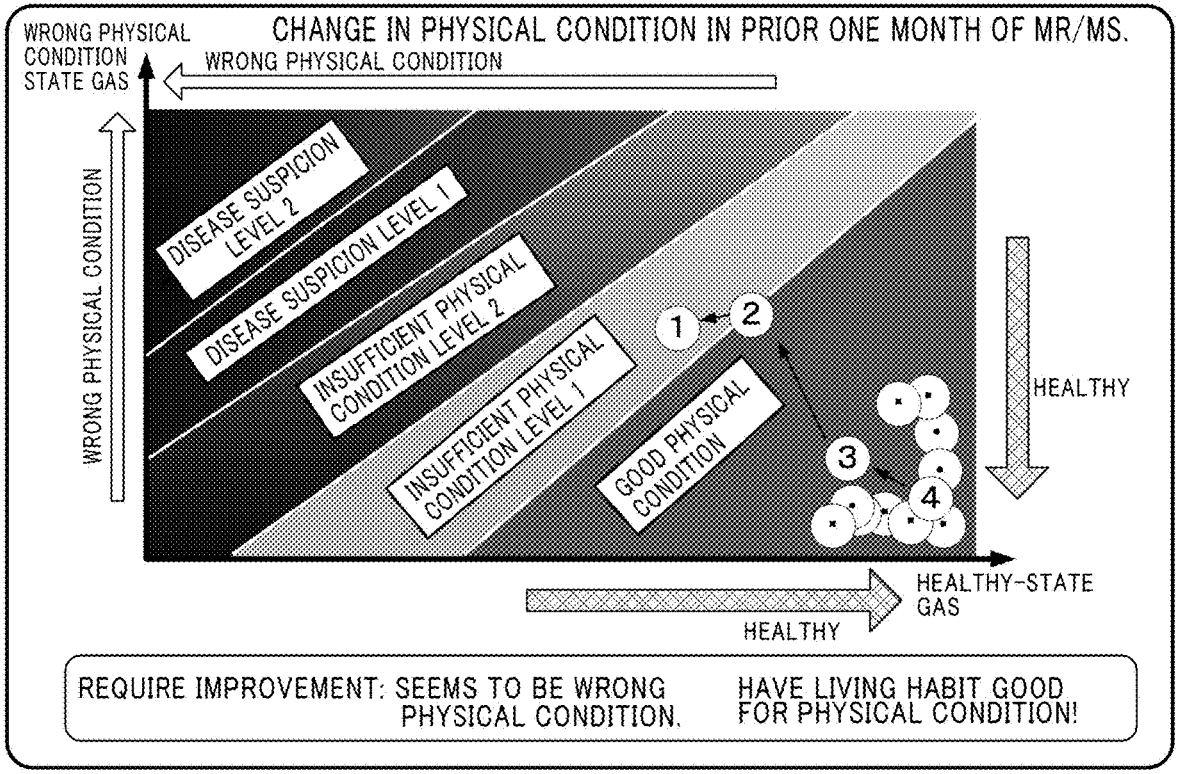
FIG. 6 is a view showing an example of a table of displaying physical condition displayed in the display device of the remote control provided in the biological information measurement system of the first embodiment of the present invention.

As shown in FIG. 6, the physical condition display table is determined on the basis of an experiment performed by the present inventors, described above, and is a graph in which the vertical axis represents an index related to the amount of odiferous gas (referred to as wrong physical condition state gas in the display), referred to as a first index, and the horizontal axis represents an index related to the amount of healthy-state gas, referred to as a second index. The first index relates to the amount of odiferous gas based on first detection data detected by the gas detector 20, and the second index relates to the amount of hydrogen gas of healthy-state gas based on second detection data detected by the gas detector 20. The display device 68 of the remote control 8 displays the physical condition display table with the vertical axis and the horizontal axis as above, in which a measurement result of defecation gas of a test subject is plotted in a time-dependent manner. That is, as shown in FIG. 6, a plotted point representing the latest measurement result of the same test subject is referred to as "1", that representing the last result is referred to as "2", that representing the last but one result is referred to as "3", and the like, and then each of plotted points of the last thirty times is displayed with a numeral. Accordingly, a test subject can recognize time-dependent change in his or her own physical condition. Although the present embodiment displays plotted points of thirty times, those of a few weeks and a few months may be available, or those in units of year may be also available because cancer develops in years. It is more desirable to enable a test subject to change a display range according to a situation. Further, it is needless to say that if a display range is wide, it is more preferable to change a display method in consideration of viewability so that monthly averages of plotted points for one year, or two years, are used.

The physical condition display table sets regions of a plurality of stages corresponding to whether physical condition is good or wrong, in accordance with a relationship between the index related to healthy-state gas and the index related to odiferous gas, such as: a "disease suspicion level 2", a "disease suspicion level 1", an "insufficient physical condition level 2", an "insufficient physical condition level 1", and a "good physical condition". As shown in FIG. 6, the "disease suspicion level 2" corresponding to the worst state of physical condition is set in a upper-left region in the physical condition display table, where the amount of odiferous gas is maximum and the amount of healthy-state gas is minimum. On the other hand, the "good physical condition" corresponding to the best state of physical condition is a lower-right region in the physical condition display table, where the amount of odiferous gas is minimum and the amount of healthy-state gas is maximum. The "disease suspicion level 1", "insufficient physical condition level 2", and "insufficient physical condition level 1", showing physical condition levels between the worst and best conditions, are set in the order from the upper-left in the physical condition display table as belt-like regions rising diagonally up and to the right. This kind of physical condition display table is preset in accordance with weight, age, sex, and the like of a test subject, and displaying plotted points based on the first and second indexes in the table enables analysis based on detection data and test subject information to be performed.

As above, in the present embodiment, two indexes of the index related to the amount of odiferous gas and the index related to the amount of healthy-state gas are used, so that it is possible to evaluate physical condition of a test subject and change in physical condition thereof in more detail. For example, even in a case where the amount of healthy-state gas showing a good physical condition is large, if the amount of odiferous gas is also large, evaluation is not the level of the best physical condition (the upper-right region in the physical condition display table). Conversely, even in a case where the amount of healthy-state gas showing a good physical condition is very low, if the amount of odiferous gas is low, evaluation is not the level of the worst physical condition (the lower-left region in the physical condition display table).

For example, a boundary line between the "insufficient physical condition level 1" and the "insufficient physical condition level 2" showing a worse state than that of the level 1 is drawn rising diagonally up and to the right so that as the amount of the index related to healthy-state gas in the horizontal axis increases, the index related to the amount of odiferous gas in the vertical axis also increases, and the "insufficient physical condition level 2" showing a state where physical condition is wrong is distributed on a side of the boundary line where the index related to the amount of odiferous gas is large. The boundary line is set in this way, so that in the present embodiment, even if the amount of the index related to healthy-state gas in the horizontal axis is the same value, evaluation of physical condition varies depending on a value of the index related to the amount of odiferous gas in the vertical axis. In order to acquire the same evaluation, it is required that as a value of the amount of odiferous gas in the vertical axis increases, a value of the amount of healthy-state gas in the horizontal axis also increases.

The storage device on the remote control 8 side stores advices corresponding to the states of physical condition. Specifically, there are stored advices, such as: "Present to a hospital" corresponding to a state of physical condition, the "disease suspicion level 2"; "Recommend presenting to a hospital" corresponding to a state of physical condition, the "disease suspicion level 1"; "Concern for disease increases. Reduce stress and improve a living habit immediately" corresponding to a state of physical condition, the "insufficient physical condition level 2"; "Intestinal environment is wrong. Make an effort to have a healthy living" corresponding to a state of physical condition, the "insufficient physical condition level 1"; and "Physical condition is good" corresponding to a state of physical condition, the "good physical condition". In the physical condition display table, plotted points showing physical condition of a test subject, as well as an advice corresponding to a region where the latest plotted point is positioned is displayed.

However, the display device 68 of the remote control 8 does not plot each of analysis results acquired by the data analyzer 60 as it is in the physical condition display table, and plots each of the analysis results at a position to which each of them is displaced after predetermined correction has been applied to each of them. It is assumed that the biological information measurement system 1 of the present embodiment detects disease, such as colorectal cancer, and this kind of disease does not steeply develop in a few days. Meanwhile, the biological information measurement system 1 of the present embodiment sucks defecation gas from the bowl 2a of the flush toilet 2 installed in the toilet installation room R to analyze the sucked gas, and it is impossible to collect all of the defecation gas. In addition, there is a possibility that various factors, such as that a test subject wears perfume, and that gas to which the odiferous gas sensor 26 is sensitive, such as odiferous gas, remains in the toilet installation room R, may cause an error in measurement results of physical condition.

Thus, if physical condition displayed on the basis of one measurement result of a test subject greatly inclines toward wrong physical condition, an unnecessary mental burden is applied to a test subject. In addition, if a measurement result of physical condition greatly varies for each measurement, it results in losing confidence of a test subject in a measurement result of physical condition. Thus, the biological information measurement system 1 of the present embodiment allows the data analyzer 60 to apply correction to an analysis result to prevent a measurement result to be displayed from greatly varying for each measurement. However, detection data stored in the storage device of the remote control 8 and detection data transmitted to the server 12 to be stored, to which no correction is applied, are stored along with reliability of the detection data. It is preferable that the storage device of the remote control 8 stores a coordinate of a display after correction in consideration of a next display. All of detection data acquired by the biological information measurement system 1 of the present embodiment in this way does not have high reliability. However, if data on daily defecation act is continuously acquired for a long period to be accumulated in the storage device of the remote control 8 and the server 12, it is possible to detect change in physical condition of a test subject for a long period. As a result, it is possible to call attention to a test subject before physical condition of the test subject is greatly deteriorated, to prevent the test subject from having a serious disease, such as colorectal cancer.

In this way, correction that is applied to detection data serves as output result stabilizing means that prevents an index of the physical condition of a test subject that is outputted to the display device 68 from inclining in a direction of a wrong physical condition by a detection error and the like.

In the present embodiment, it is not always required to apply correction to detection data to be stored in the storage device of the remote control 8, and also detection data after the correction may be stored.

Next, with reference to FIG. 7A and FIG. 7B, correction of plotted points will be described.

Figure 7A:
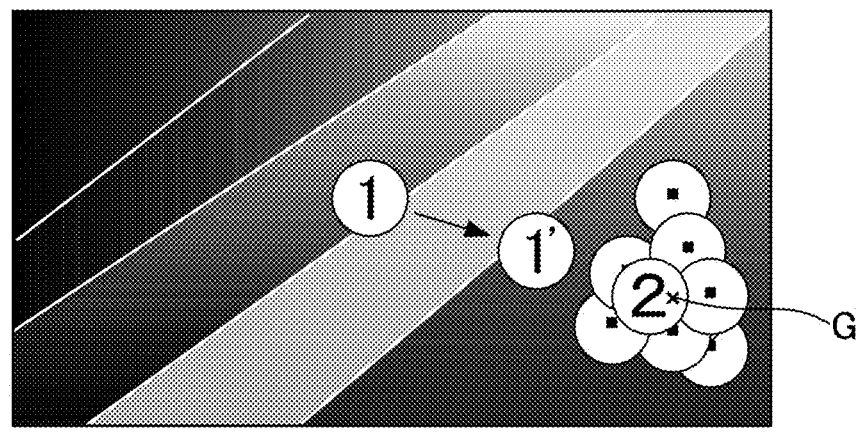
FIG. 7A is a view showing an example of displacement of a plotted point of updated data by correction.
Figure 7B:
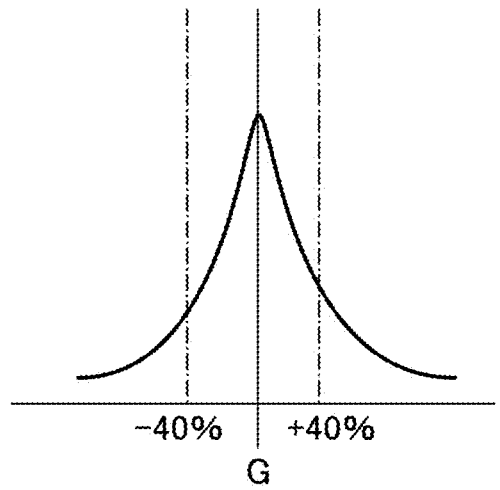
FIG. 7B is a diagram showing limit processing with respect to the amount of displacement of a plotted point.

FIG. 7A shows an example of displacement of a plotted point of updated data by correction, and FIG. 7B shows limit processing with respect to the amount of displacement of a plotted point.

First, as shown in FIG. 7A, a plotted point calculated by the data analyzer 60 on the basis of the latest measurement is represented as "1", and the point is greatly displaced from the center G of an area of plotted points of measurement data of the last thirty times. In this way, if the plotted point "1" that is greatly displaced from distribution of measurement data up to the previous measurement is displayed, an excessive mental burden may be applied to a test subject. Since a risk of cancer does not increase in a day, it is highly possible that this kind of large change in measurement data does not show an increase in a risk of cancer, but a result of a bad living habit in the previous day, or influence of noise. In the present embodiment, correction is performed in a manner that gives due consideration for applying no excessive mental burden to a test subject. Thus, if the latest analysis result varies toward a wrong physical condition side (in an upper-left direction), the data analyzer 60 displaces a position at which the plotted point "1" is displayed in the physical condition display table toward the center G of an area by a predetermined distance on the basis of reliability of measurement data in this time to allow the plotted point "1" to be displayed. That is, in an example shown in FIG. 7A, the latest measurement data is displayed at a position of a plotted point "1'" acquired by correcting the plotted point "1" so that the plotted point "1" is displaced toward the center G of an area (on a good physical condition side), and the plotted point "1" is not actually displayed. A displacement distance of the plotted point "1" toward the center G of an area direction increases, as reliability of the latest measurement data decreases. In this way, displacing the latest plotted point on a side showing good physical condition enables a mental burden to a test subject to be reduced. Calculation of reliability of measurement data is described later. However, if displacement of the latest plotted point toward the wrong physical condition side continues predetermined times or more, the data analyzer 60 reduce the amount of correction (the amount of correction of displacement). Accordingly, a test subject can recognize that his or her own physical condition is deteriorated, and can be encouraged to make an effort to improve the physical condition.

If a very large noise is applied to the latest measurement of physical condition to very greatly shift the latest plotted point, it is thought that physical condition displayed may be greatly displaced toward the wrong physical condition side even if the correction described in FIG. 7A is applied. Thus, as shown in FIG. 7B, there is a predetermined limit of a displacement distance of the latest data from the center G of an area. That is, displacement of the latest data from the center G of an area is limited to a range of ±40% of a coordinate value of the center G, and even if the latest data is displaced by 40% or more from the coordinate of the center G of an area, the latest data is plotted at a position displaced by 40%. For example, in a case where a coordinate value of the center G of an area is represented as (x, y), a range of coordinate values at which the latest data can be plotted is represented as (0.6x to 1.4x, 0.6y to 1.4y), and the latest data is not plotted at a position out of the range.

In addition, if displacement of the latest data exceeding this kind of 40% continues twice, a range in which the latest data can be displaced is eased to 60%. Accordingly, for example, if the coordinate value of the center G of an area is represented as (x, y), a range of coordinate values at which the latest data can be plotted is changed to that represented as (0.4x to 1.6x, 0.4y to 1.6y). Because it is thought that if a large displacement of the latest data as above occurs at high frequency, it is not a mere measurement error, but a reflection of some sort of change in physical condition of a test subject.

Next, with reference to FIG. 8, a diagnosis table on a server side will be described. Processing in the server below is performed by data analyzing means provided in the server 12.

Figure 8:
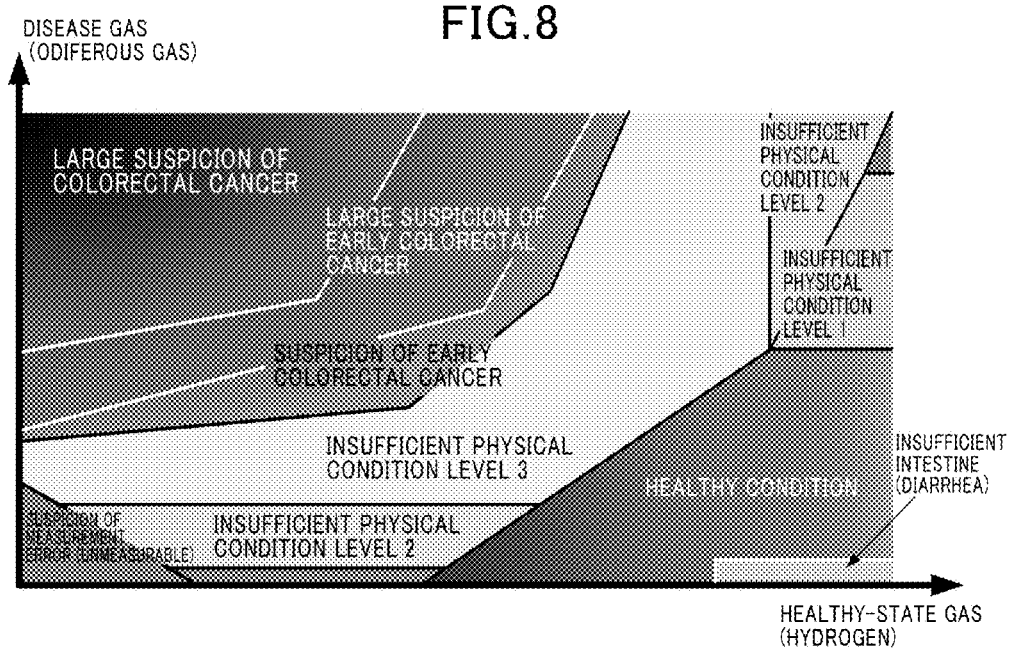
FIG. 8 is a diagram showing an example of a diagnosis table displayed on a server side, in the biological information measurement system of the first embodiment of the present invention.

FIG. 8 shows an example of a diagnosis table displayed on the server side. As described above, in the biological information measurement system 1 of the present embodiment, measurement data for all defecation periods analyzed by the data analyzer 60 is sequentially transmitted to the server 12 through the Internet to be stored in a database on the server side. This accumulated measurement data can be displayed in the medical facility terminal 16 installed in a medical facility 302 registered by a test subject. For example, when a test subject has a medical examination in the medical facility after receiving the message, "Recommend presenting to a hospital" displayed in the display device 68 of the remote control 8, the medical facility terminal 16 enables a diagnosis table for a server to be displayed. In the diagnosis table, its vertical axis and horizontal axis represent the same indexes as those of the physical condition display table to be displayed in the display device 68 of the remote control 8, and a state of physical condition assigned to each region is more specific. A doctor refers to measurement data on a test subject stored in a database on a server 12 side in the medical facility terminal 16 to be able to refer to time-dependent physical condition of the test subject, and thus the data can be useful for inspection and treatment in the medical facility. Alternatively, it is also possible to configure the present invention so that if measurement data transmitted to the server 12 shows excessive wrong physical condition, a medical facilities registered by a test subject notifies the terminal 14 for a test subject, corresponding the test subject, of encouraging the test subject to have a medical examination.

The diagnosis table displayed in the medical facility terminal 16 is different from the physical condition display table displayed in the display device 68 of a test subject as described above. As shown in FIG. 8, the diagnosis table on the server 12 side is determined on the basis of an experiment performed by the present inventors, and in the diagnosis table, a disease state is associated corresponding to a relationship between the amount of healthy-state gas and the amount of odiferous gas. Specifically, in the diagnosis table, the following regions are set corresponding to a relationship between the amount of healthy-state gas and the amount of odiferous gas: "Large suspicion of colorectal cancer", "Large suspicion of early colorectal cancer", "Suspicion of early colorectal cancer", "Insufficient physical condition level 3", "Insufficient physical condition level 2", "Insufficient physical condition level 1", "Healthy condition", "Insufficient intestine (diarrhea)", and "Suspicion of measurement error".

In a diagnosis table on the server side, set in this way, previous measurement data on a test subject is plotted in a time-dependent manner on the basis of a position of a plotted point to perform determination of disease of cancer, such as: "Large suspicion of colorectal cancer", "Large suspicion of early colorectal cancer", and "Suspicion of early colorectal cancer". No correction as well as no limit is applied to a plotted point displayed in the diagnosis table on the server side, so that a doctor checks data displayed for diagnosis along with its reliability in a comprehensive manner. Since a diagnosis table and a determination result displayed in the medical facility terminal 16 are set based on the premise that a doctor refers to them, a name of disease, development thereof, and the like, are more specifically displayed. If plotted points are positioned, for example, in regions related disease of cancer, such as the "Large suspicion of colorectal cancer", "Large suspicion of early colorectal cancer", and "Suspicion of early colorectal cancer", for a long time, a message of a high possibility of disease is displayed. A doctor is able to check plotted points shown, reliability of measurement, and the like, for diagnosis in a comprehensive manner to notify a test subject of a state of the physical condition. The medical facility terminal 16 is configured to be capable of also displaying reliability calculated by referring to a database, data measured by various sensors, information on stool condition related to at least one of the amount of stool and condition of stool, and defecation history information, along with a diagnosis table in which previous measurement data is plotted in a time-dependent manner.

A large number of test subject-side devices 10 are connected to the server 12, a large number of measurement data items of test subjects are accumulated in the server 12. In addition, a database on the server 12 side also accumulates data on disease condition acquired from a result of detailed examination of a test subject, performed in a medical facility, after the test subject has had a medical examination in the medical facility on the basis of certain measurement data. Thus, it is possible to accumulate data acquired by associating data measured by the biological information measurement system 1 of the present embodiment with actual disease condition, on the server 12 side. The diagnosis table on the server side is sequentially updated on the basis of measurement data on a large number of test subjects accumulated in this way, so that it is possible to perform diagnosis with higher accuracy on the basis of the updated diagnosis table. It is also possible to update the physical condition display table on the basis of the data accumulated on the server side. The physical condition display table updated on the basis of the data on the server side is downloaded into each of the test subject-side devices 10 through the Internet to be displayed in the display device 68 of the remote control 8. Even if the physical condition display table is updated, a message to be shown to a test subject is corrected to an appropriate content in the physical condition display table that is to be directly presented to the test subject.

Next, with reference to FIG. 9, data detected by each of sensors provided in the biological information measurement system 1 of the present embodiment, and estimation of the amount of gas based on the data, will be described.

Figure 9:
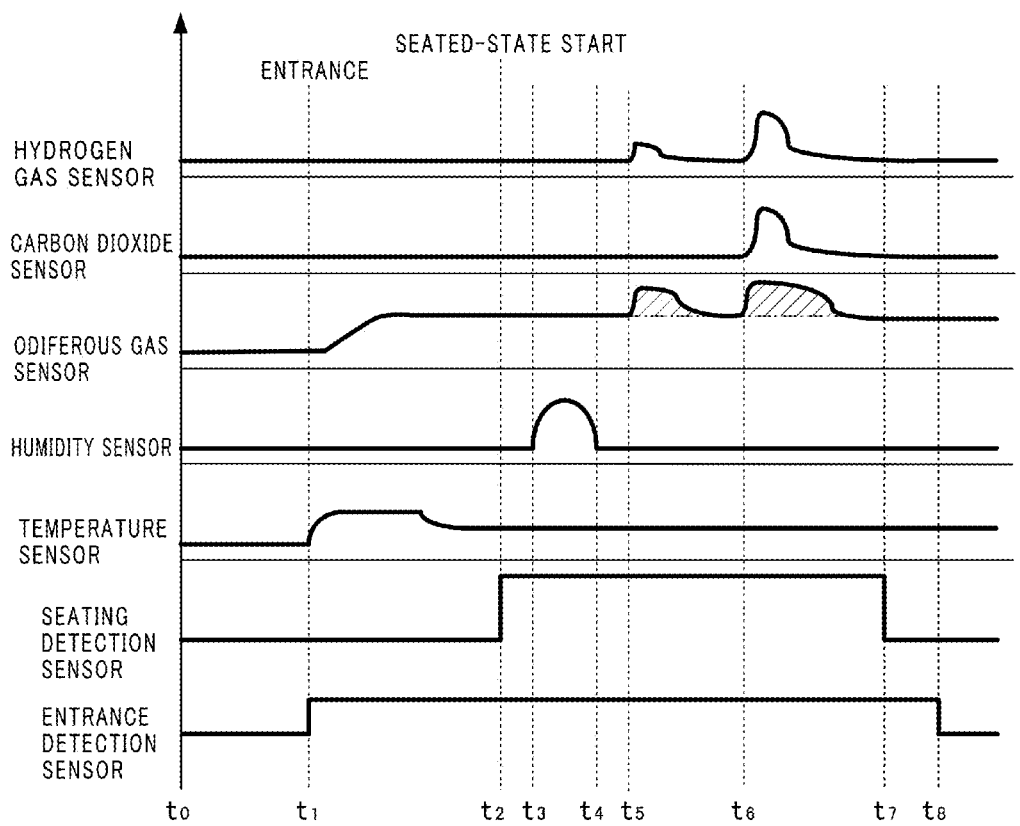
FIG. 9 is a graph schematically showing a detection signal of each of sensors provided in a biological information measurement system 1 in one defecation act of a test subject.

FIG. 9 is a graph schematically showing a detection signal of each of the sensors provided in the biological information measurement system 1 in one excretory act of a test subject. FIG. 9 shows a waveform of a detection signal of each of the sensors, such as the hydrogen gas sensor 24, the carbon dioxide sensor 28, the odiferous gas sensor 26, the humidity sensor 30, the temperature sensor 32, the seating detection sensor 36, and the entrance detection sensor 34, in the order from an upper section.

Estimation of the amount of gas based on a detection signal of each of the sensors is performed by the data analyzer 60 serving as physical condition state discrimination means for discriminating a physical condition state, that is, by a CPU built in the remote control 8 and a storage device, or by a CPU of the server 12 and a storage device. In the data analyzer 60, there are preset a starting threshold value of a rate of change in the amount of gas for determining starting time of an excretory act, read out from storage means of the remote control 8, and a stability threshold value with respect to the amount of gas, capable of allowing stable measurement to be performed. The term, an excretory act, here includes a fart.

First, at time t1 of FIG. 9, the entrance detection sensor 34 detects entrance of the test subject. The data analyzer 60 allows the odiferous gas sensor 26 to measure the amount of odiferous gas even in a state before the entrance detection sensor 34 detects entrance of the test subject into the toilet installation room R (time $t_0$ to $t_1$). Even in this case, the odiferous gas sensor 26 reacts due to influence of aromatic, and remaining stool attached to the bowl 2a of the flush toilet 2 to output a certain level of a detection signal. In this way, a measurement value of the odiferous gas sensor 26 before entrance of the test subject is set as an environment reference value of the amount of gas that is residual gas noise. In a state before the entrance detection sensor 34 detects entrance of the test subject, the odiferous gas sensor 26 and the suction device 18 are in a power saving state. Accordingly, temperature of the sensor heater 54 for heating the catalyst of the odiferous gas sensor 26 is set lower, and a rotation speed of the suction fan 18c is also reduced to reduce a flow rate of passing air.

When the entrance detection sensor 34 detects entrance of the test subject at the time $t_1$, the odiferous gas sensor 26 and the suction device 18 are in a startup state. Accordingly, temperature of the sensor heater 54 of the odiferous gas sensor 26 increases, as well as a rotation speed of the fan of the suction device 18 increases to suck gas at a predetermined flow rate. As a result, a detection value by the temperature sensor 32 temporarily greatly increases, and then converges to a proper temperature (after the time $t_1$ of FIG. 9). In the present specification, a period in which the entrance detection sensor 34 detects entrance of the test subject into the toilet installation room R (time $t_1$ to $t_8$ of FIG. 9) is referred to as one "defecation act". When the test subject enters the toilet installation room R, a detection signal detected by the odiferous gas sensor 26 increases, because the odiferous gas sensor 26 reacts to a body odor of the test subject, perfume and hair liquid used by the test subject, and the like. That is, an increment from residual gas noise before the test subject enters the toilet installation room R is test subject noise caused by the test subject. Noise measurement means built in the data analyzer detects residual gas noise caused by gas remaining in the bowl 2a, and test subject noise caused by the test subject. The odiferous gas sensor 26 is set at a very high sensitivity to detect a very trace amount of odiferous gas contained in the order of ppb in defecation gas discharged into a toilet to react even to the order of odor to which a human's sense of smell is insensitive.

Next, when the seating detection sensor 36 detects that the test subject sits on the seat 4 at time $t_2$ of FIG. 9, this time point is set as a starting point of one defecation period of the test subject. In the present specification, a period in which the seating detection sensor 36 detects whether the test subject sits on the seat 4 (time $t_2$ to $t_7$ of FIG. 9) is referred to as one "defecation period". A detection value by the odiferous gas sensor 26 after the starting point of the defecation period (time $t_2$) and immediately before start of the first excretory act (time $t_5$ in FIG. 9) that is described later is set as a reference value of residual gas.

In an example shown in FIG. 9, a detection value of the humidity sensor 30 increases in a period between the time $t_3$ and the time $t_4$ after the test subject has sat on the seat 4 at the time $t_2$, because urination of the test subject is detected. Then, since there is little change in a detection value of odiferous gas sensor 26, the data analyzer 60 determines that an excretory act is not performed. In this way, urination by a test subject hardly influences the detection value of the odiferous gas sensor 26, because discharged urea immediately flows into standing water in the bowl 2a. Subsequently, a detection value of each of the hydrogen gas sensor 24 and the odiferous gas sensor 26 steeply rises at the time $t_5$. In this way, if the detection value of the odiferous gas sensor 26 steeply rises in a defecation period after the test subject has sat on the seat 4, the data analyzer 60 determines that an excretory act is performed.

When the excretory act is performed, the data analyzer 60 estimates the amount of odiferous gas discharged from the test subject on the basis of a fluctuation range of an increment of a detection value of the odiferous gas sensor 26 from the reference value of residual gas (a hatched area in a graph of detection values of the odiferous gas sensor 26). That is, the data analyzer 60 sets a value of detection data at the starting point of the defecation period of the test subject as the reference value which is a noise level caused by the test subject to estimate the amount of odiferous gas by the first excretory act by performing time integration of a difference between the detection value detected by the odiferous gas sensor and the reference value, from a starting point to an end point. In this way, since the data analyzer 60 estimates the amount of odiferous gas on the basis of a difference from a reference value, it is possible to reduce influence of noise caused by a test subject. Accordingly, a circuit built in the data analyzer 60, which performs the calculation, serves as noise reducing means, and also functions as second noise responding means that reduces influence of test subject noise. If a noise level caused by the test subject is a predetermined value or more, the data analyzer 60 allows the display device 68 to notify the fact. Details of estimation of an amount of odiferous gas are described later. Likewise, the data analyzer 60 estimates the amount of hydrogen gas discharged from the test subject on the basis of an increment of a detection value of the hydrogen gas sensor 24 from a reference value of residual gas. After an excretory act of the test subject has been performed (after the time $t_5$ of FIG. 9), a detection value of each of the odiferous gas sensor 26 and the hydrogen gas sensor 24 returns to the reference value of residual gas. Subsequently, when the second excretory act of the test subject is performed at the time $t_6$, a detection value of each of the odiferous gas sensor 26, the carbon dioxide sensor 28 and the hydrogen gas sensor 24 steeply rises again. For the second excretory act, as with the first excretory act, the amount of odiferous gas and the amount of hydrogen gas, discharged from the test subject, are also estimated on the basis of an increment from the reference value of residual gas. When the amount of odiferous gas and the amount of hydrogen gas of the second excretory act or later are estimated, the reference value may be changed for each excretory act in consideration of influence of floating stool in seal water in the bowl, and the like.

In this way, when a test subject performs an excretory act a plurality of times after entering the toilet installation room (that is, a change in gas amount of a predetermined threshold value or more is detected a plurality of times), an amount of defecation gas by an excretory act at each time is similarly estimated. When the amount of defecation gas of an excretory act of the second time or later is calculated, the reference value may be changed for each excretory act in consideration of influence of floating stools in seal water in the bowl, and the like.

Subsequently, the seating detection sensor 36 detects that the test subject leaves the seat at the time $t_7$ of FIG. 9 to finish the one defecation period, and then the entrance detection sensor 34 detects that the test subject leaves the toilet installation room at the time $t_8$ to finish the one defecation act. The data analyzer 60 estimates the amount of defecation gas by excretory act of each time until the entrance detection sensor 34 detects that the test subject leaves the toilet installation room.

Each of the remote control 8 and the server 12 determines physical condition of the test subject on the basis of the amount of defecation gas measured in this way. In this case, it is desirable to enable measurements of physical condition to be displayed on the remote control 8 side during a defecation period, or immediately after the defecation period has been finished. Then, if excretory acts are performed multiple times, stools accumulate in the bowl 2a to reduce accuracy of measurement of the amount of defecation gas, based on odiferous gas. Meanwhile, in the first excretory act, defecation gas reaching the most downstream portion of the large intestine is discharged, so that it is possible to acquire most useful information for measurement of physical condition to increase reliability of the measurement. Based on the fact, on the remote control 8 side, when the amount of defecation gas (the amount of odiferous gas and hydrogen gas) by the first excretory act is estimated, physical condition of a test subject is measured on the basis of only the amount of defecation gas by the first excretory act to be displayed in the display device 68 of the remote control 8. Alternatively, it is also possible to measure a state of physical condition by allowing a weighting of a measurement value based on detection data on an initial excretory act in one defecation act to be higher than a weighting for a later excretory act.

In contrast, on the server 12 side, it is desirable to accurately perform determination by using a total amount of defecation gas by excretory acts of multiple times. Thus, on the server 12 side, a state of physical condition of a test subject is determined on the basis of a total amount of defecation gas by excretory acts of multiple times (a total amount of odiferous gas and hydrogen gas), or more preferably, on the basis of a total amount of defecation gas by every excretory act included in one defecation period from sitting on a seat to leaving the seat. Although determination of a state of physical condition of a test subject on the server 12 side does not always require a total amount of defecation gas by every excretory act included in one defecation period, it is preferable that the determination is based on a total amount of defecation gas by every excretory act included in defecation periods of multiple times.

Figure 10A:
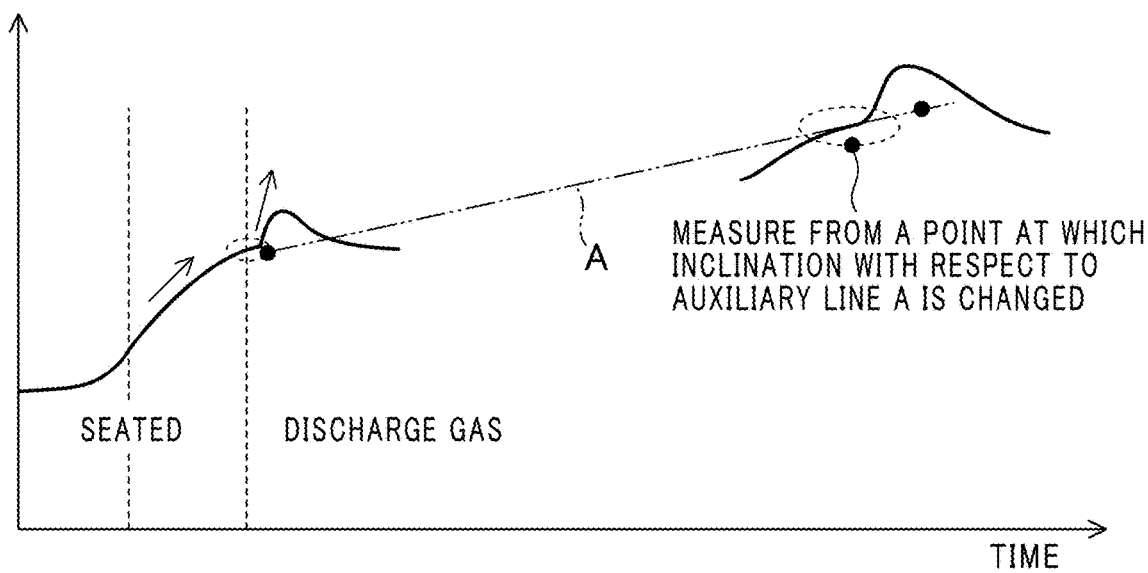
FIG. 10A is a graph explaining estimation of the amount of discharge of odiferous gas in a case where a reference value of residual gas is not fixed.

In the example shown in FIG. 9, although the reference value of residual gas is constant, it is possible to estimate the amount of discharge of odiferous gas even if the reference value is not constant. For example, if a detection value detected by the odiferous gas sensor 26 tends to increase, as shown in FIG. 10A, a reference value is indicated as an auxiliary line A that is drawn on the assumption that a rate of change in an increase of a detection value detected by the odiferous gas sensor 26 before an excretory act is started continues before and after the excretory act. Accordingly, it is possible to estimate the amount of odiferous gas by determining that one excretory act is started at the time when an inclination of detection values of the odiferous gas sensor 26 from the auxiliary line A greatly varies.

The amount of odiferous gas is estimated on the basis of a difference from a reference value that is set by using the amount of residual gas before an excretory act, so that it is desirable that there is no large change in the reference value. Thus, if a rate of change of detection values detected by the odiferous gas sensor 26 before a starting point of an excretory act (or a rate of change of a reference value of an inclination of the auxiliary line A) is a first stability threshold value or less, the data analyzer 60 allows notification means composed of the display device 68 of the remote control 8 or the speaker 70 to notify the fact that estimation of the amount of defecation gas has high accuracy.

Meanwhile, if a spray aromatic is sprayed immediately before an excretory act, or a disinfecting sheet of an alcoholic toilet seat disinfectant or a disinfect spray is used, a detection value detected by the odiferous gas sensor 26 before the excretory act greatly varies. If a value in this kind of state is set as a reference value, it is impossible to estimate an accurate amount of odiferous gas. Thus, if a reference value of a noise level caused by a test subject is a predetermined value or more, or a rate of change of the reference value is a second stability threshold value or more, the data analyzer 60 allows the notification means composed of the display device 68 of the remote control 8 or the speaker 70 to notify the fact that estimation of the amount of defecation gas has low accuracy. If an excretory act is performed even if this kind of notification is performed, no measurement for analysis of physical condition is performed, or reliability of measurement is reduced.

Figure 10B:
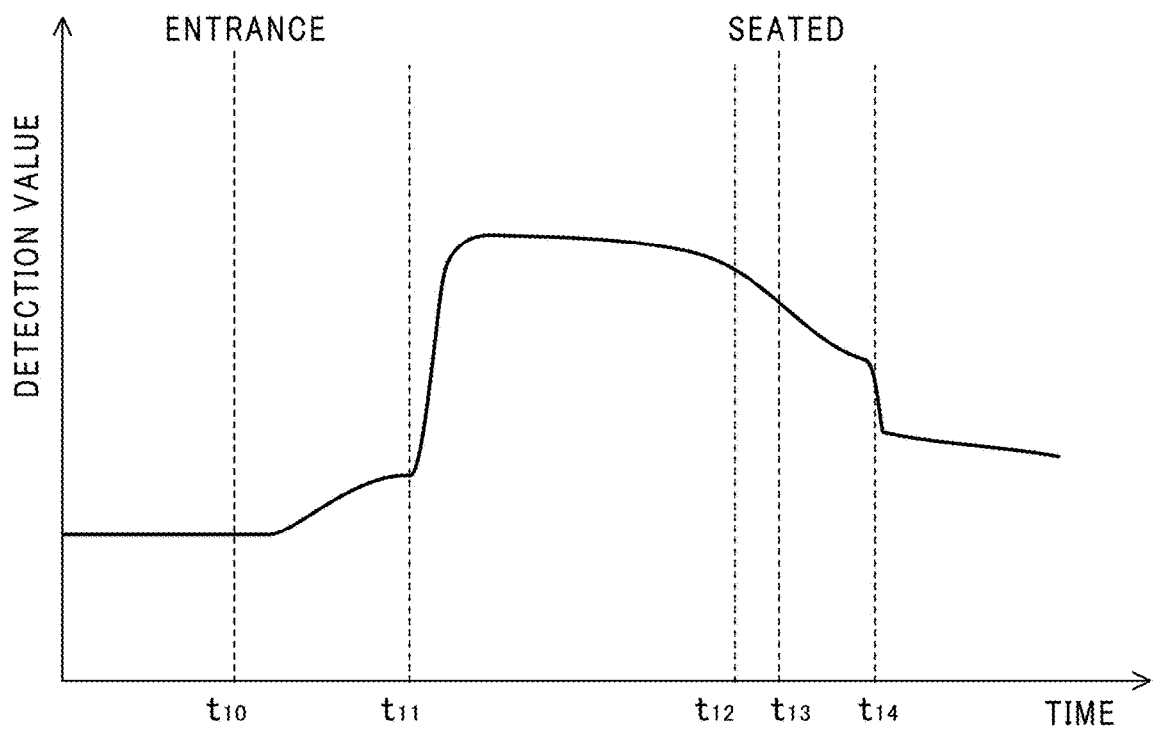
FIG. 10B is a graph showing an example of detection values acquired by an odiferous gas sensor in a case where a test subject uses an alcoholic toilet seat disinfectant.

Next, with reference to FIG. 10B, detection of use of an alcoholic toilet seat disinfectant will be described. FIG. 10B is a graph showing an example of detection values of the odiferous gas sensor 26 in a case where a test subject uses an alcoholic toilet seat disinfectant.

First, after the entrance detection sensor 34 has detected entrance of a test subject at time $t_{10}$ of FIG. 10B, a detection value of the odiferous gas sensor 26 gradually rises because the odiferous gas sensor 26 reacts to a body odor and the like of the test subject. Next, when the test subject takes out a seat disinfecting sheet using alcoholic disinfectant at time $t_{11}$, the odiferous gas sensor 26 reacts to a smell of alcohol so that its detection value steeply rises. When the test subject finishes disinfecting the seat 4 at time $t_{12}$, and throws away the disinfecting sheet into the bowl 2a, a detection value of the odiferous gas sensor 26 immediately starts to decrease because alcoholic has high volatility. The present inventors find out that the detection value steeply increased due to the alcoholic disinfectant decreases by waiting for a while to enable measurement because characteristics of the alcoholic disinfectant described above is different from those of remaining stink gas components. However, in a case of disinfect with an alcoholic disinfecting sheet, the sheet may float in seal water when thrown away. In this case, the alcohol continues to vaporize so that the decrease of the detection value steeply increased tends to be delayed. Thus, it is desirable to discharge the sheet as described below.

Subsequently, after the seating detection sensor 36 has detected that a test subject has sat on the seat at time $t_{13}$, if the test subject operates the cleaning switch (not shown) of the remote control 8 to perform cleaning of the flush toilet 2, a disinfecting sheet floating in seal water in the bowl 2a is discharged to allow a detection value of the odiferous gas sensor 26 to steeply decrease. If an alcoholic disinfectant is used, the odiferous gas sensor 26 generally operates as above.

If a detection value of the odiferous gas sensor 26 steeply increases to a predetermined value or more, in a period after the entrance detection sensor 34 has detected entrance of a test subject, and before the seating detection sensor 36 detects that the test subject sits on the seat, seat disinfection detecting means built in the data analyzer 60 determines that the test subject disinfects the seat 4, or the like, by using an alcoholic disinfectant. The present inventors find out that it is possible to detect an act of disinfecting the seat 4 of a specific act performed by a test subject in the toilet installation room R from a detection signal of each of the entrance detection sensor 34, the seating detection sensor 36, and the odiferous gas sensor 26.

If no cleaning of the flush toilet 2 is performed for a predetermined time after use of an alcoholic disinfectant has been detected by the seat disinfection detecting means and a test subject has sat on the seat, disinfection noise responding means built in the data analyzer 60 transmits a signal to the toilet cleaning device 46 to automatically perform toilet cleaning. In addition, if use of an alcoholic disinfectant has been detected by the seat disinfection detecting means, the disinfection noise responding means allows the suction fan 18c to increase its rotation speed. Accordingly, the amount of gas sucked by the suction device 18 increases to allow alcohol components volatilized while the seat is disinfected to be actively deodorized by the deodorant filter 78, thereby enabling a detection value of the odiferous gas sensor 26 to be reduced. That is, when the seat disinfection detecting means detects disinfection, the disinfection noise responding means operates a deodorizing device and reduces influence of noise caused by an alcoholic disinfectant. The seat disinfection detecting means and disinfection noise responding means are configured by electric circuits built in the data analyzer 60.

In a state where use of an alcoholic disinfectant is detected by the seat disinfection detecting means, and a detection value of the odiferous gas sensor 26 increases, the disinfection noise responding means stops measurement of physical condition, and allows the display device 68 to display a message of waiting for defecation to notify a test subject of the message. The disinfection noise responding means allows the display device 68 to display a message of waiting for defecation until the measurement of physical condition becomes possible to the test subject, to notify the test subject of the message. Accordingly, influence of noise caused by the alcoholic disinfectant is reduced. Meanwhile, a detection value of the odiferous gas sensor 26, which steeply increases by use of the alcoholic disinfectant, starts decreasing when the test subject finishes disinfection.

If a noise level detected by the odiferous gas sensor 26 is reversed to a downward tendency, the disinfection noise responding means deletes the message of waiting for defecation displayed in the display device 68 to notify the fact that the measurement becomes possible. That is, in a state where a noise level caused by an alcoholic disinfectant is in a downward tendency, it is possible to detect a rising edge of a detection value of the odiferous gas sensor 26, in the downward tendency. The data analyzer 60 detects a time point when a detection value of the odiferous gas sensor 26 in the downward tendency rises, as discharge of defecation gas by a test subject. In a state where the noise level detected by the odiferous gas sensor 26 decreases at a predetermined rate of change or more, the disinfection noise responding means stops the measurement of physical condition, and continues display of the message of waiting for defecation. This is because in a state where the noise level steeply decreases, a rise of a detection value by discharge of defecation gas is masked so that it is impossible to accurately detect discharge of defecation gas. In addition, it is desirable to stop calculation in a state where a reference value greatly decreases, because an error also may increase.

If a noise level is a predetermined value or more due to use of an alcoholic disinfectant, the disinfection noise responding means stops measurement of physical condition, or sets reliability of measurement to be low. As described above, if the reliability of measurement is reduced, a plotted point in the physical condition display table described in FIG. 7A is corrected to be more greatly displaced toward a region showing good physical condition. That is, if disinfection to the seat is detected, the disinfection noise responding means corrects determination of physical condition to be outputted by the display device 68 toward the region showing good physical condition.

Meanwhile, if many stools are attached to the flush toilet 2, or a large amount of aromatics are used, an absolute value of the amount of gas detected by the odiferous gas sensor 26 increases, so that a detection value of the sensor may be saturated in some cases, or measurement accuracy may be out of a high measurement accuracy band. In this kind of state, it is difficult to accurately estimate a trace amount of odiferous gas. Thus, the data analyzer 60 performs no measurement of physical condition, or reduces reliability of measurement also in a case where an absolute amount of a reference value is a third stability threshold value or more.

In the database of the server 12, as described above, measurement data on the amount of odiferous gas and the amount of healthy-state gas of an additional test subject is sequentially accumulated. In addition, in the database of the server 12, a medical examination result for cancer acquired when a test subject has a medical examination at a medical facility is stored from the medical facility terminal 16 by being associated with identification information on the test subject. The server 12 updates a stored diagnosis table on the basis of this kind of medical examination result for cancer, and change in history of change in the amount of odiferous gas and healthy-state gas.

FIG. 11 shows an example of update of the diagnosis table. For example, it is assumed that analysis performed by plotting measurement data A on odiferous gas and healthy-state gas of a test subject in an old diagnosis table results in determination of the "suspicion of early colorectal cancer" is determined, and the test subject is diagnosed as early colorectal cancer by medical examination. In this kind of case, as shown in FIG. 11, the respective regions, "large suspicion of colorectal cancer", "large suspicion of early colorectal cancer", and "suspicion of early colorectal cancer", are enlarged so as to include a portion corresponding to the measurement data A on the test subject diagnosed as early colorectal cancer, and the region, "insufficient physical condition level" is narrowed. Conversely, for example, in a case where there are many test subjects diagnosed as no suspicion of cancer by results of medical examination even if it is determined that the test subjects are in the region, "suspicion of early colorectal cancer" in an old diagnosis table from a correlation between the amount of odiferous gas and that of healthy-state gas, the region, "insufficient physical condition level" is enlarged, and the respective regions, "large suspicion of colorectal cancer", "large suspicion of early colorectal cancer", and "suspicion of early colorectal cancer" are narrowed. If the diagnosis table is updated, each of the regions in the display table is also changed.

The server 12 also stores attribute information on a test subject, such as weight, age, and sex, and a plurality of physical condition display tables classified according to a tendency of history of change in measurement data on odiferous gas and healthy-state gas.

If more detailed analysis of physical condition is requested in the test subject-side device 10, identification information on a test subject as well as attribute information on the test subject, such as weight, age, and sex, is registered in the server 12. When measurement data on a test subject requesting such detailed analysis is accumulated in the server 12, the server 12 selects a physical condition display table of conditions close to attribute information on the test subject, and history of change in measurement data. The server 12 then transmits the selected physical condition display table to the test subject-side device 10 through a network. When receiving an additional physical condition display table from the server 12, the test subject-side device 10 changes a physical condition display table that is already stored to the received physical condition display table. Accordingly, it is possible to perform accurate analysis of physical condition in accordance with the attribute of the test subject and the history of measurement data in the test subject-side device 10.

Although the embodiment described above is configured to store history of measurement data also in the test subject-side device 10, besides this, the measurement data may be stored in only the database of the server 12 so that the test subject-side device 10 reads out history of previous measurement data from the database of the server 12 to perform calculation of results of medical examination and time-dependent diagnosis in step S5 of medical examination.

Hereunder, a calculation method of the reliability in step S5 of medical examination in FIG. 4 is described in detail. As a characteristic of a semiconductor gas sensor used as the odiferous gas sensor 26, the sensor may detect not only odiferous gas but also surrounding stink gas of an aromatic, a disinfecting sheet and the like and stink gas attached to the body and clothes of a test subject. In addition, the detection value of odiferous gas detected by the semiconductor gas sensor varies depending on a state of a stool (whether the stool is diarrhea or not, for example), and an amount of stool. Consequently, in determining a disease concerning cancer, it is required to be able to evaluate the degree of influence of noise of stink gases, and the state of a stool. In the present embodiment, the reliability determination circuit provided in the data analyzer 60 in the test subject-side device 10 installed in the toilet installation room evaluates influence of noise of stink gas on the defecation gas, and the matter that exerts influence on precision of measurement, such as the state of a stool, and determines measurement reliability as an index indicating precision of detection of gas by the gas detector 20. The reliability determination circuit is configured by an electric circuit built in the data analyzer 60.

Figure 12:
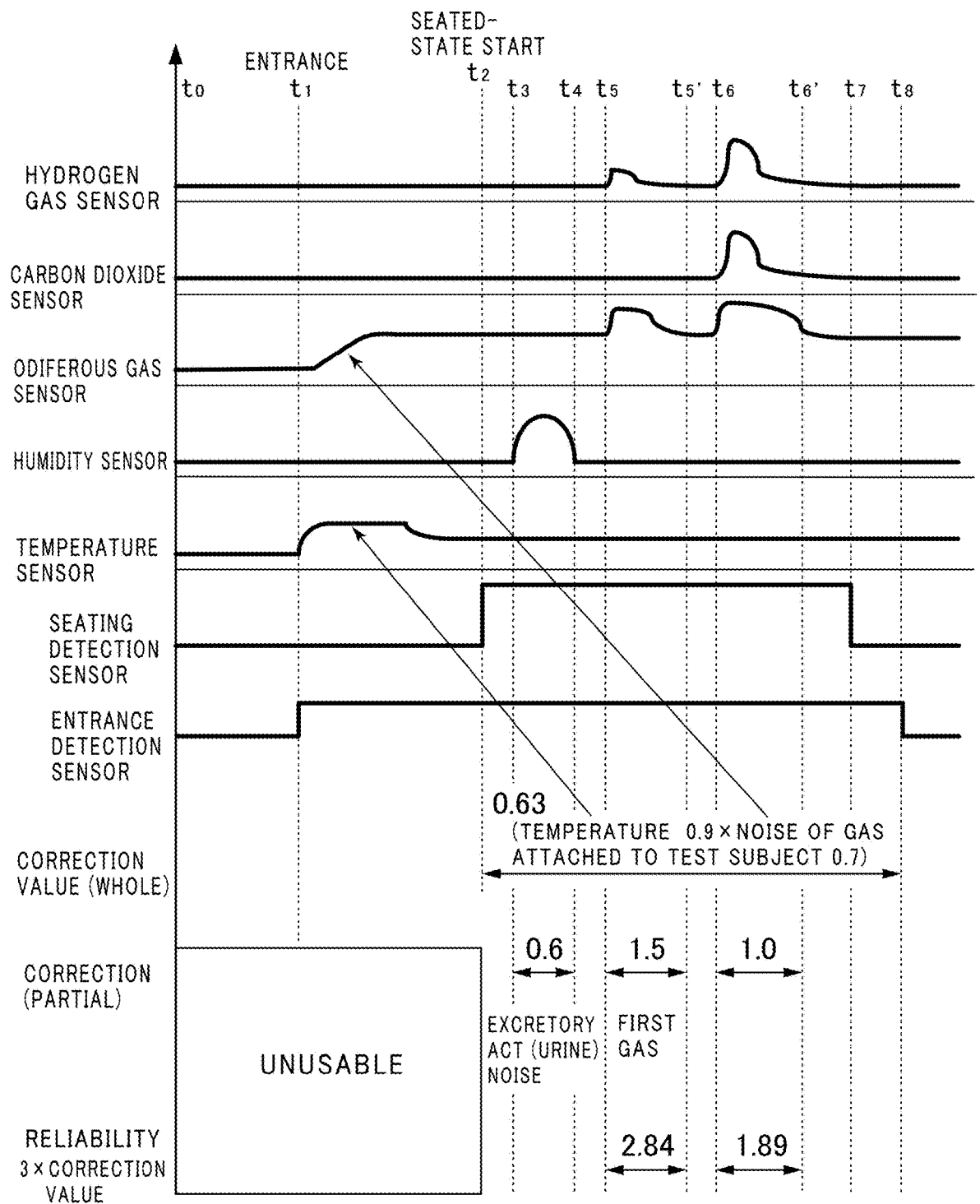
FIG. 12 is a diagram for explaining a method for determining reliability of measurement.

FIG. 12 is a diagram for explaining a method for determining measurement reliability. In the following explanation, a case in which correction by influence of stink gas attached to the body and clothes of a test subject, influence of humidity, influence of temperature, and influence of a frequency of defecation gas is performed is explained as an example. Determination of measurement reliability as follows is performed by using the reliability determining means that determines reliability of detection of odiferous gas in the data analyzer 60 of the remote control 8.

Outputs from the hydrogen gas sensor 24, the odiferous gas sensor 26, the carbon dioxide sensor 28, the humidity sensor 30, the temperature sensor 32, the entrance detection sensor 34, the seating detection sensor 36, and the defecation/urination detection sensor 38 of the measuring device 6 are transmitted to the data analyzer 60 of the remote control 8. FIG. 12 shows examples of the outputs from the sensors.

Further, the data analyzer 60 of the remote control 8 stores a plurality of reliability correction tables for calculating reliability, in advance.

FIG. 13 to FIG. 16 are respectively diagrams showing a correction table of noise of stink gas attached to a test subject for determining influence of stink gas attached to a body and clothes of a test subject, a humidity correction table for determining influence of humidity, a temperature correction table for determining influence of temperature, and an excretion frequency correction table for determining influence by a frequency of excretion.

Figure 13:
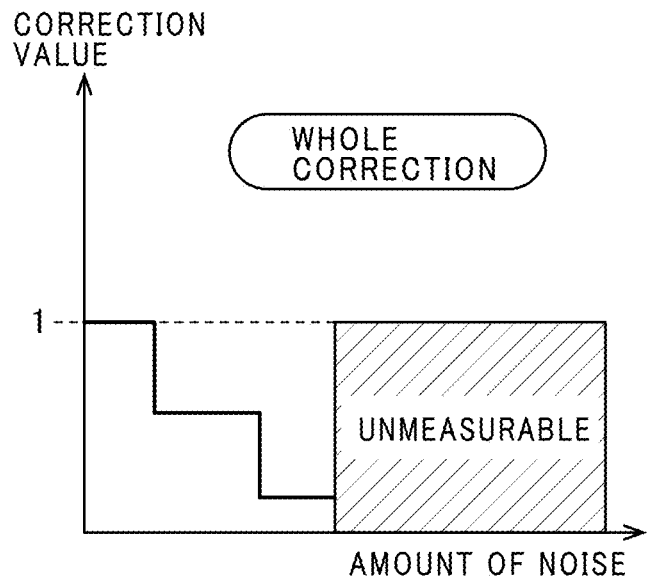
FIG. 13 is diagram showing a correction table of noise of odiferous gas attached to a test subject for determining an influence of the odiferous gas attached to a body and clothes of the test subject.

The semiconductor gas sensor used as the odiferous gas sensor 26 detects noise of stink gas (environmental noise) other than defecation gas, that is attached to the test subject. When an amount of component of stink gas (noise amount) attached to the test subject is large, reliability of measurement can be said as low. Consequently, as shown in FIG. 13, in the correction table of noise of stink gas attached to a test subject, a correction value is set to an amount of noise of attached stink gas. Specifically, the correction value is set as 1 as the value for performing no correction when the amount of component of stink gas attached to the test subject is less than a predetermined value. When the amount of component of stink gas attached to the test subject is a predetermined amount or more, the correction amount subtracted from one is increased because as the amount of stink gas component is larger, the reliability value becomes gradually lower, and when the noise amount of the component of stink gas attached to the test subject is excessively larger than the predetermined amount, measurement is determined as impossible (the correction value of 0). The amount of noise of attached stink gas is determined on the basis of detection data detected by the odiferous gas sensor 26 in a non-defecation period before the seating detection sensor 36 detects that the test subject sits on the seat. Reliability is corrected for an entire defecation period, because the component of stink gas attached to the test subject affects the entire defecation period instead of a part of the defecation period. Hereunder, correcting reliability for the entire defecation period in this way is referred to as "overall correction".

Figure 14:
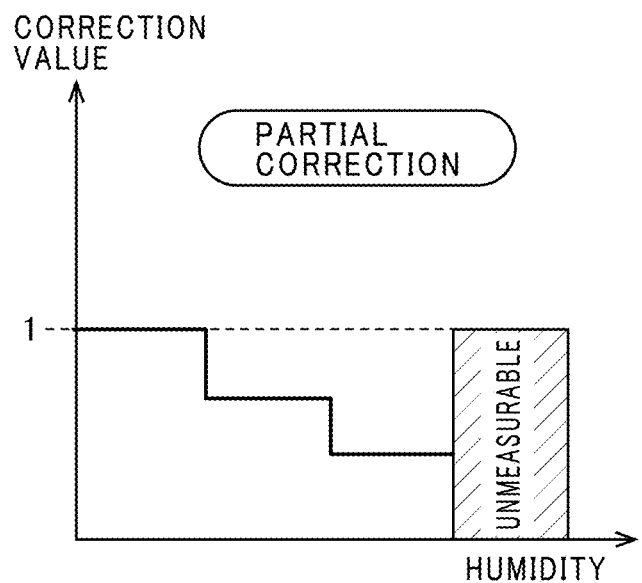
FIG. 14 is a diagram showing a humidity correction table for determining an influence of humidity.

Further, when a test subject urinates, humidity in the bowl 2a rises, and humidity of gas that reaches the catalyst of the odiferous gas sensor 26 becomes high. When the humidity of the gas that reaches the odiferous gas sensor 26 becomes high, resistance of the odiferous gas sensor 26 changes, and sensitivity of the sensor is reduced. Further, if urine splashes on a stool attached to the inside of the bowl 2a, the attached stool is softened from a dried state, and much defecation gas may be temporarily released again from the attached stool while urine splashes into the bowl 2a. The defecation gas released from the attached stool is likely to be detected by the odiferous gas sensor as noise when the defecation gas emitted from the test subject is measured. Consequently, as shown in FIG. 14, in the humidity correction table, a correction value is set at 1 when humidity measured by the humidity sensor 30 is lower than a predetermined value. When the humidity is at the predetermined value or more, reliability becomes lower as humidity becomes higher, and when humidity is at a measurement limit value or more, measurement is determined as impossible (correction value of 0). Since a urination act is a temporary act, the humidity correction table sets "partial correction" correcting only a period in which a change in humidity measured by the humidity sensor 30 is seen. Hereunder, correcting reliability in only a specific period in the defecation period like this, or making different correction in each of periods in the defecation period although correction is made in the entire defecation period is referred to as "partial correction".

Figure 15:
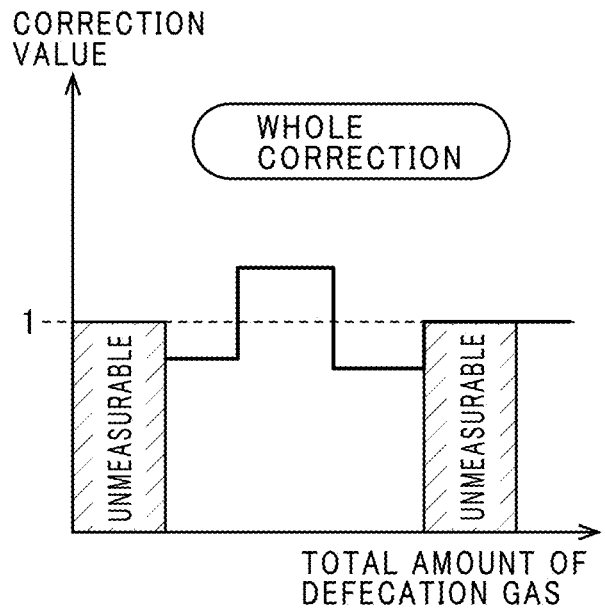
FIG. 15 is a diagram showing a temperature correction table for determining an influence of a temperature.

Further, the semiconductor gas sensor used as the odiferous gas sensor 26 detects odiferous gas on the basis of oxidation-reduction reaction between oxygen adsorbed on a surface and reducing gas, in a state in which a catalyst composed of tin oxide is heated. Consequently, when a temperature of the catalyst is higher or lower than a predetermined temperature range, sensitivity of the sensor is reduced. Consequently, as shown in FIG. 15, in the temperature correction table, a correction value is set in accordance with a temperature detected by the temperature sensor 32. Specifically, when the temperature detected by the temperature sensor 32 is within a suitable temperature suitable for measurement of the catalyst of the odiferous gas sensor 26, the correction value is set as a value larger than 1 to enhance reliability. When the temperature detected by the temperature sensor 32 is in a range slightly higher or lower than the suitable temperature range, the correction value is set as a value less than 1 to reduce a reliability value. Further, when the temperature detected by the temperature sensor is in a range larger than an upper limit value of a measurable temperature, or is smaller than a lower limit value of the measurable temperature, measurement is determined as impossible (correction value of 0). Temperature correction is set as overall correction correcting the entire defecation period, because temperature does not vary greatly in a defecation period.

Figure 16:
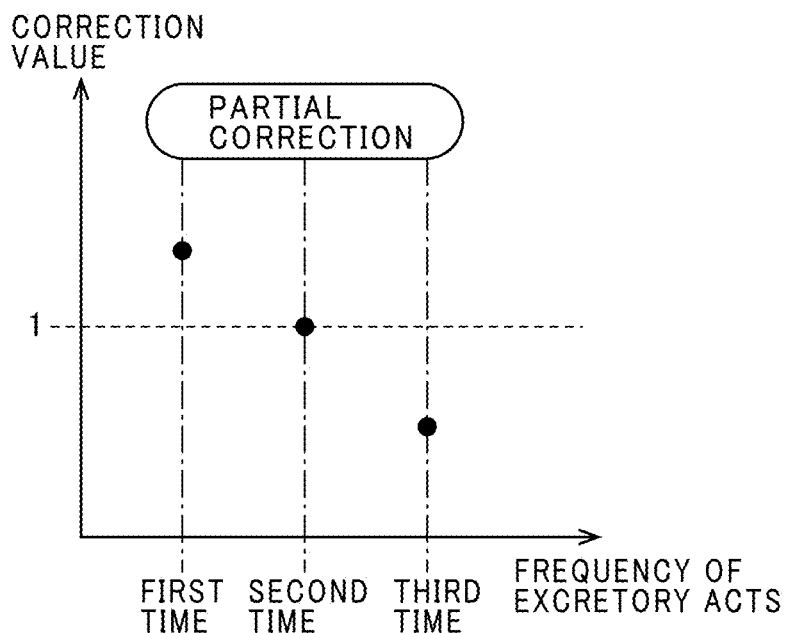
FIG. 16 is a diagram showing a correction table of a frequency of excretion for determining an influence of the frequency of excretion.

Further, when an excretory act is performed a plurality of times during one defecation period, an amount of defecation gas itself is large (an amount of odiferous gas is also large) at the first time, so that precision of analysis is higher in the excretory act of an initial stage of the defecation period than in an excretory act at a latter stage. Consequently, as shown in FIG. 16, in the excretory act frequency correction table, a correction value of the defecation gas of the initial time is set at a value larger than 1 to increase reliability. A correction value of the second time is set as 1, a correction value of the third time or later is set as a value less than 1, and as the frequency increases, the correction value is gradually reduced. Thereby, it is devised that defecation gas of the first time preferentially becomes an object to be diagnosed. The excretory act frequency correction table is for correcting only a period in which defecation gas is detected, and makes partial correction.

When entrance of a test subject is detected by the entrance detection sensor 34 at time $t_1$ as shown in FIG. 12, the control device 22 of the measuring device 6 is shifted from the step of improving environment before measurement that is a waiting state to the step of preparing starting measurement, and allows the sensor heater 54 and the suction device 18 to drive. Thereby, the temperature detected by the temperature sensor 32 increases, and converges to a proper temperature. Subsequently, the data analyzer 60 of the remote control 8 refers to the temperature correction table, and acquires a correction value corresponding to the convergence temperature measured by the temperature sensor 32, in a non-defecation period before the seating detection sensor 36 detects that the test subject sits on the seat. In an example shown in FIG. 12, the temperature correction value is 0.9.

Further, when the test subject enters the toilet installation room at time $t_1$, detection data detected by the odiferous gas sensor 26 increases due to noise of stink gas attached to the test subject, and thereafter converges to a fixed value. Subsequently, seating is detected by the seating detection sensor 36 at time $t_2$. The data analyzer 60 of the remote control 8 obtains a correction value corresponding to detection data measured by the odiferous gas sensor 26 in the non-defecation period before detection of seating by the seating detection sensor 36. In the present embodiment, the correction value of noise of stink gas attached to the test subject is 0.7.

Next, when the test subject urines at time $t_3$, in a defecation period after the seating detection sensor 36 detects that the test subject sits on the seat, a detection value by the humidity sensor 30 increases. Detection of increase in humidity by the humidity sensor 30 can be measured with the humidity before the defecation period, that is, before the seating detection sensor 36 detects that the test subject sits on the seat, as a reference, for example. In this way, when increase in the detection data is detected by the humidity sensor 30, the data analyzer 60 refers to the humidity correction table, and finds a correction value corresponding to the increased detection data, with respect to a period in which the detection data increases. In the present embodiment, a partial correction value in the period (that is, times $t_3$ to $t_4$) in which the detection data by the humidity sensor 30 increases is 0.6.

Next, when the test subject performs excretory acts at times $t_5$ and $t_6$, and thereby a rate of change of difference between detection data detected by the odiferous gas sensor 26 and a reference value becomes a predetermined value or more, the data analyzer 60 calculates amounts of gas by the excretory acts. Further, with this, the data analyzer 60 refers to the frequency correction table in accordance with the frequency of an excretory act in the defecation period, and sets the correction value at 1.5 in a period (that is, times $t_5$ to $t_5'$) corresponding to the first excretory act, and sets the correction value at 1.0 in a period (that is, times $t_6$ to $t_6'$) corresponding to the second excretory act.

The data analyzer 60 calculates measurement reliability of detection of gas by each of the excretory acts on the basis of the overall correction value and the partial correction value that are estimated in this way. In the present embodiment, reliability is based on 3, and reliability to each of excretory acts is calculated as 3×product of all of overall correction values×product of all of corresponding partial correction values. Specifically, reliability of the first excretory act is 3 (reference)×0.9 (temperature correction value)×0.7 (correction value of noise attached to test subject×1.5 (frequency correction value)=2.84. Further, reliability of the second excretory act is 3 (reference)×0.9 (temperature correction value)×0.7 (correction value of noise attached to test subject×1.0 (frequency correction value)=1.89.

Subsequently, the reliability calculated in this way is displayed in the display device 68 of the remote control 8, as described with reference to FIG. 5. Further, the calculated reliability is transmitted to the server 12 from the test subject-side device, with detection data of the odiferous gas sensor 26 and detection data of the hydrogen gas sensor 24, and is recorded in the defecation gas database of the server 12. At this time, as for the detection data of the odiferous gas sensor and the detection data of the hydrogen gas sensor, raw data that are not subjected to correction based on reliability that is described later are stored in the defecation gas database of the server 12. When measurement data is browsed at the medical facility terminal 16 connected to the server 12, the measurement reliability is displayed with the detection data of the odiferous gas sensor 26 and the detection data of the hydrogen gas sensor 24. A doctor in a medical facility performs diagnosis with reference to the measurement reliability displayed with the odiferous gas and hydrogen gas displayed in the medical facility terminal 16. Thereby, when a doctor or the like performs diagnosis of physical condition of a test subject on the basis of the measurement data, the doctor or the like can perform more accurate diagnosis by using data with high measurement reliability. Further, a doctor may perform diagnosis without using or attaching importance to data with low measurement reliability. When reliability of a partial or entire period of the measurement data is 1 or less, measurement precision is so low so that measurement may be determined as impossible and measurement data may not be transmitted to the server 12.

Further, it is also possible to correct detection data of the odiferous gas sensor 26 and the hydrogen gas sensor 24 on the basis of the measurement reliability which is calculated in this way. Specifically, when the measurement reliability is high, actual detection values are used, but when the measurement reliability is low, the detection values are corrected to be values close to the previous detection values. As an example, a case is described, in which when physical condition is analyzed on the basis of the detection data of defecation gas by the defecation act of the first time in the test subject-side device 10, a detection value newly detected is corrected so as to be close to the previous measurement data stored in the storage device of the remote control 8. As described above, reliability accompanying the excretory act of the first time is calculated as 2.84.

Figure 17:
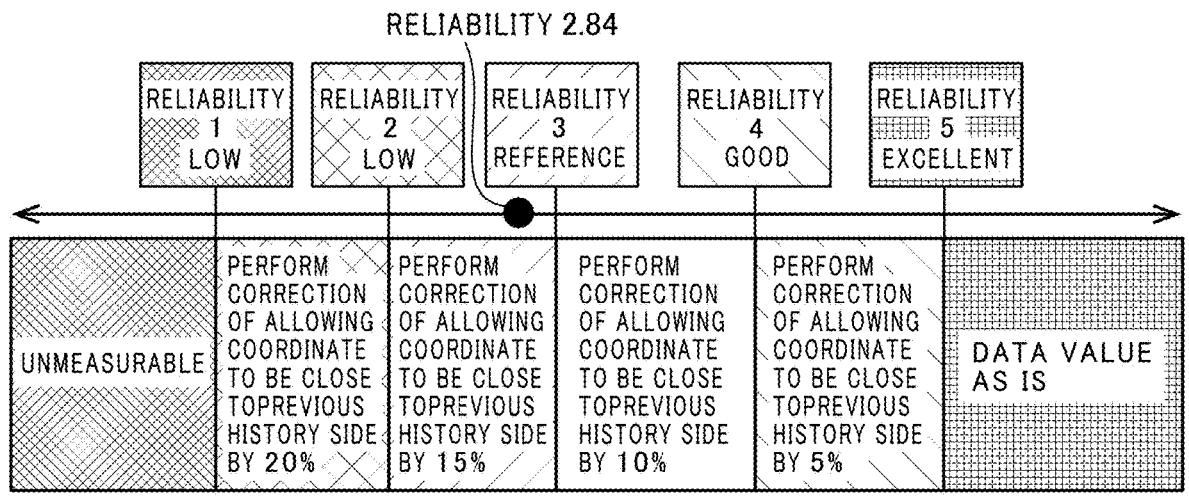
FIG. 17 is a diagram showing a correction table showing a relationship between reliability recorded in a data analyzer and a correction factor of a measurement value.

The data analyzer 60 determines the correction amount of a measurement value on the basis of reliability that is calculated in this way. FIG. 17 is a diagram showing a correction table showing a relationship between reliability stored in the data analyzer, and a correction factor of a measurement value. As shown in FIG. 17, when the reliability is 1 or less, the measurement value is determined as unusable because reliability of detection data is excessively low, in the present embodiment. That is, analysis of physical condition is not performed on the basis of detection data in a period in which the reliability is a predetermined value or less, but analysis is performed on the basis of only detection data with reliability larger than the predetermined value, and an analysis result is displayed in the display device 68. Further, when reliability is larger than 1 and is equal to 2 or less, correction that brings a measurement value close to a past history region by 20% is carried out. Further, when the measurement value has reliability larger than 2 and equal to 3 or less, correction that brings the measurement value close to the past history region by 15% is carried out. Further, when reliability is larger than 3 and is 4 or less, correction of bringing the measured value close to the past history side by 10% is carried out. Further, when reliability is larger than 4 and is equal to 5 or less, correction of bringing the measured value to the past history region by 5% is carried out. Further, when the measurement value is larger than 5, the measurement value is used without being corrected.

In the above described example, reliability accompanying the excretory act of the first time is 2.84. Consequently, as described with reference to FIG. 7A, correction that brings a plotted point of the latest data close to the previous measurement value by 15% is performed, and the corrected measurement value is displayed with the previous data.

Correction based on reliability like this may be performed on the side of the server 12. Further, when analysis of physical condition is performed on the side of the server 12, detection values of odiferous gas and detection values of hydrogen gas of defecation acts with reliability of a predetermined value or more in a defecation period of one time are totaled, for example, and analysis of physical condition may be performed on the basis of the totaled data. Further, detection data that is stored in the storage device of the remote control 8 does not have to be detection data that is not subjected to correction based on measurement reliability, but detection data after correction may be stored.

The correction tables are not limited to the correction table of noise of stink gas attached to a test subject, the temperature correction table and the humidity correction table. FIG. 18 to FIG. 29 are diagrams showing examples of the correction table.

Figure 18:
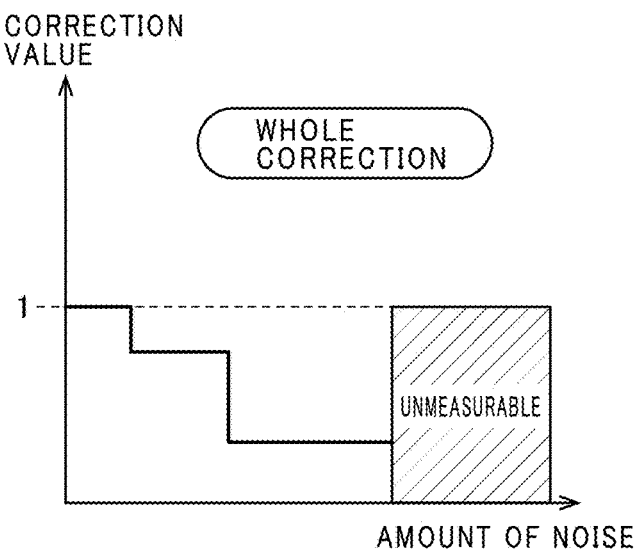
FIG. 18 is a diagram showing an environmental noise correction table.

For example, when stink gas noise (environmental noise) other than defecation gas, such as an aromatic is present in a toilet installation room, the odiferous gas sensor 26 may detect the stink gas noise, and precision of measurement may be reduced. Thus, the data analyzer 60 corrects reliability to evaluate influence of environmental noise. An amount of environmental noise like this can be evaluated on the basis of detection data by the odiferous gas sensor 26 before entrance of a test subject is detected by the entrance detection sensor 34, for example. FIG. 18 is a diagram showing an environmental noise correction table. As shown in FIG. 18, the environmental noise correction value is 1 when an amount of environmental noise is smaller than a predetermined value, and a correction factor is also decreased because a reliability value becomes lower as the amount of environmental noise increases to be the predetermined value or more. When the amount of environmental noise is a measurable upper limit value or more, measurement is determined impossible. Overall correction can be performed because the environmental noise correction value affects an entire defecation period.

Figure 19:
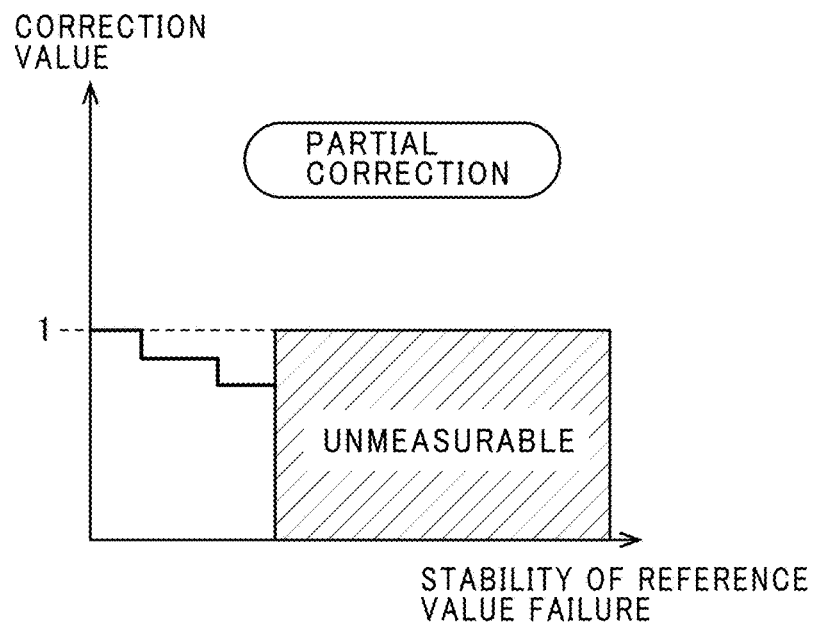
FIG. 19 is a diagram showing a reference value stability correction table.

Further, when detection data of the odiferous gas sensor 26 varies greatly at the time of setting a reference value, and when a gradient of the set reference value is large at the time of estimation of an amount of gas, in a case of using a spray aromatic, for example, precision of the estimated amount of gas is reduced. Thus, the data analyzer 60 refers to a reference value stability correction table, and corrects reliability in order to evaluate influence of a wrong state of reference value stability like this (referred to as a reference value stability failure). Reference value stability can be evaluated on the basis of the gradient of a reference value to a time axis in a non-defecation period, and a magnitude of variation of the detection value of the odiferous gas sensor 26 at the time of setting the reference value, for example. FIG. 19 is a diagram showing the reference value stability correction table. As shown in FIG. 19, a reference value stability noise correction value is 1 when a reference value stability failure is small, and becomes smaller as the reference value stability failure becomes larger. When the reference value stability failure is a predetermined value or more, measurement is determined as impossible. For estimation of an amount of gas, a reference value is set to each of excretory acts, so that a correction value for only a period corresponding to each of excretory acts, that is, partial correction is applied.

Figure 20:
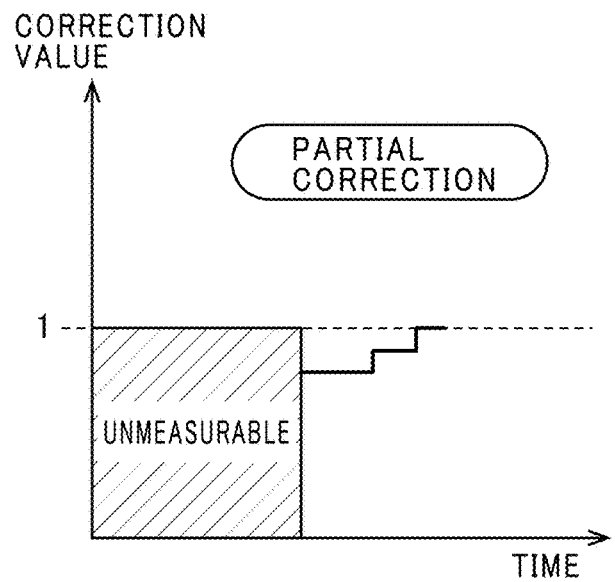
FIG. 20 is a diagram showing a disinfection toilet seat cleaning correction table.

Further, when a toilet seat is cleaned with a disinfecting sheet, for example, the odiferous gas sensor 26 detects a component such as alcohol contained in the disinfecting sheet. As an influence of the component such as alcohol contained in the disinfecting sheet, a large value is detected in the odiferous gas sensor 26 immediately after the disinfecting sheet is used, but the value detected by the odiferous gas sensor 26 is decreased in a short period because alcohol has high volatility. Thus, the data analyzer 60 refers to a disinfection toilet seat cleaning correction table, and corrects reliability in accordance with an influence by disinfection of the toilet seat. Use of the disinfecting sheet can be detected by detecting that the detection data of the odiferous gas sensor 26 greatly varies from a predetermined value after the entrance detection sensor 34 detects that a test subject enters the toilet installation room and before the seating detection sensor 36 detects that the test subject sits on the seat, for example. FIG. 20 is a diagram showing a disinfection toilet seat cleaning correction table. When use of the disinfecting sheet is detected in this way, measurement is determined as impossible (correction value of 0) in a predetermined period from detection of the disinfecting sheet, and a correction value in the following period increases to 1 with a lapse of time from a value less than 1. Partial correction is made because the influence of a disinfecting sheet changes depending on time as described above.

Figure 21:
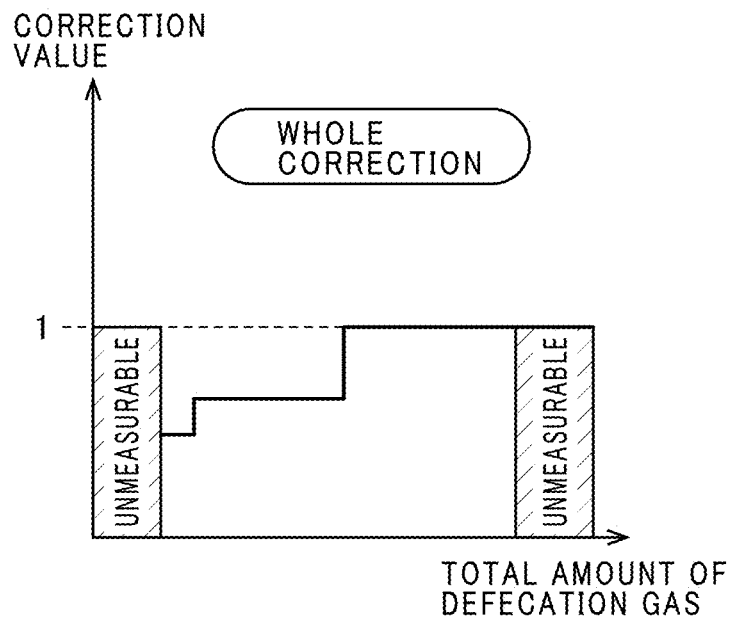
FIG. 21 is a diagram showing a defecation gas total amount correction value table.

Further, since only a minute trace of odiferous gas is contained in defecation gas, more accurate analysis on physical condition can be performed as an amount of odiferous gas discharged in a defecation period is larger. Consequently, the data analyzer 60 refers to a defecation gas total amount correction value table, and corrects reliability on the basis of a total amount of odiferous gas. A total amount of defecation gas can be evaluated based on a total of amounts of gas estimated on the basis of detection data of the odiferous gas sensor in a defecation period. FIG. 21 is a diagram showing the defecation gas total amount correction value table. As shown in FIG. 21, concerning the defecation total amount correction value, when the total amount of defecation gas is a predetermined value or more, it is determined that a certain problem has occurred such as spraying an aromatic spray during measurement, and measurement is determined as impossible (correction value of 0). Further, when the total amount of defecation gas is the predetermined value or less, it is determined that an amount of defecation gas is so small that accurate measurement cannot be performed, and measurement is determined as impossible (correction value of 0). In a range in which measurement is not determined as impossible (correction value of 0), the correction value is set as 1 when the total amount of defecation gas is large, and the correction value becomes smaller as the total amount of defecation gas becomes smaller. Overall correction is performed for correction of the total amount of defecation gas, because the correction value is set on the basis of the total amount of defecation gas in the entire defecation period.

Figure 22:
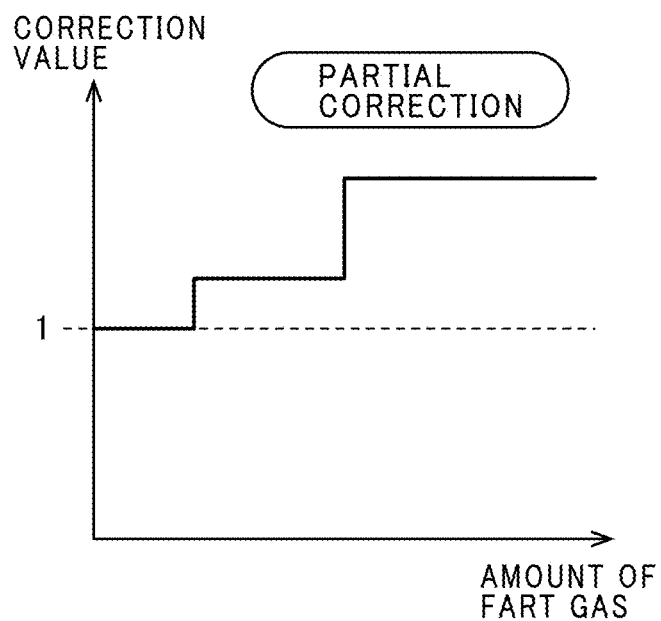
FIG. 22 is a diagram showing a fart correction value table.

Further, at a time of farting, a larger amount of defecation gas is released into the bowl than at a time of defecation, and therefore the defecation gas by farting is suitable for analysis of physical condition. Consequently, when a fart by a test subject is detected, the data analyzer 60 refers to a fart correction value table, and corrects reliability in a period of the fart on the basis of an amount of defecation gas included in the fart. As for a faring act, it can be determined that a farting act is performed when it is detected that a difference between a detection value of the odiferous gas sensor 26 and the reference value steeply increases with a rate of change of a predetermined value or more, after the seating detection sensor 36 detects that the test subject sits on the seat. Further, a period from a point of time when the above described difference steeply increases until the detection value of the gas sensor 26 returns to the reference value again may be set as a fart period. In order to detect that a fart act has been performed more accurately, it is sufficient to detect that detection data of the odiferous gas sensor 26 steeply increases with a rate of change of a predetermined value or more, and no stool is discharged into the bowl by a seal water amount sensor or the like. FIG. 22 is a diagram showing the fart correction value table. As shown in FIG. 22, in the fart correction value table, a correction value is 1 when an amount of fart gas (an amount of defecation gas detected by the odiferous gas sensor) is small, and the correction value can be set so that as the amount of fart gas increases, the correction value increases.

Figure 23:
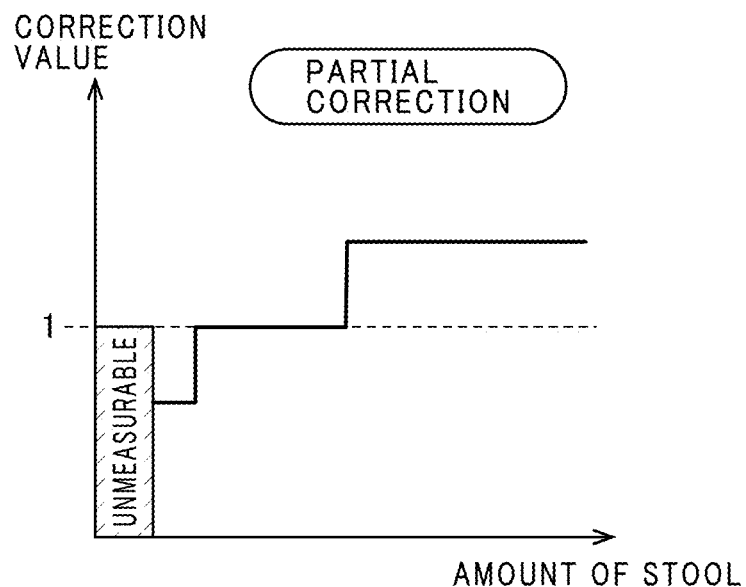
FIG. 23 is a diagram showing a stool amount correction value table.

Further, when an amount of stool in each of excretory acts is large, an amount of defecation gas is large, and more accurate analysis of physical condition can be performed, whereas when the amount of stool in each of excretory acts is small, an amount of defecation gas is small, and precision of analysis of physical condition becomes low. Thus, the data analyzer 60 refers to a stool amount correction value table, and corrects reliability on the basis of the amount of stool at a time of each of excretory acts. The amount of stool can be evaluated by a seal water amount sensor (stool amount measuring device) that detects a change in an amount of seal water, of the defecation/urination detection sensor 38, for example. FIG. 23 is a diagram showing the stool amount correction value table. As shown in FIG. 23, when an amount of stool is a predetermined value or less, it is determined that the amount of defecation gas as well as the amount of stool is very small, and accurate analysis cannot be performed, so that measurement is determined as impossible. When the amount of stool exceeds the predetermined value, a correction value gradually increases from a value less than 1 to a value exceeding 1 as the amount of stool increases. The stool amount correction value is for partial correction because the amount of stool is determined for each excretory act.

Figure 24:
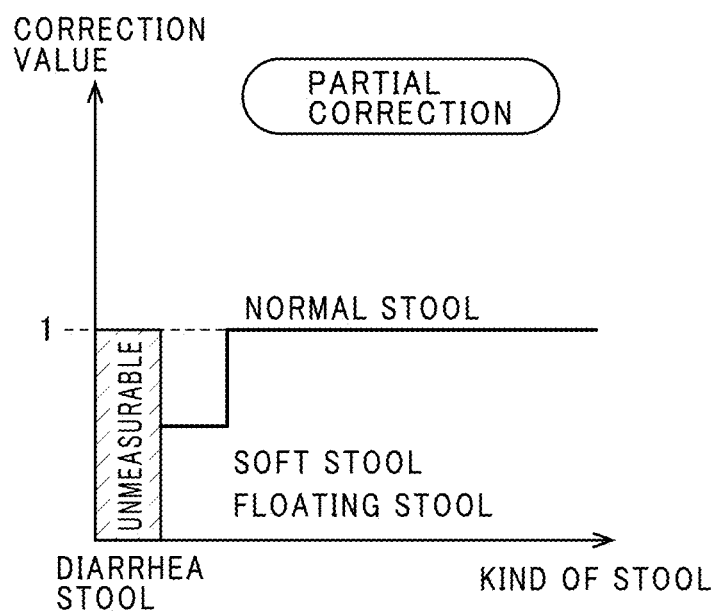
FIG. 24 is a diagram showing a stool type correction value table.

Further, when a stool is diarrhea, for example, the sensor cannot detect defecation gas sufficiently because a releasing time is short. Further, when a stool after defecation floats on seal water, defecation gas is released from the stool floating on the seal water, and detection precision of the defecation gas is reduced. Thus, the data analyzer 60 refers to a stool type correction table, and corrects reliability in accordance with a type of stool in each of excretory acts. The type of stool can be detected by using a CCD of the defecation/urination detection sensor 38, a microwave sensor and the like as a stool state detection device, and on the basis of detection results of these sensors. Further, float of a stool can be detected by installing a CCD, a microwave sensor and the like in the bowl as a float detection device. FIG. 24 is a diagram showing the stool type correction value table. As shown in FIG. 24, in the case of a diarrhea stool, measurement is determined as impossible (correction value of 0). When a floating stool is detected, a correction value in the following excretory acts is set as a value less than 1, and when a normal stool is detected, the correction value is set as 1. The stool type correction value is for partial correction, because the type of stool is determined in each excretory act.

Figure 25:
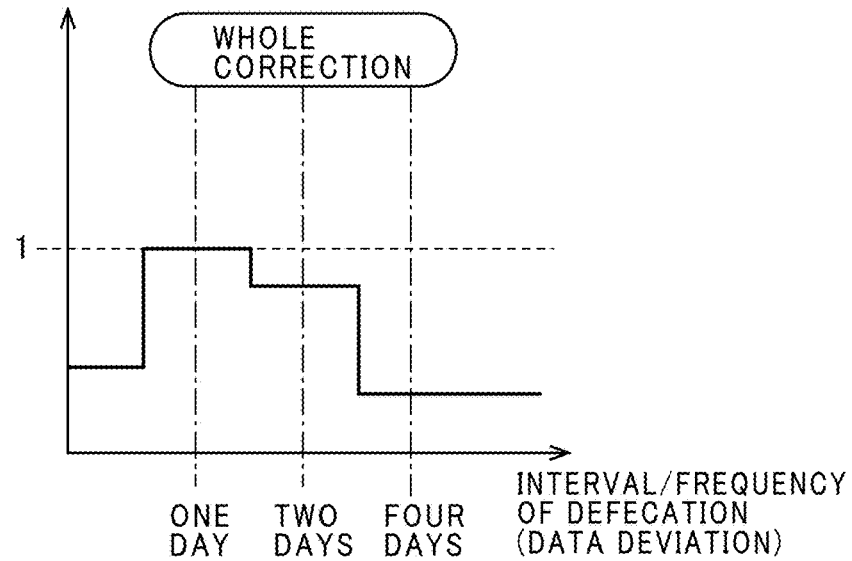
FIG. 25 is a diagram showing a defecation interval correction value table.

Further, healthy people usually defecate about once a day. On the other hand, when a person gets a poor gastrointestinal condition due to food poisoning or the like, it causes the person to defecate many times a day. In such a case, an amount of defecation gas released at the time of defecation becomes small even when defecation is performed. Further, when a defecation frequency decreases due to obstipation or the like, an amount of defecation gas increases for the reason that a generation time of stink gas components becomes long, the amount of stool increases, and the like. When an interval of defecations becomes too long, precision of analysis of physical condition is reduced. Thus, the data analyzer 60 refers to a defecation interval correction table, and corrects reliability on the basis of an interval of defecations. The interval of defecations can be determined on the basis of a date and time of defecation of the previous time stored by the data analyzer 60, and the defecation history information inputted in step S2 of preparing starting measurement. FIG. 25 is a diagram showing a defecation interval correction value table. As shown in FIG. 25, when the interval of defecations is extremely short, a correction value is set as a value extremely smaller than 1. When the interval of defecations is about a day, the correction value is set as 1. When the interval of defecations is about two days, the correction value is set as a value smaller than 1, and when the interval of defecations is four days or more, the correction value is set as a value extremely smaller than 1. The defecation interval correction value is for overall correction.

Figure 26:
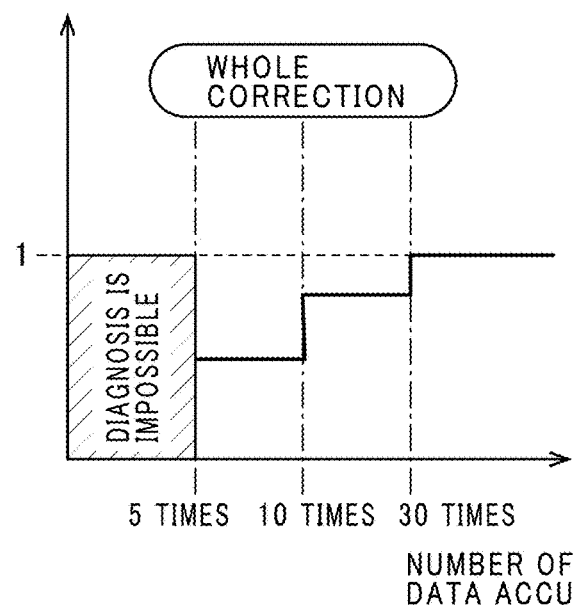
FIG. 26 is a diagram showing a data accumulation amount correction table.

In determination of physical condition based on defecation gas, physical condition is determined as worse than an original physical condition when gastrointestinal condition is worsened due to crapulence of the previous day, for example. Consequently, variations occur to the result of analysis of physical condition depending on daily life. Consequently, if days of bad physical condition due to crapulence and the like happen to overlap, at a point of time when analysis of physical condition by the biological information measurement system of the present embodiment is started, for example, only the analysis result with bad physical condition is displayed even when the history is displayed, and accurate determination of diseases may not be able to be performed in a medical facility or the like. Thus, the data analyzer 60 refers to a data accumulation amount correction table, and corrects reliability in accordance with the number of data of previous measurement data stored in the test subject-side device. FIG. 26 is a diagram showing the data accumulation amount correction table. As shown in FIG. 26, when the number of accumulation data is less than five, diagnosis is determined as impossible (correction value of 0). When the number of accumulation data is five or more, and is less than ten, the correction value is set as an extremely small value less than 1. When the number of accumulation data is 10 or more and is less than 30, the correction value is set as a small value less than 1, and when the number of accumulation data is 30 or more, the correction value is set as 1. The test subject-side device in the present embodiment is not a device diagnosing cancer, but a device intended to make a test subject aware of an increased risk of cancer with a change in physical condition and encourage the test subject to improve a living habit. Consequently, it is desirable to perform response like this to prevent an unnecessary mental burden, because measurement precision of each time is not high, but the history of change itself is the value of the device.

Figure 27:
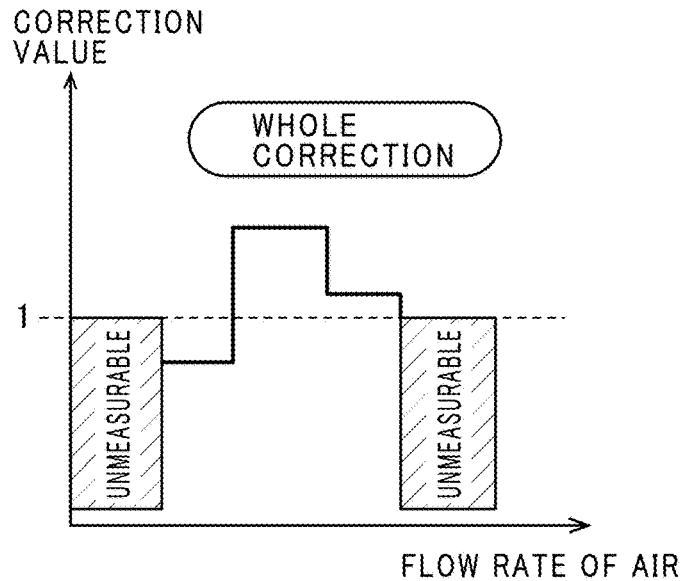
FIG. 27 is a diagram showing a gas flow amount correction value table.

When the filter 72 installed in the duct 18a is clogged, an amount of airflow sucked into the duct 18a is decreased. In relation with this, if an amount of flow of gas sent to the odiferous gas sensor 26 and the hydrogen gas sensor 24 changes, detection data of the odiferous gas sensor 26 and the hydrogen gas sensor 24 change in accordance with the amount of flow of gas. Further, when a velocity of flow of gas sent to the odiferous gas sensor 26 and the hydrogen gas sensor 24 is high, a time period in which the gas contacts the sensors is short, so that the catalysts of the sensors do not sufficiently react to the gas. Consequently, it is desirable that the amount of flow of gas sent to the odiferous gas sensor 26 and the hydrogen gas sensor 24 is constant. Consequently, the data analyzer 60 refers to a gas flow amount correction value table, and corrects reliability in accordance with the amount of flow (the velocity of flow) of gas sent to the odiferous gas sensor 26 and the hydrogen gas sensor 24. The amount of flow of gas can be estimated on the basis of a current and voltage of the suction fan 18c provided in the deodorizing device, for example. FIG. 27 is a diagram showing the gas flow amount correction value table. As shown in FIG. 27, in the gas flow amount correction table, measurement is determined as impossible (correction value of 0) when the amount of gas flow is less than a measurable lower limit value and is a measurable upper limit value or more. When the amount of flow of gas is within an optimum range, the correction value is set as a value larger than 1, and is set as a value close to 1 within a measurable range other than the optimum range. In the present embodiment, influence on sensor detection sensitivity by reduction in gas flow amount due to clogging is larger than in a case where an amount of gas flow is large, so that as for the correction value in a range higher than the optimum range within the measurable range, the correction value in a range lower than the optimal range is set to be low. Overall correction is made because the amount of flow of gas during measurement does not change greatly.

Figure 28:
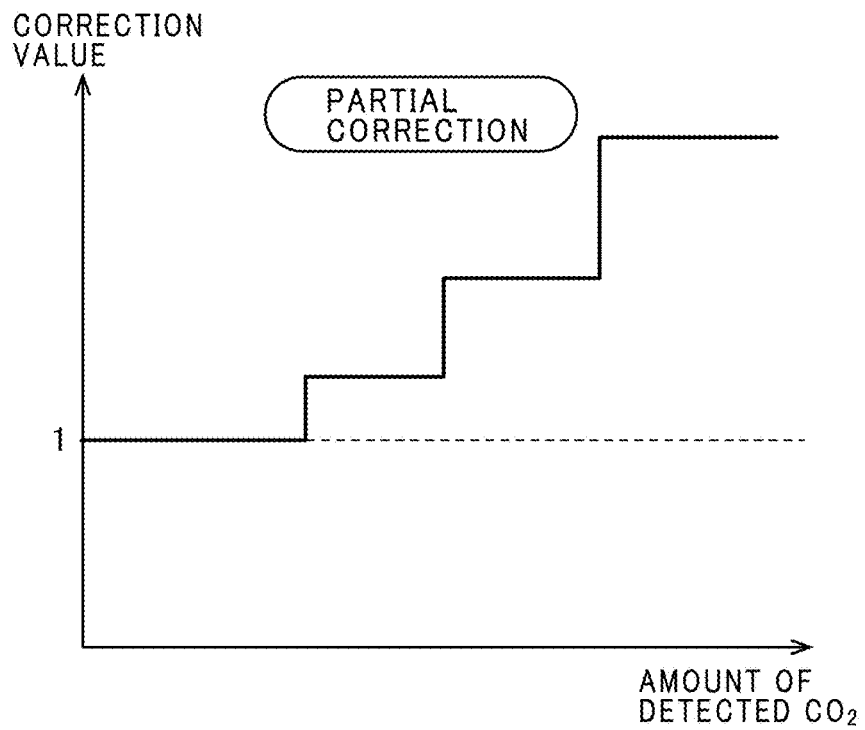
FIG. 28 is a diagram showing a $CO_2$ correction table.

Defecation gas includes $CO_2$ gas as healthy-state gas, as well as hydrogen gas. Consequently, when a large amount of $CO_2$ is detected by the $CO_2$ gas sensor, defecation gas is detected by the sensor device more reliably. Thus, the data analyzer 60 refers to a $CO_2$ correction table, and corrects reliability on the basis of detection data of $CO_2$ detected by the carbon dioxide sensor 28. FIG. 28 is a diagram showing the $CO_2$ correction table. As shown in FIG. 28, in the $CO_2$ correction table, a correction value is set at 1 when a detection amount of $CO_2$ is smaller than a predetermined value, and when the detection amount of $CO_2$ is the predetermined value or more, the correction value is made larger as the detection amount of $CO_2$ increases. Partial correction is made because the $CO_2$ correction value can be calculated for each of defecation acts. In this way, in the present embodiment, detected hydrogen gas is corrected on the basis of an amount of $CO_2$ gas, so that healthy-state gas is evaluated by using hydrogen gas and $CO_2$ gas.

Further, when physical condition is analyzed by using detection data of the $CO_2$ gas sensor as detection data of healthy-state gas, an $H_2$ correction table in which a correction value becomes larger as a detection value detected by the hydrogen gas sensor 24 becomes larger can be used, in place of the $CO_2$ correction table.

Figure 29:
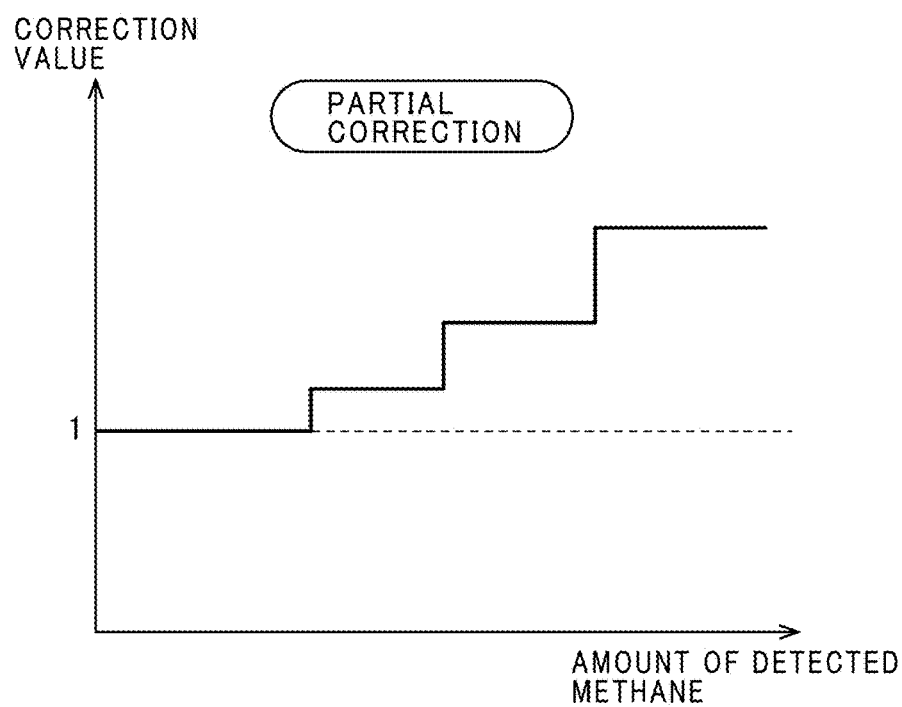
FIG. 29 is a diagram showing a methane gas correction table.

Defection gas contains methane as healthy-state gas, as well as hydrogen gas. Consequently, when a methane gas sensor that reacts strongly to methane gas is installed in the duct 18a of the deodorizing device, and a large amount of methane is detected by the methane gas sensor, for example, a large amount of defecation gas is released. Thus, the data analyzer 60 refers to a methane gas correction table, and corrects reliability on the basis of a detection amount of methane gas detected by the methane gas sensor. FIG. 29 is a diagram showing the methane gas correction table. As shown in FIG. 29, in the methane gas correction table, a correction amount is set at 1 when a detection amount of methane gas is smaller than a predetermined value, and when the detection amount of methane gas is the predetermined value or more, the correction value is made larger as the detection amount of methane gas increases. The methane gas correction value is for partial correction, because the methane gas correction value can be calculated for each of excretory acts.

In the present embodiment, when the detection values of $CO_2$ and methane are large, reliability is corrected to be high, but the present invention is not limited to this, and it is also possible to make correction that makes a detection value of hydrogen gas large when the detection values of $CO_2$ and methane are large.

Figure 30:
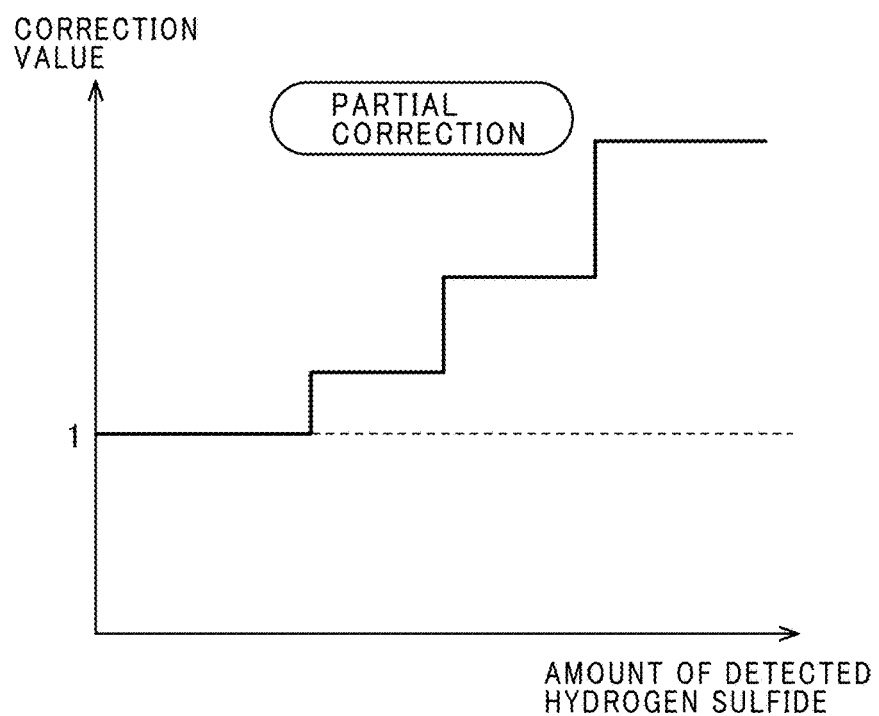
FIG. 30 is a diagram showing a sulfide gas correction table.

When there is cancer in intestine, not only stink gas but also hydrogen sulfide gas is contained in defecation gas. Consequently, a hydrogen sulfide gas sensor that reacts strongly to hydrogen sulfide gas is installed in the duct 18a of the deodorizing device, for example, and reliability is corrected on the basis of detection data of hydrogen sulfide gas detected by the hydrogen sulfide gas sensor. FIG. 30 is a diagram showing a hydrogen sulfide gas correction table. As shown in FIG. 30, in the hydrogen sulfide gas correction table, a correction value is set at 1 when a detection amount of sulfide gas is smaller than a predetermined value, and when the detection amount of hydrogen sulfide gas is a predetermined value or more, the correction value is made larger as the detection amount of hydrogen sulfide gas increases. The hydrogen sulfide gas correction value is for partial correction because the hydrogen sulfide gas correction value can be calculated for each of excretory acts. Reliability is calculated by using some or all of the correction tables described above.

Next, since detailed explanation concerning the method for estimating an amount of gas is omitted in the example described with reference to FIG. 9, the detailed explanation of the method of estimating an amount of gas is described here.

As the odiferous gas sensor 26 measuring odiferous gas, a semiconductor gas sensor or a solid electrolyte sensor is used. Gas sensors such as a semiconductor gas sensor, a solid electrolyte sensor, and a hydrogen gas sensor react to not only odiferous gas but also alcohol contained in an aromatic and a disinfecting sheet.

That is, even when a test subject is absent, detection data of a gas sensor includes environmental noise by an influence of an aromatic, and a residual stool attached to the bowl of a toilet, for example. The influence of an aromatic, and a residual stool attached to the bowl of the toilet like this does not vary so much with time.

Further, when a test subject enters a toilet space, a detection value detected by a gas sensor slowly increases by influence of stink gas components attached to a body and clothes of the test subject, such as a body odor of the test subject, perfume and hair liquid used by the test subject, but when the test subject sits on the seat, an upper side of the bowl is covered with the test subject and clothes, so that a data value detected by the gas sensor becomes stable, or slowly increases.

Further, if the test subject cleans the toilet seat by a disinfecting sheet, an amount of gas measured by the semiconductor gas sensor steeply increases the moment the disinfecting sheet is used, but after the test subject sits on the seat, that is, after a while after using the disinfecting sheet, the detection value measured by the gas sensor does not increase by the influence of the disinfecting sheet.

That is, after the test subject sits on the seat, the detection value of the gas sensor may slowly increase by an influence of stink gas attached to the body of the test subject, but the detection value does not steeply increase.

On the contrary, when the test subject starts an excretory act, the gas sensor reacts to stink gas and hydrogen gas contained in defecation gas at a point of time at which the test subject performs each defecation act, and a detection value of the gas sensor steeply increases, and reduces after reaching a peak.

Consequently, the present inventors have considered that after a test subject sits on the seat, a detection value by the gas sensor does not steeply increases, and if the detection value is used as a reference value, odiferous gas and hydrogen gas contained in defecation gas can be detected as a steep increase from the reference value.

Thus, in the present embodiment, as described with reference to FIG. 9, the data analyzer 60 sets detection data of the gas sensor in a non-excretory act period after time $t_2$ when the seating detection sensor 36 detects that the test subject sits on the seat 4 and before time is when the test subject starts an excretory act, as the reference value. Next, the data analyzer 60 sets a point of time when a rate of change of a difference between the detection value of the gas sensor and the reference value reaches a predetermined positive value or more at time $t_5$, as a disclosure time point. Subsequently, the data analyzer 60 time-integrates difference between the detection value of the gas sensor at the time of an excretory act and the reference value, in a period from a starting time point to an end time point of the excretory act (that is, obtains an area of a larger part of an amount of gas at the time of the excretory act than the reference value), and estimates this as an amount of defecation gas. The end time point of an excretory act may be a time point at which the detection value of the gas sensor returns to the reference value again, or may be a time point at which a rate of change of the difference between the detection value of the gas sensor and the reference value changes from a positive value to a negative value after the starting time point.

Similarly to the odiferous gas sensor 26, the hydrogen gas sensor 24 and the carbon dioxide sensor 28 may be influenced by noise of stink gas other than odiferous gas. Consequently, when amounts of hydrogen gas and carbon dioxide gas are estimated on the basis of detection data of the hydrogen gas sensor 24 and the carbon dioxide sensor 28, estimation of the amounts of hydrogen gas and carbon dioxide gas can be performed similarly to that of defecation gas.

The method for estimating the amount of gas is not limited to the above described method. Hereunder, a method for estimating an amount of gas in a biological information measurement system of the second embodiment will be described. In the second embodiment, only a method for estimating an amount of gas differs as compared with the first embodiment.

In the system of the present embodiment, a semiconductor gas sensor or a solid electrolyte sensor is also used as the odiferous gas sensor 26 that measures odiferous gas, as in the first embodiment. A semiconductor gas sensor or a solid electrolyte sensor measures an amount of gas by detecting heated catalyst reaction, and therefore is low in sensitivity. Further, the hydrogen gas sensor 24 is also low in sensitivity similarly to the semiconductor gas sensor. When a gas sensor low in sensitivity like this is used, a problem as follows arises. The following problem is not peculiar to a semiconductor gas sensor, but similarly occurs to a solid electrolyte sensor and a hydrogen gas sensor.

Figure 31:
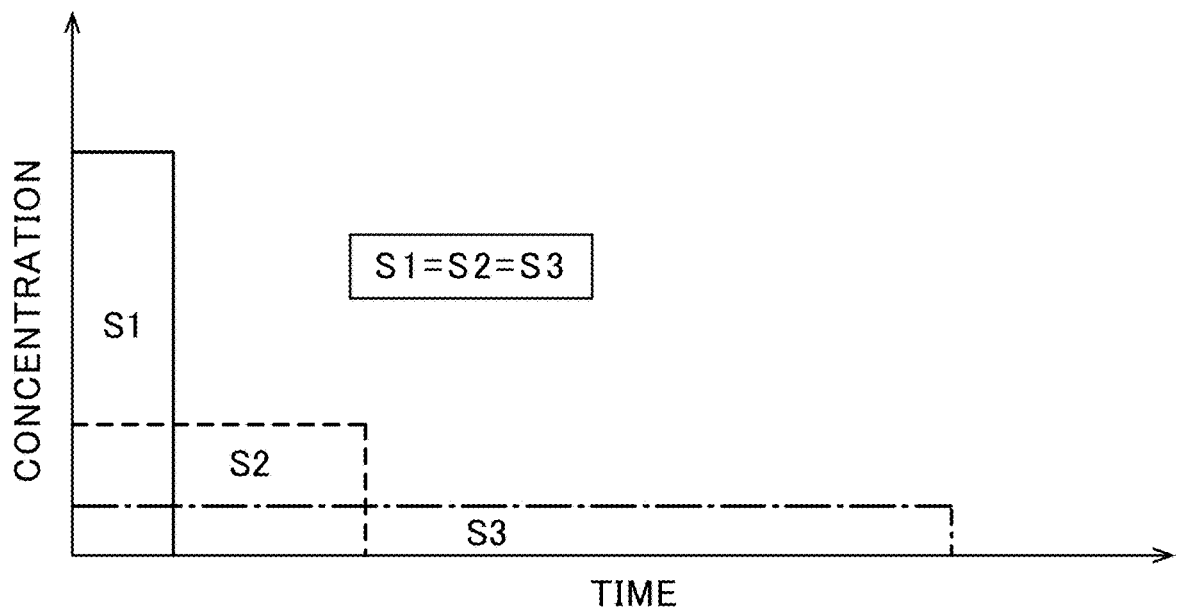
FIG. 31 is a diagram showing relationships of discharge times and discharge amounts of respective conditions S1, S2 and S3 in which the discharge times and the discharge amounts (discharge concentrations) per time differ from one another, though total amounts of discharge of defecation gas are fixed.
Figure 32:
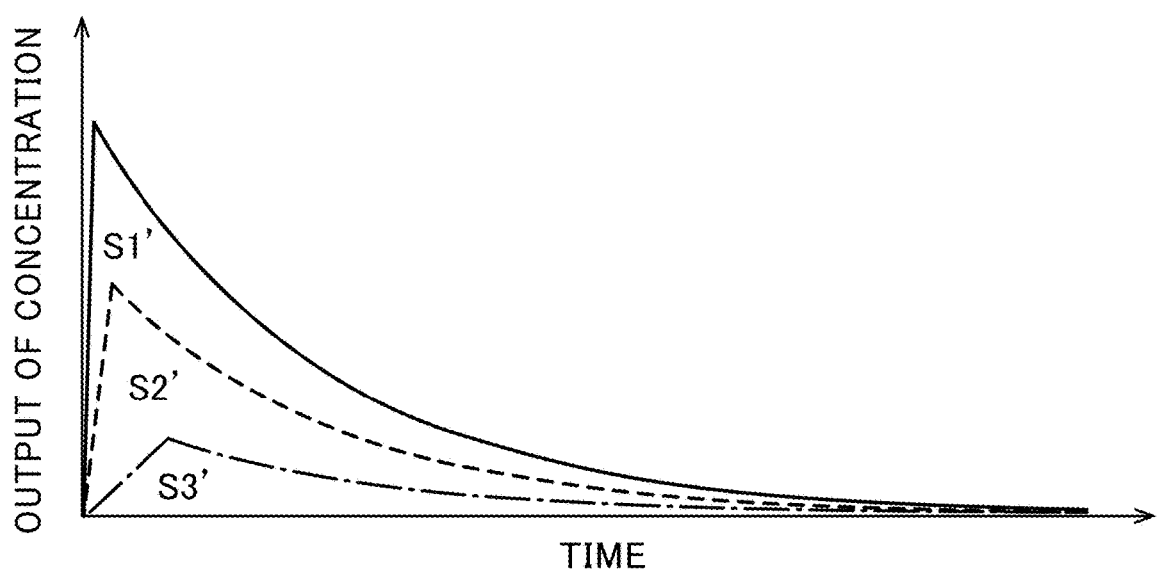
FIG. 32 is a diagram showing detection waveforms of a gas sensor in a case in which discharge times and discharge amounts per time are changed.
Figure 33:
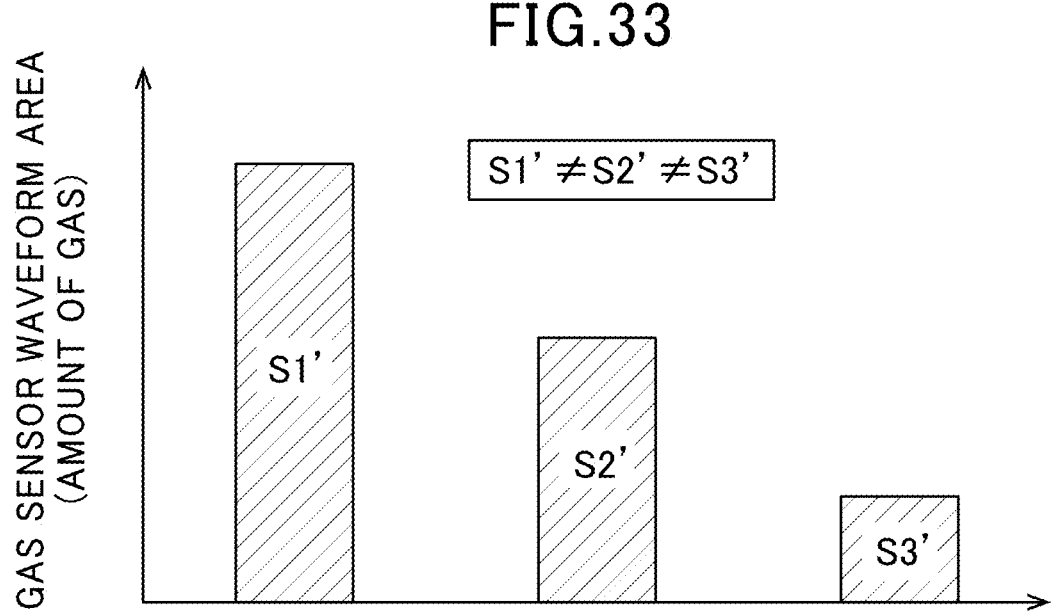
FIG. 33 shows amounts of gas calculated on the basis of the detection waveforms of the gas sensor.

As shown in FIG. 31, for example, a case in which defecation gas is detected by using a semiconductor gas sensor as the odiferous gas sensor 26 is considered, with respect to each of conditions S1, S2 and S3 which are fixed in total discharge amount of defecation gas, but differ in discharge time and discharge amount per time. FIG. 32 is a diagram showing detection waveforms of the gas sensor in a case in which a discharge time and a discharge amount per time are changed. FIG. 33 shows amounts of gas calculated on the basis of the detection waveforms of the gas sensor. In FIG. 32 and FIG. 33, S1', S2' and S3' correspond to S1, S2 and S3 in FIG. 31 respectively.

Figure 34:
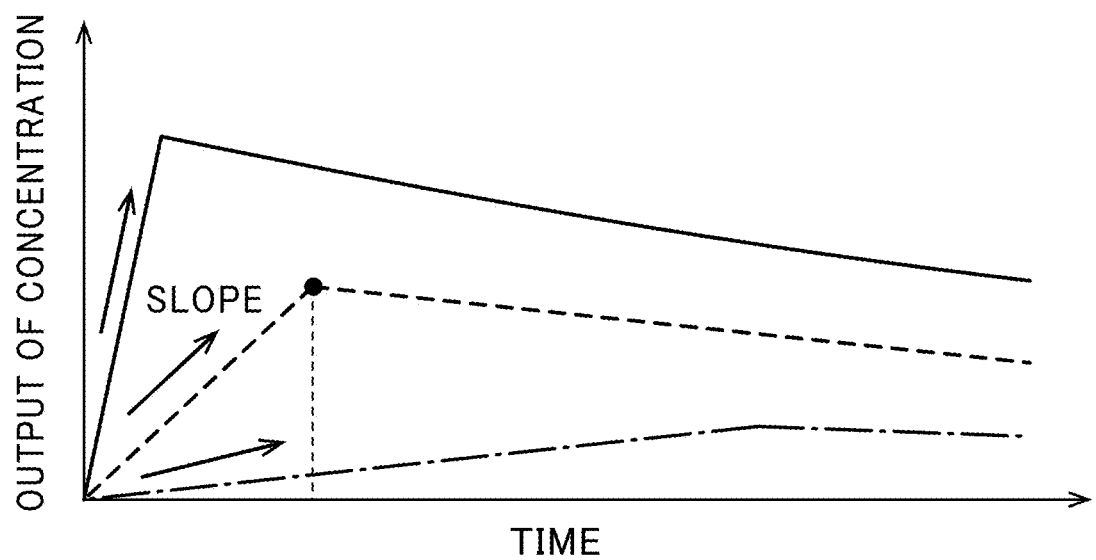
FIG. 34 is a diagram showing initial parts of the detection waveforms of the gas sensor shown in FIG. 32 by enlarging a time axis.
Figure 35:
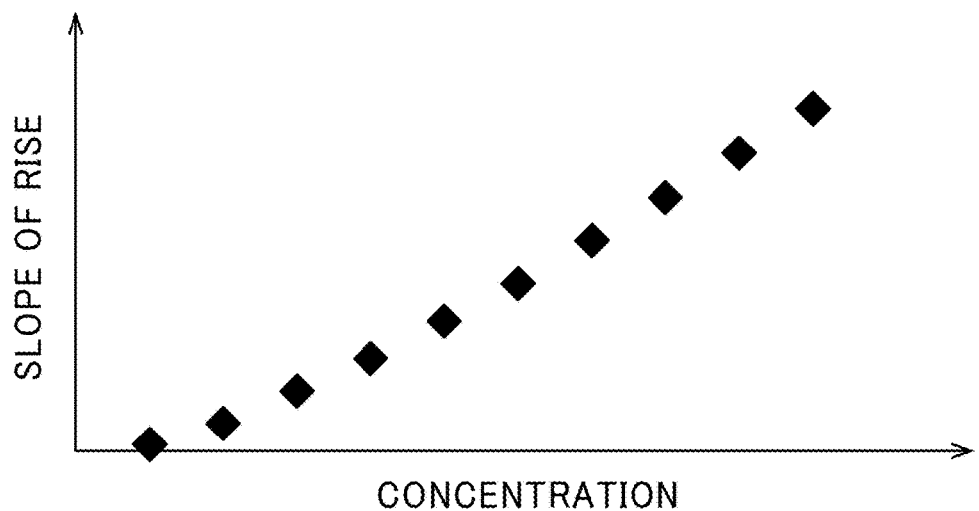
FIG. 35 is a graph showing a relationship between a discharge amount (discharge densities) per time and a gradient of a start of a detection data waveform detected by the sensor.

As shown in FIG. 32, even when the total discharge amount of defecation gas is fixed, if discharge times differ, gas discharge waveforms do not converge unless subsequently the same times are taken, due to a time constant of the gas sensor. Consequently, the present inventors pay attention to gradients at the time of discharging gas. FIG. 34 is a diagram showing initial parts of the detection waveforms of the gas sensor shown in FIG. 32 by enlarging a time axis. As shown in FIG. 34, when the amounts of discharge (discharge concentrations) per time differ, gradients from start of discharge to peak values and times until arriving at the peak values differ. Subsequently, as the amount of discharge (discharge concentration) per time is larger, the gradient to the peak value becomes larger, and as the gas discharge time is longer, the time until arriving at the peak value becomes longer. Further, FIG. 35 is a graph showing a relationship between the amount of discharge (discharge concentration) per time, and the gradient of start of the detection data waveform detected by the sensor. As shown in FIG. 35, the amount of discharge (discharge concentration) per time and the gradient of start of the waveform detected by the semiconductor gas sensor can be said as in a subsequently proportional relationship.

Figure 36:
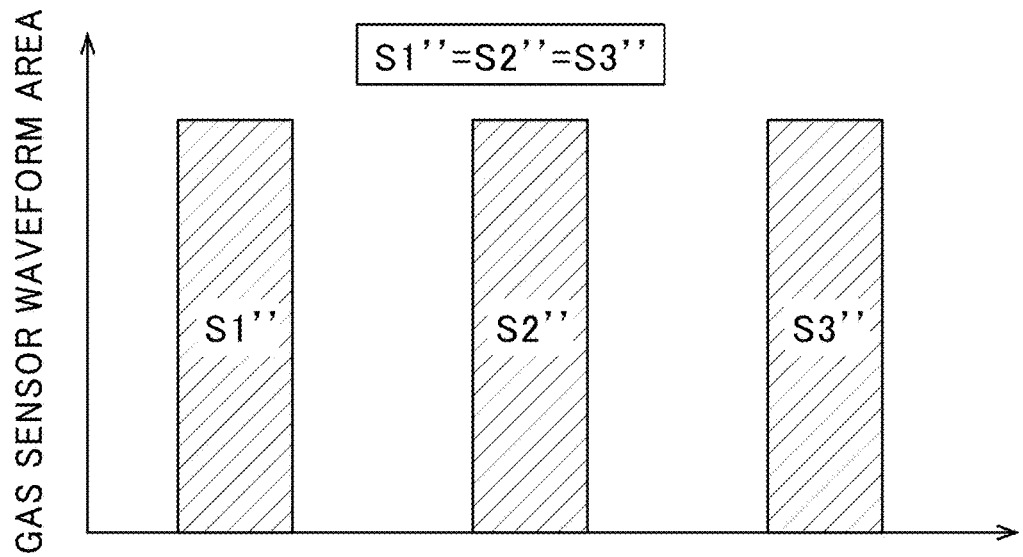
FIG. 36 is a diagram showing gas amounts estimated on the basis of products (gas sensor waveform areas) of gradients of the detection waveforms of a semiconductor gas sensor and arrival times at peaks, for the respective conditions S1, S2 and S3 in which the discharge times and the discharge amounts (discharge concentrations) per time differ from one another.

The inventors estimate the amount of gas on the basis of a product (an area of a gas sensor waveform) of the gradient of the detection waveform of the semiconductor gas sensor and the time until arriving at the peak, based on the knowledge that the gradient of the detection waveform by the semiconductor gas sensor described above corresponds to a discharge amount of discharge gas (discharge concentration) per time, and the time until arriving at the peak of the detection waveform by the semiconductor gas sensor corresponds to a discharge time. FIG. 36 shows amounts of gas that are estimated on the basis of the products (the areas of the gas sensor waveforms) of the gradients of the detection waveforms of the semiconductor gas sensor and the times until arriving at the peaks, with respect to the respective conditions S1, S2 and S3 in which the discharge times and the amounts of discharge (the discharge concentrations) per time differs like this. As shown in FIG. 36, gas amounts S1", S2" and S3" which are estimated on the basis of the products of the gradients of the waveforms of the amount of gas and the times until arriving at the peaks are the same amounts, and it is understandable that accurate estimation of the amounts of gas can be performed on the basis of the gradients of the waveforms of the amounts of gas and the times until arriving at the peaks.

Thus, in the present embodiment, a reference value is set on the basis of the detection data by the odiferous gas sensor 26 after a time point at which the seating detection sensor 36 detects that a test subject sits on the seat, and before an excretory act is started, as in the first embodiment described above. Subsequently, as shown in FIG. 10A, a time point at which the rate of change of the difference between the detection value measured by the odiferous gas sensor 26 and the reference value exceeds a start threshold value that is set in advance, is set as a start time point of estimation of the amount of defecation gas (that is, a start time point of an excretory act). Next, as shown in FIG. 10A, a time point at which the rate of change of the difference between the detection data detected by the odiferous gas sensor 26 and the reference value becomes negative (that is, a time point of a peak of the detection data of the odiferous gas sensor 26) is set as an end time point of estimation of the amount of defection gas (that is, an end time point of an excretory act).

Next, the data analyzer 60 calculates a rate of change of the difference between detection data in a period from a start time point to an end time point of an excretory act, and the reference value. Further, the data analyzer 60 calculates a defecation gas discharge time from the start time point to the end time point of the excretory act. Subsequently, the data analyzer 60 integrates the rate of change of the difference between the detection data in the period from the start time point to the end time point of the excretory act and the reference value with the defecation gas discharge time, and the integration value is estimated as the amount of gas. Estimation of the amount of hydrogen gas based on the detection data of the hydrogen gas sensor 24, and estimation of the amount of carbon dioxide gas based on the detection data of the carbon dioxide sensor 28 can be performed similarly. According to the method for estimating the amount of gas described above, an influence of the time constant of the gas sensor is excluded, and the amount of defecation gas can be estimated more accurately.

Further, the inventors have studied on the relationship between the discharge amount per time of defecation gas, and the discharge time, and have found that individual differences are small in the relationship between the discharge amount and the discharge time. That is, when the amount of discharge per time of defecation gas is large, the discharge time is a fixed time that is relatively short irrespective of a test subject, whereas when the amount of discharge per time of discharge gas of defecation gas is small, the discharge time is a long fixed time irrespective of a test subject. Consequently, the inventors have considered that the discharge time of defecation gas (odiferous gas) can be estimated on the basis of the discharge amount per time of the odiferous gas in defecation gas (a rate of change of the detection value detected by the odiferous gas sensor 26). Similarly to this, the discharge time of defecation gas (hydrogen gas and carbon dioxide) can be estimated on the basis of discharge amounts per time of hydrogen gas and carbon dioxide (rates of change of the detection values detected by the hydrogen gas sensor 24 and the carbon dioxide sensor 28). Although in the present embodiment, an area is estimated so as to obtain a correlation between the amount of healthy-state gas and the amount of odiferous gas, a configuration to obtain a concentration from a gradient of the measurement value of each of the sensors may be adopted because a concentration of healthy-state gas and a concentration of odiferous gas are similarly correlated and a similar result is obtained. In this case, measurement can be performed more simply because the area is not estimated.

Hereunder, a method for estimating an amount of gas in a biological information measurement system of a third embodiment based on the above described knowledge is described. The third embodiment is different in only a method for estimating an amount of gas, as compared with the first and second embodiments. In the data analyzer 60, rate of change-discharge period data concerning a correspondence relation of a rate of change of a difference and a discharge time of gas is set, in addition to a start threshold value of the rate of change of the difference described in the above described embodiment.

A reference value is set on the basis of detection data of the odiferous gas sensor 26 in a period after a time point at which the seating detection sensor 36 detects a test subject sits on the seat, and before an excretory act is started. A point of time at which the rate of change of the difference between the detection value measured by the odiferous gas sensor 26 and the reference value exceeds the start threshold value set in advance is set as a start time point of estimation of an amount of defecation gas (that is, a start time point of an excretory act). Subsequently, the data analyzer 60 refers to the rate of change-discharge period data, and acquires discharge period data corresponding to the rate of change of the difference between the detection value at the start time point and the reference value. Subsequently, the data analyzer 60 integrates the rate of change of the difference between the detection data at the start time point of an excretory act and the reference value with the discharge time, and estimates the integration value as the amount of gas. Estimation of an amount of hydrogen gas based on detection data of the hydrogen gas sensor 24, and estimation of an amount of carbon dioxide gas based on detection data of the carbon dioxide sensor 28 also can be performed similarly. According to the method for estimating the amount of gas described above, an influence of the time constant of the gas sensor is excluded, and the amount of defecation gas can be estimated more accurately. Although in the method for estimating the amount of gas in each of the above described embodiments, the case of using a semiconductor gas sensor as the odiferous gas sensor 26 is described, estimation of the amount of gas can be also performed even in a case of using a solid electrolyte sensor instead of the semiconductor gas sensor. In the above described embodiment, the data analyzer 60 obtains the rate of change of a difference, acquires discharge period data corresponding to the rate of change of the difference between the detection value at the start time point and the reference value by referring to the rate of change-discharge period data, and estimates the amount of gas on the basis of the rate of change and the discharge period, but the present invention is not limited to this. For example, rate of change-gas amount data in which the rate of change of a difference and the amount of gas are associated with each other is stored in advance, the change of rate of the difference is obtained, and the amount of gas may be directly estimated by referring to the rate of change-gas amount data.

Although in the biological information measurement system of the first embodiment described with reference to FIG. 1, it is described that the measuring device 6 is assembled inside the seat 4 mounted on the flush toilet 2 installed in the toilet installation room R, the measuring device is not required to be always assembled inside the seat in the biological information measurement system of the present invention.

Figure 37A:
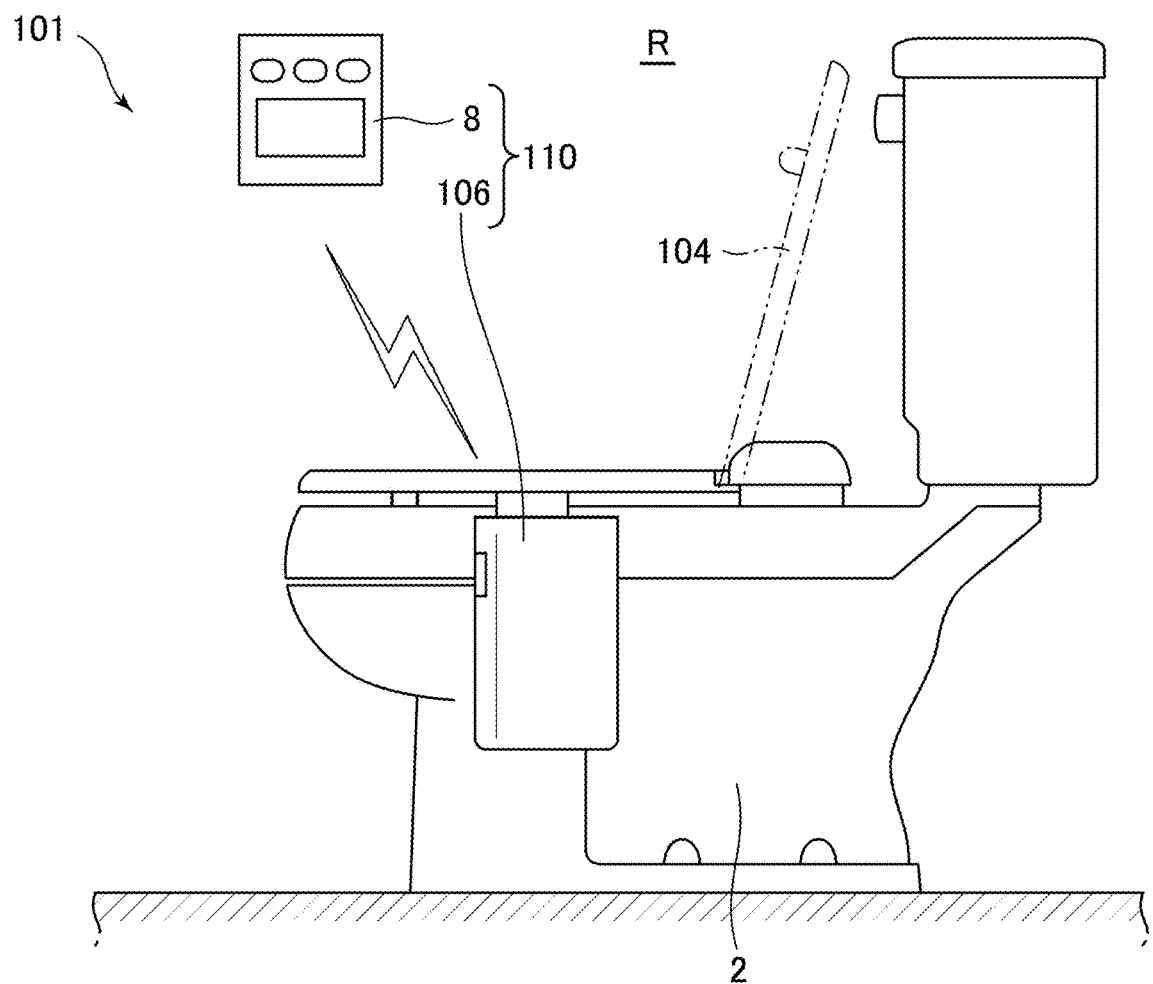
FIG. 37A is a view showing a state in which a test subject-side device of a biological information measurement system according to another embodiment is attached to a flush toilet installed in a toilet installation room.
Figure 37B:
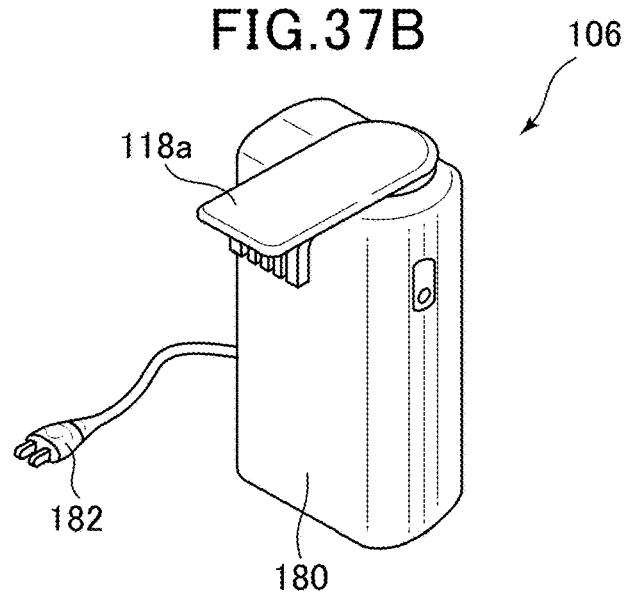
FIG. 37B is a perspective view showing a measuring device of the test subject-side device shown in FIG. 37A.

FIG. 37A shows a state in which a test subject-side device of a biological information measurement system in accordance with a fourth embodiment is attached to a flush toilet installed in a toilet installation room, and FIG. 37B is a perspective view showing a measuring device of the test subject-side device shown in FIG. 37A. The fourth embodiment is only different in a configuration of the test subject-side device as compared with the first embodiment. As shown in FIG. 37A, a biological information measurement system 101 of the present embodiment has the same configuration as that of the first embodiment, except that only a measuring device 106 of a test subject-side device 110 is different. The measuring device 106 of the present embodiment is provided separately from a seat 104.

As shown in FIG. 37B, the measuring device 106 includes a device body 180, a duct 118a that is attached on a top face of the device body 180 so as to extend in a traverse direction, and that is provided with an edge portion bent downward, and a power source code 182 that is connected to the device body 180. As shown in FIG. 37A, the measuring device 106 is fixed while an end of the duct 118a is positioned in the bowl by hanging the edge portion of the duct 118a on a sidewall of a bowl of the flush toilet 2.

The device body 180, as with the first embodiment, includes a hydrogen gas sensor, an odiferous gas sensor, a carbon dioxide sensor, a humidity sensor, a temperature sensor, an entrance detection sensor, a seating detection sensor, a defecation/urination detection sensor, a suction device, a sensor heater, and a transmitter-receiver. Gas sucked through the duct 118a is deodorized and is discharged through a deodorized air outlet provided in a bottom face of the device body 180. In the duct 118a, there are provided the hydrogen gas sensor, the odiferous gas sensor, the carbon dioxide sensor, the humidity sensor, the temperature sensor, the sensor heater, and a fan. Arrangement of the sensors in the duct 118a is the same as that of the first embodiment, so that description thereof is omitted. According to this kind of configuration, the measuring device 106 of the present embodiment is also capable of acquiring detection data corresponding to the amount of odiferous gas, hydrogen gas, and carbon dioxide, contained in defecation gas, by using the odiferous gas sensor, the hydrogen gas sensor, and the carbon dioxide sensor.

It is desirable that the seat 104 to be used along with the measuring device 106 of the present embodiment is a seat with a cleaning function that includes a toilet lid opening/closing device, a nozzle driving device, a nozzle cleaning device, a toilet cleaning device, and a toilet disinfection device, the seat being capable of communicating with the measuring device 106. Using the measuring device 106 along with this kind of seat enables various cleaning operations and disinfecting operation to be performed when stink gas is detected.

Figure 38:
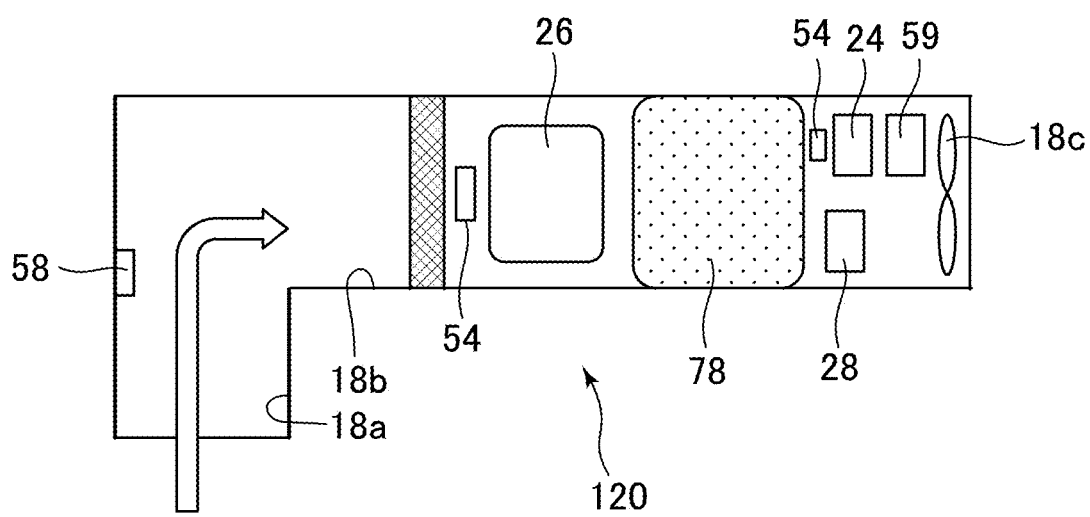
FIG. 38 is a view showing a configuration of a suction device of another embodiment of the present invention.

Although in the first embodiment, the gas detector 20 is configured so that the hydrogen gas sensor 24 is provided downstream of the deodorant filter 78, as shown in FIG. 3, this kind of configuration is not always required. FIG. 38 shows a configuration of a gas detector provided in a biological information measurement system of a fifth embodiment. The fifth embodiment is only different in a configuration of the gas detector as compared with the first embodiment. As shown in FIG. 38, arrangement of the hydrogen gas sensor 24 in the gas detector 120 in the present embodiment is different from that in the embodiment shown in FIG. 3. In the present embodiment, the hydrogen gas sensor 24 is provided downstream of the deodorant filter 78 in the air intake passage 18b. According to this kind of configuration, even if a sensor sensitive to odiferous gas as well as to hydrogen gas is used as the hydrogen gas sensor 24, it is possible to remove influence of odiferous gas from data to be outputted from the hydrogen gas sensor 24.

In the first embodiment, although a detection value of odiferous gas is calculated by subtracting a detection value acquired by the hydrogen gas sensor 24 from a detection value acquired by the odiferous gas sensor 26 to separate influence of hydrogen gas, the present invention is not limited to the way above. For example, as described below, influence of hydrogen gas can be also separated by varying a reaching time of each of hydrogen gas and odiferous gas to the odiferous gas sensor 26.

Figure 39:
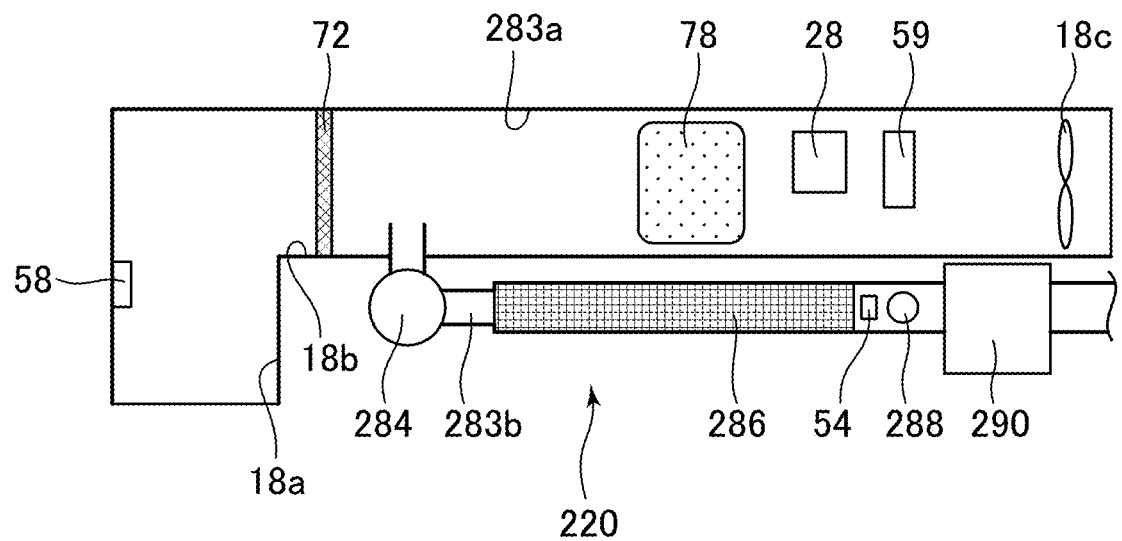
FIG. 39 is a view showing a configuration of a gas detector according to another embodiment of the present invention, the gas detector being configured to vary an arrival time of each of hydrogen gas and odiferous gas at the odiferous gas sensor to separate influence of the hydrogen gas.

FIG. 39 shows a configuration of a gas detector of a sixth embodiment, the gas detector being configured to vary a reaching time of each of hydrogen gas and odiferous gas to the odiferous gas sensor to separate influence of the hydrogen gas. The sixth embodiment is only different in the configuration of a gas detector as compared with the first embodiment. As shown in FIG. 39, in the present embodiment, there is provided a branch passage 283b that branches from a main passage 283a of the air intake passage 18b in the duct 18a. While a hydrogen gas sensor and an odiferous gas sensor are separately provided in the first embodiment, the present embodiment is configured to detect both hydrogen gas and odiferous gas by using one semiconductor gas sensor.

As with the first embodiment, the air intake passage 18b includes the filter 72, the deodorant filter 78 provided downstream of the filter 72, and the suction fan 18c, and the branch passage 283b branches on the downstream side of the filter 72. The filter 72 does not have a deodorizing function, and allows odiferous gas and hydrogen to pass therethrough, but prevents foreign material, such as urine, and a cleaner from passing therethrough. As with the first embodiment, the deodorant filter 78 is also a catalyst that adsorbs gas components of odiferous gas or the like.

Defecation gas in the bowl 2a of the toilet is sucked into the air intake passage 18b at a fixed flow rate by the suction fan 18c. The defecation gas sucked into the air intake passage 18b passes through the filter 72 so that foreign material, such as urine, and a cleaner, is removed, and then is returned into the bowl 2a of the toilet after gas components of odiferous gas or the like are removed by the deodorant filter 78.

The branch passage 283b includes a flow channel changeover valve 284, a column 286, a semiconductor gas sensor 288, and a pump 290, in order from an upstream side toward a downstream side.

The flow channel changeover valve 284 is opened in a partial time (a very short time) during an excretory act to allow a part of defecation gas flowing through the air intake passage 18b (for the partial time during the excretory act of a test subject) to be drawn into the branch passage 283b. The flow channel changeover valve 284 is provided at the most upstream portion of the branch passage 283b.

The column 286 is provided downstream of the flow channel changeover valve 284, and is formed by filling elongated piping with thin fibers and the like, for example. The column 286 has a mechanism in which passing time of gas varies in accordance with molecule size (molecular weight), according to a principle of gas chromatography.

The sensor heater 54 is provided upstream of the semiconductor gas sensor 288 to heat a catalyst of the semiconductor gas sensor 288 to a predetermined temperature as well as remove stink gas components attached to the semiconductor gas sensor 288.

The flow channel changeover valve 284 allows defecation gas in trace amounts flowing through the air intake passage 18b after passing through the filter 72 to flow into the branch passage 283b. Then, when the pump 290 is driven, each of hydrogen and odiferous gas, contained in the defecation gas, passes through the column 286 for a different time in accordance with molecular weight, according to the principle of gas chromatography, to reach the semiconductor gas sensor 288. That is, hydrogen with a small molecular weight tends to easily pass through the column 286 to reach the semiconductor gas sensor 288 in a short time, and odiferous gas with a large molecular weight tends to be difficult to pass through the column 286 to reach the semiconductor gas sensor 288 in a longer time as compared with the hydrogen. The pump 290 is configured to suck defecation gas at a fixed flow velocity.

Figure 40:
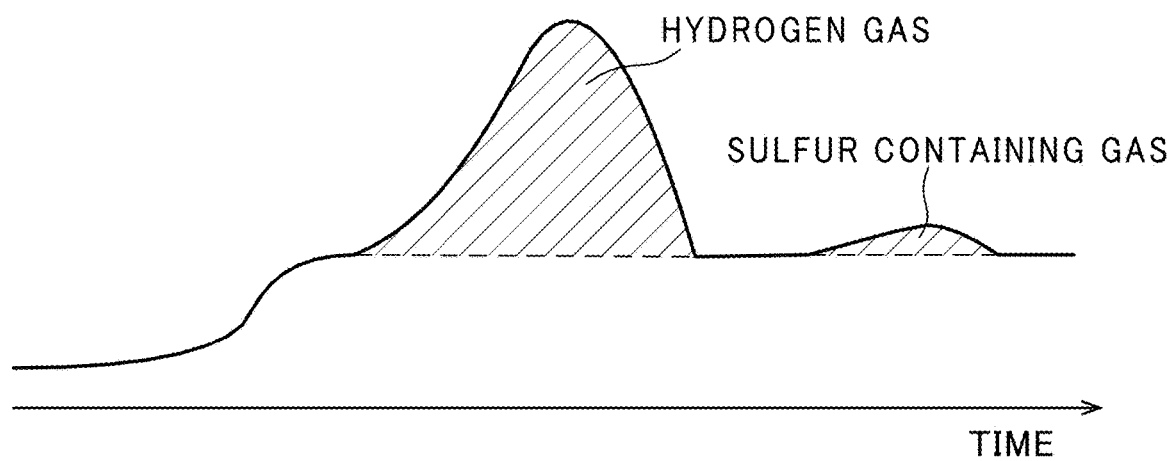
FIG. 40 is a diagram showing a detection waveform detected by a semiconductor gas sensor of the gas detector, shown in FIG. 39.

FIG. 40 shows a detection waveform acquired by a semiconductor gas sensor of a gas detector, shown in FIG. 39. As shown in FIG. 40, according to a configuration of a gas detector 220 of the present embodiment, the semiconductor gas sensor 288 reacts to hydrogen gas and odiferous gas, which are temporally separated. In particular, an excretory act is performed in a short time, and defecation gas containing hydrogen and odiferous gas is also discharged only in a short time. In this way defecation gas is discharged in a short time, and thus providing the column 286 upstream of the semiconductor gas sensor 288 enables a time by which each of hydrogen gas and odiferous gas reaches the semiconductor gas sensor to be varied, whereby it is possible to detect the amount of hydrogen gas, and the amount of odiferous gas, by using one semiconductor gas sensor 288. This is also based on technical findings made by the present inventors that if a method of determining physical condition using a correlation between healthy-state gas and odiferous gas without measuring all of the amount of methyl mercaptan gas in correlation with cancer is adopted, gas only in a specific period can be measured in this kind of method. If a reduction sensor is used, the sensor is inexpensive but it is difficult to separate a large amount of hydrogen contained in defecation gas. In contrast, since the present embodiment allows a small amount of gas to be measured only in a specific period, separation of hydrogen becomes easy so that practicality can be achieved with a very inexpensive sensor.

While the present embodiment allows the column 286 to vary a reaching time of each of hydrogen and odiferous gas to the semiconductor gas sensor 288, it is a matter of course that it is possible to vary a reaching time of methane contained in defecation gas. Accordingly, it is also possible to separate influence of not only hydrogen but also methane from detection data acquired by a semiconductor gas sensor.

As described above, according to each of the embodiments described above, defecation gas discharged into a bowl of the bowl 2a of the flush toilet 2 is measured to analyze physical condition of a test subject by the test subject-side device 10 and the server 12, so that it is possible to perform diagnosis by allowing a test subject to only perform defecation performed every day, as usual without requiring an effort to perform a measurement action. Requiring no effort allows the test subject to have no burden, so that it is possible to continue measurement for a long time to reliably acquire information on a change in health condition, and on a state where a risk of cancer is increasing.

Further, in each of the embodiments described above, in the gas detector 20, no sensor for measuring methyl mercaptan gas at a pinpoint is used, and a semiconductor gas sensor or a solid electrolyte sensor that is widely sensitive also to odiferous gas other than the methyl mercaptan gas, in defecation gas, is used as the odiferous gas sensor 26. If a risk of cancer increases, a very strong odiferous gas containing a sulfur component, such as methyl mercaptan gas or hydrogen sulfide, increases in amount. Thus, according to each of the embodiments described above, a sensor that is widely sensitive to odiferous gas, such as a semiconductor gas sensor and a solid electrolyte sensor is used, so that it is possible to detect an increased risk of cancer reliably.

Further, each of the embodiments described above analyzes physical condition on the basis of detection data acquired by the odiferous gas sensor 26 that detects not only methyl mercaptan gas, but also odiferous gases other than methyl mercaptan gas, such as hydrogen sulfide, acetic acid, trimethylamine, and ammonia, in defecation gas. Thus, an analysis result based on an amount of the odiferous gas mixed in the defecation gas reflects a result caused by a wrong physical condition and a bad living habit, of a test subject, so that the analysis result is usable as an index based on objective data for improving physical condition and a living habit in which this kind of risk of cancer may increase, or is usable as an effective index for maintaining a health condition to reduce a risk of having cancer.

In addition, each of the embodiments described above uses a semiconductor gas sensor and a solid electrolyte sensor that are widely sensitive not only to methyl mercaptan gas but also to odiferous gas other than the methyl mercaptan gas, so that a device can be manufactured at low cost, and thereby the device can be provided as a consumer product.

Further, a semiconductor gas sensor and a solid electrolyte sensor that are widely sensitive to not only methyl mercaptan gas but also to odiferous gas other than the methyl mercaptan gas have no practicality in precision of cancer diagnosis in diagnosis of each time, because a measurement value varies depending on physical condition and meals that change every day. On the contrary, according to each of the embodiments described above, defecation gas is measured in a usual daily act of defecation, so that even though measurement precision of each time is low, use of measurement data of a huge number of times accumulated and stored in the database enables precision of diagnosis that the risk of cancer is increasing, or having cancer to be ensured in a necessary and sufficient manner.

Further, according to each of the embodiments described above, physical condition is analyzed every day on the basis of not only methyl mercaptan gas but also odiferous gas other than the methyl mercaptan gas. Thus, the test subject can use the analysis result as an index based on an objective data value for improving a bad living habit, or an effective index for maintaining a health condition to reduce a risk of having cancer.

Further, analysis according to each of the embodiments described above requires long-term accumulation of measurement data, and further requires diagnostic analysis based on the measurement data. Assembling accumulation of the measurement data like this, and an analyzing system to the device 10 on a subject side installed in each household causes increase in cost and, prevents the test subject-side device 10 from being widely used as a consumer product. On the contrary, according to each of the embodiments described above, measurement data is transmitted to the server 12 to be managed in the database, and analysis of physical condition is performed on a server side, whereby the test subject-side device 10 purchased by a consumer can be provided at low price. Further, analysis of physical condition is performed in the server 12, so that precision of the analysis of physical condition can be dramatically increased.

Further, according to each of the embodiments described above, physical condition of a test subject is also analyzed in the test subject-side device 10 and can be outputted to the test subject, so that frequencies of analysis and notification in the server 12 are decreased to enable a burden to be reduced, and the test subject can improve a daily life quickly, reliably, and easily on the basis of display to the test subject-side device 10.

Further, in each of the embodiments described above, analysis by the test subject-side device 10 is simpler than analysis by the server 12. Consequently, a test subject can acquire information timely with high frequency by the test subject-side device 10 to perform management of physical condition, can decrease an analysis burden by reducing a frequency of analysis on a server side, and further can analyze a situation of a cancer risk accurately.

Further, in each of the embodiments described above, analysis in the test subject-side device 10 and the server 12 is performed on the basis of detection data of odiferous gas containing a sulfur component and healthy-state gas. Thereby, it becomes possible to ensure sufficient reliability by only adding the low-priced hydrogen gas sensor 24 to the simple odiferous gas sensor 26 without using an expensive sensor, and to increase precision of analysis of physical condition dramatically.

Further, in each of the embodiments described above, an analysis result displayed in the medical facility terminal 16 includes a determination result concerning a specific disease, but an analysis result displayed in the test subject-side device 10 includes no determination results concerning the specific disease, though the analysis result includes a history of the measurement data. Consequently, the analysis result by the test subject-side device 10 includes no determination result concerning cancer, so that no mental burden is applied to a test subject. In addition, the analysis result displayed in the test subject-side device 10 includes the history of the measurement data, so that a test subject can grasp a change in physical condition by checking a change in data, and can be reliably encouraged to make an effort to improve physical condition.

Further, in each of the embodiments described above, the test subject-side device 10 analyzes physical condition of a test subject on the basis of data in a partial period during an excretory act, of the measurement data, and the server 12 analyzes physical condition of a test subject on the basis of a period longer than the partial period during an excretory act, of the measurement data, that is, data in an entire period. Thereby, the test subject-side device 10 enables a test subject to receive a result immediately during an excretory act or immediately after an excretory act.

Further, in each of the embodiments described above, the database stores the measurement data in the entire period of a defecation act, and the server 12 analyzes physical condition of a test subject on the basis of the measurement data in the entire period of the defecation act. This enables accurate analysis of a disease of cancer having a correlation with a generation amount of methyl mercaptan gas.

Further, in each of the embodiments described above, the test subject-side device 10 includes the reliability determination circuit, and analyzes physical condition of a test subject on the basis of measurement data in a period in which reliability is high, of the measurement data. This enables analysis of physical condition to be performed on the basis of measurement data with less influence of stink gas components such as sweat and urine attached to a test subject, an alcoholic disinfectant and the like, and enables analysis of physical condition to be accurate and stable.

Further, in each of the embodiments described above, the test subject-side device 10 performs analysis on the basis of data in the defecation gas detection period of the initial time, of the measurement data. This enables analysis to start reliably in a defecation act period, so that the analysis result can be reliably provided during a defecation act or immediately after the defecation act. Further, when a test subject has an idea that the test subject has performed a bad living habit, the test subject may be less willing to brows the analysis result, but since the analysis result is provided during a defecation act or immediately after the defecation act, the test subject certainly brows the analysis result, and even a test subject less willing to brows the analysis result can be encouraged to improve physical condition.

Further, in each of the embodiments described above, the database in the server 12 stores reliability as well as the measurement data, and reliability as well as an analysis result is outputted to the medical facility terminal 16. Thereby, it can be accurately determined whether a state of a bad analysis result is due to wrong physical condition, or due to noise caused by an unsanitary environment and the like, and an unnecessary mental burden can be reliably prevented from being given.

Further, in each of the embodiments described above, the device 10 on a subject side accepts input of defecation history information concerning a defecation history situation of a test subject by the input device 64, the defecation history information is stored in the database of the server 12 with measurement data, and the defecation history information is outputted to the medical facility terminal 16, with an analysis result. Thereby, even when dates and times of the measurement data stored in the database are apart from one another, it can be determined whether obstipation has occurred, so that more accurate diagnosis can be performed.

Further, in each of the embodiments described above, the test subject-side device 10 further determines an amount and a state of stool defecated by a test subject, information on the amount and state of stool is stored in the database of the server 12 with the measurement data, and the information on the amount and state of stool is outputted to the medical facility terminal 16 with the analysis result. This enables a doctor and the like to perform diagnosis after taking the amount and state of stool displayed in the medical facility terminal 16 into consideration, so that a doctor and the like can perform accurate diagnosis.

Further, in each of the embodiments described above, the device 10 on a test subject may not transmit measurement data to the server when reliability of the measurement data is low. The configuration like this can omit transmission of the data with low reliability to the server 12, so that transmission and reception of useless data and a load on the server 12 can be reduced.

Further, in each of the embodiments described above, the test subject-side device 10 can analyze physical condition of a test subject on the basis of the measurement data stored in the database of the server 12. The configuration like this makes it unnecessary to provide a storage device for storing measurement data, in the test subject-side device 10, and the test subject-side device 10 can be provided at a lower price.

Further, in each of the embodiments described above, the server 12 configures a new physical condition display table to be a reference of analysis by the test subject-side device 10 on the basis of measurement data accumulated and recorded in the database, and the physical condition display table of the device 10 on a subject side is updated to a new physical condition display table configured by the server 12. This enables analysis in the device 10 on a test subject to be easily updated to the physical condition display table in which an influence of individual differences is reduced, so that a test subject is enabled to perform health management with confidence.

What is claimed is:

1. A biological information measurement system that diagnoses a risk of illness of a test subject based defecation gas discharged into a bowl of flush toilet, the biological information measurement system comprising a test subject-side device provided in a room where the flush toilet is installed, and a server communicable with the test subject-side device,
    wherein the test subject-side device comprises:
    a suction device that sucks gas in the bowl into which the defecation gas is discharged during a defecation act of the test subject;
    a gas detector that is sensitive to a methyl mercaptan gas including an odiferous gas containing a sulfur component and an odiferous gas other than the methyl mercaptan gas, wherein the gas sucked by the suction device comprises the methyl mercaptan gas and the odiferous gas other than the methyl mercaptan gas, and wherein the gas detector outputs a first detection data;
    a test subject identification device that accepts an input of a test subject identification information;
    a control device that controls the suction device and the gas detector; and
    a communication device that transmits a measurement data including the first detection data to the server, and
    the server comprises:
    a database wherein the measurement data is accumulated and recorded with a date and time of the defecation act by being associated with the test subject identification information accepted by the test subject identification device;
    a server-side analyzer that analyzes the risk of illness of the test subject on the basis of a time-dependent variation tendency of the measurement data accumulated and recorded in the database; and
    a server-side output device that outputs an analysis result by the server-side data analyzer.

2. The biological information measurement system according to claim 1, wherein the test subject-side device further comprises:
    a test subject-side data analyzer that analyzes the risk of illness of the test subject on the basis of the time-dependent variation tendency of the measurement data; and
    a test subject-side output device that outputs an analysis result of the risk of illness by the test subject-side data analyzer.

3. The biological information measurement system according to claim 2,
    wherein the gas detector is further sensitive to healthy-state gas composed of at least one of hydrogen gas, carbon dioxide, and methane gas contained in gas sucked by the suction device, and outputs second detection data,
    the measurement data includes the second detection data of the healthy-state gas, and
    analysis by the test subject-side data analyzer is simpler than analysis by the server-side data analyzer.

4. The biological information measurement system according to claim 3,
    wherein the analysis result outputted by the server-side output device includes a determination result concerning a disease, and
    the analysis result outputted by the test subject-side output device includes a history of the measurement data, and does not include a determination result concerning the disease.

5. The biological information measurement system according to claim 4,
    wherein the test subject-side data analyzer further comprises a reliability determination circuit that determines a reliability of the first detection data outputted by the gas detector,
    the reliability as well as the measurement data is recorded in the database, and
    the reliability as well as the analysis result is outputted to the server-side output device.

6. The biological information measurement system according to claim 4,
    wherein the test subject-side device further comprises an input device,
    the input device accepts input of a defecation history information concerning a defecation history situation of the test subject,
    the defecation history information is recorded in the database, with the measurement data, and
    the defecation history information as well as the analysis result is outputted to the server-side output device.

7. The biological information measurement system according to claim 4,
    wherein the test subject-side device further includes a stool state determination sensor that determines at least one of an amount of a stool defecated by a test subject, and a state of the stool,
    the database records stool state information including at least one of the amount of a stool and the state of the stools, with the measurement data, and
    the stool state information as well as the analysis result is outputted to the server-side output device.

8. The biological information measurement system according to claim 4, wherein the test subject-side data analyzer further comprises a reliability determination circuit that determines a reliability of the first detection data outputted by the gas detector, and the test subject-side device does not transmit the measurement data to the server, when reliability determined by the reliability determination circuit is low.

9. The biological information measurement system according to claim 4, wherein the test subject-side data analyzer analyzes the risk of illness of the test subject on the basis of the measurement data recorded in the database of the server.

10. The biological information measurement system according to claim 4, wherein the server configures new reference data to be a reference of analysis by the test subject-side data analyzer, on the basis of the measurement data accumulated and recorded in the database, and a reference data of the test subject-side data analyzer is updated to the new reference data configured by the server.

11. The biological information measurement system according to claim 4, wherein the test subject-side data analyzer analyzes the risk of illness of the test subject-side data analyzer analyzes the risk of illness of the test subject on the basis of a partial data of the measurement data during the defecation act, and the server-side data analyzer analyzes the risk of illness of the test subject on the basis of a data in a longer period than the partial data of the measurement data during the defecation act.

12. The biological information measurement system according to claim 11, wherein the measurement data comprising an entire period of the defecation act is recorded in the database, and the server-side data analyzer analyzes the risk of illness of the test subject on the basis of the measurement data.

13. The biological information measurement system according to claim 11, wherein the test subject-side data analyzer further comprises a reliability determination circuit that determines a reliability of the first detection data outputted by the gas detector, and the test subject-side data analyzer analyzes the risk of illness of the test subject on the basis of the measurement data in a period in which the reliability determined by the reliability determination circuit is high.

14. The biological information measurement system according to claim 13, wherein the test subject-side data analyzer specifies an initial defecation gas detecting period during the defecation act in the measurement data, and performs analysis on the basis of data in the specified initial defecation gas detection period of the measurement data.

* * * * *